(12) United States Patent
Parham et al.

(10) Patent No.: US 11,621,396 B2
(45) Date of Patent: Apr. 4, 2023

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Jonas Kroeber, Frankfurt am Main (DE); Jens Engelhart, Darmstadt (DE); Anja Jatsch, Frankfurt am Main (DE); Christian Eickhoff, Mannheim (DE); Christian Ehrenreich, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 16/753,489

(22) PCT Filed: Oct. 2, 2018

(86) PCT No.: PCT/EP2018/076730
§ 371 (c)(1),
(2) Date: Apr. 3, 2020

(87) PCT Pub. No.: WO2019/068679
PCT Pub. Date: Apr. 11, 2019

(65) Prior Publication Data
US 2020/0295270 A1   Sep. 17, 2020

(30) Foreign Application Priority Data
Oct. 6, 2017  (EP) ..................... 17195236

(51) Int. Cl.
| | | |
|---|---|---|
| H01L 51/00 | (2006.01) | |
| C07D 487/04 | (2006.01) | |
| C07D 498/04 | (2006.01) | |
| C07D 513/04 | (2006.01) | |
| H01L 51/50 | (2006.01) | |
| C07D 487/12 | (2006.01) | |
| H01G 9/20 | (2006.01) | |
| H01L 51/05 | (2006.01) | |
| H01L 51/42 | (2006.01) | |
| H01L 51/52 | (2006.01) | |

(52) U.S. Cl.
CPC ........ *H01L 51/0071* (2013.01); *C07D 487/04* (2013.01); *C07D 487/12* (2013.01); *C07D 498/04* (2013.01); *C07D 513/04* (2013.01); *H01L 51/0067* (2013.01); *H01L 51/0072* (2013.01); *H01L 51/0073* (2013.01); *H01L 51/5012* (2013.01); *H01L 51/5016* (2013.01); *H01G 9/2059* (2013.01); *H01L 51/0059* (2013.01); *H01L 51/0512* (2013.01); *H01L 51/42* (2013.01); *H01L 51/5296* (2013.01); *H01L 2251/5384* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 4,539,507 A | 9/1985 | VanSlyke et al. | |
| 6,551,723 B1 * | 4/2003 | Okada | H01L 51/004 |
| | | | 313/504 |
| 10,135,003 B2 | 11/2018 | Stoessel et al. | |
| 2005/0074632 A1 | 4/2005 | Lee et al. | |
| 2005/0079387 A1 | 4/2005 | Lee et al. | |
| 2012/0241681 A1 | 9/2012 | Schaefer et al. | |
| 2014/0252280 A1 * | 9/2014 | Schaefer | H01L 51/0067 |
| | | | 252/519.21 |
| 2017/0098783 A1 | 4/2017 | Wolohan et al. | |

FOREIGN PATENT DOCUMENTS

| | | |
|---|---|---|
| CN | 106543205 A | 3/2017 |
| JP | 2015213 119 A | 11/2015 |
| JP | 2015213119 A * | 11/2015 |
| KR | 100553752 B1 | 2/2006 |
| WO | WO-2011160757 A1 | 12/2011 |
| WO | WO-2013068376 A1 | 5/2013 |
| WO | WO-2014009317 A1 | 1/2014 |

OTHER PUBLICATIONS

English machine translation of Hattori et al. (JP 2015-213119 A) accessed online from Espacenet; PDF pp. 1-56. (Year: 2015).*
International Search Report for PCT/EP2018/076730 dated Feb. 1, 2019.
Written Opinion of the International Searching Authority for PCT/EP2018/076730 dated Feb. 1, 2019.

* cited by examiner

*Primary Examiner* — Katie L. Hammer
(74) *Attorney, Agent, or Firm* — Faegre Drinker Biddle & Reath LLP

(57) ABSTRACT

The present invention relates to compounds of the formula (1) which are suitable for use in electronic devices, in particular organic electroluminescent devices, and to electronic devices which comprise these compounds.

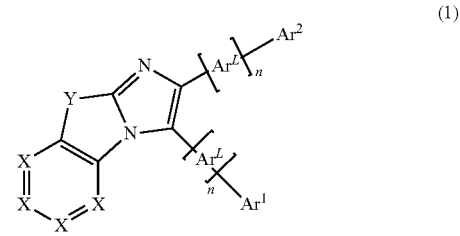

(1)

13 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2018/076730, filed Oct. 2, 2018, which claims benefit of European Application No. 17195236.9, filed Oct. 6, 2017, both of which are incorporated herein by reference in their entirety.

The present invention relates to a compound of the formula (1), to the use of the compound in an electronic device, and to an electronic device comprising a compound of the formula (1). The present invention furthermore relates to a process for the preparation of a compound of the formula (1) and to a formulation comprising one or more compounds of the formula (1).

The structure of organic electroluminescent devices (OLEDs) in which organic semiconductors are employed as functional materials is described, for example in U.S. Pat. No. 4,539,507. The emitting materials employed here are very often organometallic complexes which exhibit phosphorescence. For quantum-mechanical reasons, an up to four-fold increase in efficiency is possible using phosphorescent instead of fluorescent emitters. In general, however, there is still a need for improvement in the case of OLEDs, in particular also in the case of OLEDs which exhibit triplet emission (phosphorescence), for example with respect to efficiency, operating voltage and lifetime.

The properties of phosphorescent OLEDs are not only determined by the triplet emitters but also by the other materials used together with triplet emitters in OLEDs, such as matrix materials, also called host materials. Improvements in these materials and their charge-transport properties can thus also result in significant improvements in the OLED properties.

Thus, the choice of the matrix material in an emission layer comprising a phosphorescent emitter has a great influence on OLEDs properties, especially in terms of efficiency. The matrix material limits the quenching of excited states of emitter molecules by energy transfer.

The object of the present invention is the provision of compounds, which are suitable for use in an OLED, in particular as matrix material for phosphorescent emitters. A further object of the present invention is to provide further organic semiconductors for organic electroluminescent devices to provide the person skilled in the art with a greater possible choice of materials for the production of OLEDs.

Compounds comprising imidazole rings and their use in OLEDs are known from the prior art (for example in US 2005/0074632).

Surprisingly, it has been found that certain compounds containing imidazole rings combined with carbazole rings, as described in greater detail below, exhibit excellent properties when they are employed in OLEDs, particularly when employed as matrix material for phosphorescent emitters. Indeed, these compounds lead to OLEDs exhibiting better properties in terms of lifetime and/or efficiency and/or electroluminescent emission. In addition, these compounds have a high glass transition temperature and a good thermal stability, which is an important property for OLED materials, especially when the materials are vapor-deposited via a vacuum process.

The present invention therefore relates to these compounds and to electronic devices, in particular organic electroluminescent devices, which comprise compounds of this type.

The present invention relates to a compound of the formula (1),

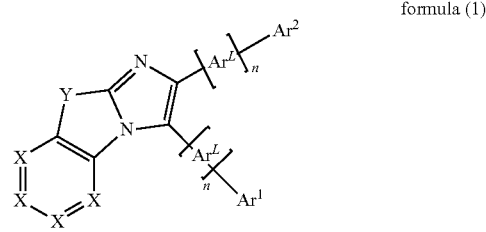

formula (1)

where the following applies to the symbols and indices used:

Y is S, O or NAr$^N$;

X stands, on each occurrence, identically or differently, for N, CR$^1$, C(Ar$^L$)$_n$Ar$^1$ or C(Ar$^L$)$_n$Ar$^2$;

Ar$^L$, Ar$^N$ stand on each occurrence, identically or differently, for an aromatic or heteroaromatic ring system having 5 to 60 aromatic ring atoms, which may be substituted by one or more radicals R$^2$;

Ar$^1$, Ar$^2$ stand on each occurrence, identically or differently, for an aromatic or heteroaromatic ring system having 5 to 60 aromatic ring atoms, which may be substituted by one or more radicals R$^3$;

where the compound of formula (1) comprises at least one group Ar$^1$ or Ar$^2$, which stands for a heteroaromatic ring system of formula (Cbz-1):

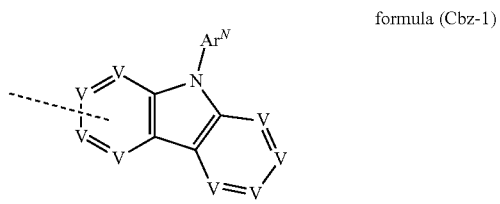

formula (Cbz-1)

where the dashed bond indicates the bonding of Ar$^1$ or Are to the structure of formula (1) or to Ar$^L$;

V stands, on each occurrence, identically or differently, for CR$^3$ or N or V stands for C when it is bonded to the structure of formula (1) or to Ar$^L$; or two adjacent groups V stand for a group of formula (V-1) or (V-2),

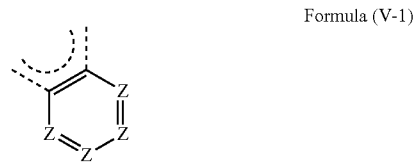

Formula (V-1)

-continued

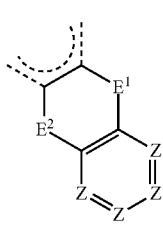

Formula (V-2)

where the dashed bonds in formulae (V-1) and (V-2) indicate the bonding to the group of formula (Cbz-1);

Z is on each occurrence, identically or differently, $CR^3$ or N;

$E^1$, $E^2$ are, on each occurrence, identically or differently, selected from a single bond, $B(R^0)$, $C(R^0)_2$, $Si(R^0)_2$, C=O, C=NR$^0$), C=C($R^0$)$_2$, O, S, S=O, $SO_2$, $N(R^0)$, $P(R^0)$ and P(=O)$R^0$, where at least one of the two groups $E^1$ and $E^2$ present in the same ring, is not a single bond;

$R^0$ stands on each occurrence, identically or differently, for H, D, F, Cl, Br, I, CN, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^4$, where in each case one or more non-adjacent $CH_2$ groups may be replaced by $R^4C$=$CR^4$, C≡C, $Si(R^4)_2$, $Ge(R^4)_2$, $Sn(R^4)_2$, C=O, C=S, C=Se, P(=O)($R^4$), SO, $SO_2$, O, S or $CONR^4$ and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^4$, or an aryloxy groups having 5 to 60 aromatic ring atoms, which may be substituted by one or more radicals $R^4$, where two adjacent substituents $R^0$ may form an aliphatic or aromatic ring system together, which may be substituted by one or more radicals $R^4$;

$R^1$, $R^2$, $R^3$ stand on each occurrence, identically or differently, for H, D, F, Cl, Br, I, CHO, CN, C(=O)Ar, P(=O)(Ar)$_2$, S(=O)Ar, S(=O)$_2$Ar, $N(R^4)_2$, $N(Ar)_2$, $NO_2$, $Si(R^4)_3$, $B(OR^4)_2$, $OSO_2R^4$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^4$, where in each case one or more non-adjacent $CH_2$ groups may be replaced by $R^4C$=$CR^4$, C≡C, $Si(R^4)_2$, $Ge(R^4)_2$, $Sn(R^4)_2$, C=O, C=S, C=Se, P(=O)($R^4$), SO, $SO_2$, O, S or $CONR^4$ and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^4$, or an aryloxy groups having 5 to 60 aromatic ring atoms, which may be substituted by one or more radicals $R^4$; where two adjacent substituents $R^1$, two adjacent substituents $R^2$ and/or two adjacent substituents $R^3$ may form an aliphatic or aromatic ring system together, which may be substituted by one or more radicals $R^4$;

$R^4$ stands on each occurrence, identically or differently, for H, D, F, Cl, Br, I, CHO, CN, C(=O)Ar, P(=O)(Ar)$_2$, S(=O)Ar, S(=O)$_2$Ar, $N(R^5)_2$, $N(Ar)_2$, $NO_2$, $Si(R^5)_3$, $B(OR^5)_2$, $OSO_2R^5$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^5$, where in each case one or more non-adjacent $CH_2$ groups may be replaced by $R^5C$=$CR^5$, C≡C, $Si(R^5)_2$, $Ge(R^5)_2$, $Sn(R^5)_2$, C=O, C=S, C=Se, P(=O)($R^5$), SO, $SO_2$, O, S or $CONR^5$ and where one or more H atoms may be replaced by D, F, Cl, Br, I, CN or $NO_2$, an aromatic or heteroaromatic ring systems having 5 to 60 aromatic ring atoms, which may in each case be substituted by one or more radicals $R^5$, or an aryloxy groups having 5 to 60 aromatic ring atoms, which may be substituted by one or more radicals $R^5$; where two adjacent substituents $R^4$ may form an aliphatic or aromatic ring system together, which may be substituted by one or more radicals $R^5$;

Ar is, on each occurrence, identically or differently, an aromatic or heteroaromatic ring system having 5 to 60 aromatic ring atoms, which may in each case also be substituted by one or more radicals $R^5$;

$R^5$ stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent $CH_2$ groups may be replaced by SO, $SO_2$, O, S and where one or more H atoms may be replaced by D, F, Cl, Br or I, or an aromatic or heteroaromatic ring system having 5 to 24 aromatic ring atoms;

n is an integer equal to 0, 1, 2 or 3.

The fact that the compound of formula (1) comprises at least one group Ar' or $Ar^2$, which stands for heteroaromatic ring system of formula (Cbz-1) is taken to mean that either at least one group $Ar^1$ or $Ar^2$, which is explicitly depicted in the structure of formula (1) above, stands for a group of formula (Cbz-1), or at least one group X depicted in formula (1) stands for a group $C(Ar^L)_nAr^1$ or $C(Ar^L)_nAr^2$, where $Ar^1$ or $Ar^2$ stands for a group of formula (Cbz-1).

Adjacent substituents in the sense of the present invention are substituents which are bonded to carbon atoms which are linked directly to one another or which are bonded to the same carbon atom.

Furthermore, the following definitions of chemical groups apply for the purposes of the present application:

An aryl group in the sense of this invention contains 6 to 60 aromatic ring atoms; a heteroaryl group in the sense of this invention contains 5 to 60 aromatic ring atoms, at least one of which is a heteroatom. The hetero atoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two radicals may form a ring with one another is, for the purposes of the present application, intended to be taken to mean, inter alia, that the two radicals are linked to one another by a chemical bond. This is illustrated by the following schemes:

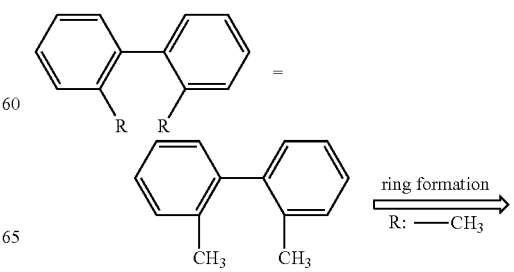

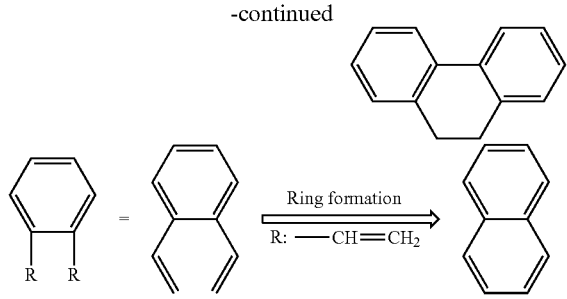

Furthermore, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

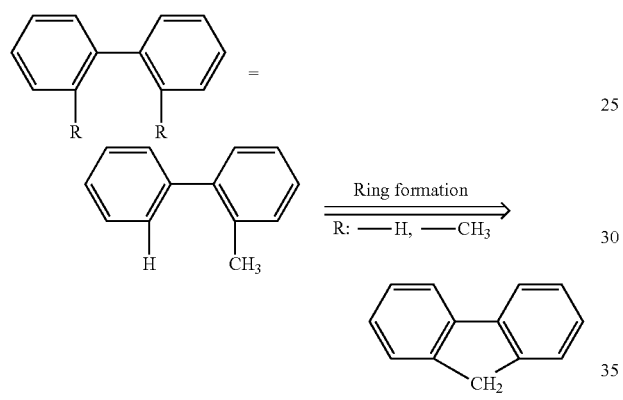

Preferably, the heteroaromatic ring system of formula (Cbz-1) is selected from heteroaromatic ring systems of formula (Cbz-1a),

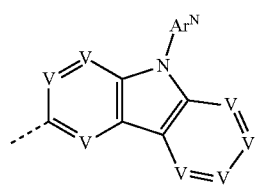

formula (Cbz-1a)

where the dashed bond indicates the bonding to the structure of formula (1) or to $Ar^L$.

Preferably, there are maximum two groups X per 6-membered ring, which stand for N and there are maximum two groups V per 6-membered ring, which stand for N. Very preferably, there is maximum one group X per 6-membered ring, which stands for N and there is maximum one group V per 6-membered ring, which stands for N. Particularly preferably, X stands for $CR^1$, $C(Ar^L)_n Ar^1$, or $C(Ar^L)_n Ar^2$. Particularly preferably, V stands for $CR^3$.

In accordance with a preferred embodiment of the invention, the group Y is selected from O or S.

In accordance with a preferred embodiment, $Ar^1$ and $Ar^2$ are, identically or differently, selected from the group consisting of aromatic and heteroaromatic ring systems having 6 to 30 aromatic ring atoms, which may be substituted by one or more radicals $R^3$, where the compound of formula (1) comprises at least one group $Ar^1$ or $Ar^2$, which stands for a heteroaromatic ring system of formula (Cbz-1).

In accordance with a preferred embodiment, $Ar^1$ and $Ar^2$ are on each occurence, identically or differently, selected from the group consisting of phenyl, biphenyl, particularly ortho-, meta- and para-biphenyl, terphenyl, particularly ortho-, meta-, para- and branched terphenyl, quaterphenyl, particularly ortho-, meta-, para- and branched quaterphenyl, fluorene, which may be connected to the structure of formula (1) via the 1-, 2-, 3- or 4-position, spirobifluorene, which may be connected to the structure of formula (1) via the 1-, 2-, 3- or 4-position, naphthalene, anthracene, phenanthrene, triphenylene, fluoranthene, indole, benzofuran, benzothiophen, dibenzofuran, which may be connected to the structure of formula (1) via the 1-, 2-, 3- or 4-position, dibenzothiophene, which may be connected to the structure of formula (1) via the 1-, 2-, 3- or 4-position, carbazole, may be connected to the structure of formula (1) via the 1-, 2-, 3- or 4-position, indenocarbazole, indolocarbazole, pyridine, pyrimidine, pyrazine, pyridazine, triazine, quinazoline, quinoxaline, benzimidazole, or a combination of two or three of these groups, each of which may be substituted by one or more radicals $R^3$, and where the compound of formula (1) comprises at least one group $Ar^1$ or $Ar^2$, which stands for heteroaromatic ring system of formula (Cbz-1).

Suitable groups $Ar^1$ and $Ar^2$, besides the groups of formula (Cbz-1), are the groups of formulae (Ar1-1) to (Ar1-12) listed in the table below:

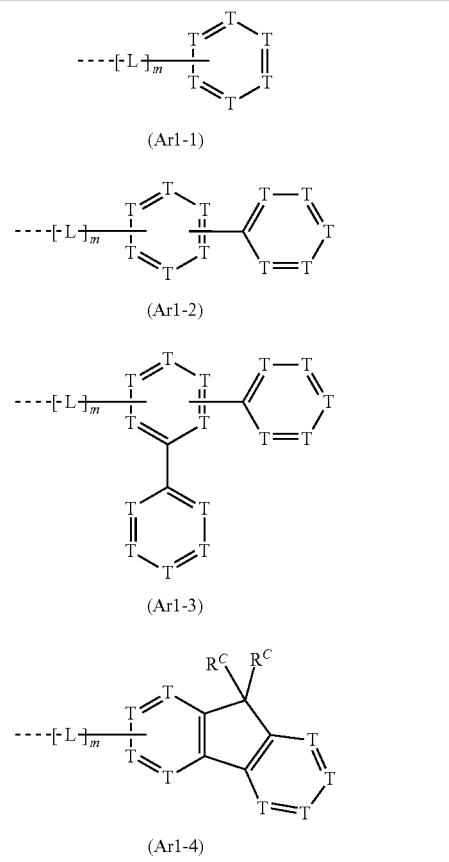

-continued

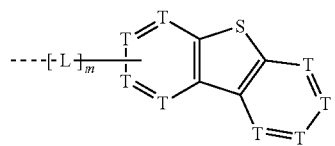

(Ar1-5)

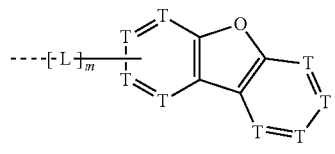

(Ar1-6)

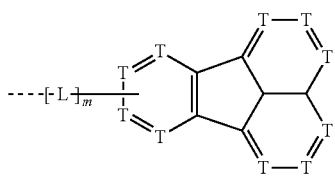

(Ar1-7)

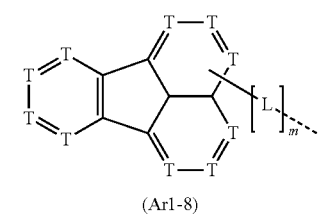

(Ar1-8)

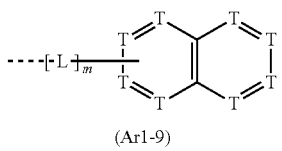

(Ar1-9)

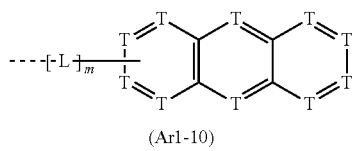

(Ar1-10)

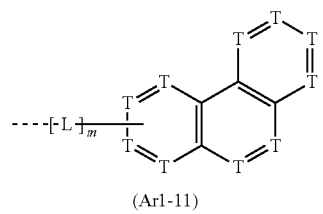

(Ar1-11)

-continued

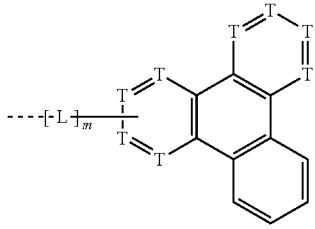

(Ar1-12)

where:
the dashed bond indicates the bonding to the structure of formulae (1);
T stands, on each occurrence, identically or differently, for $CR^3$ or N; or T stands for C when it is bonded to the structure of formula (1) or to L; or two adjacent groups T stand for a group of formula (T-1) or (T-2),

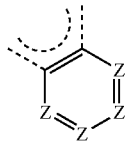

Formula (T-1)

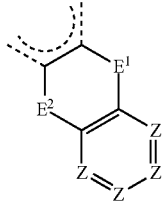

Formula (T-2)

where
the dashed bonds in formulae (T-1) and (T-2) indicate the bonding to the corresponding adjacent groups T in formulae (Ar1-1) to (Ar1-12); the symbols Z, $E^1$ and $E^2$ have the same meaning as above: and
$R^C$ stands on each occurrence, identically or differently, for H, D, F, Cl, Br, I, CHO, CN, C(=O)Ar, P(=O)(Ar)$_2$, S(=O)Ar, S(=O)$_2$Ar, N(R$^2$)$_2$, N(Ar)$_2$, NO$_2$, Si(R$^4$)$_3$, B(OR$^4$)$_2$, OSO$_2$R$^4$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals R$^4$, where in each case one or more non-adjacent CH$_2$ groups may be replaced by R$^4$C=CR$^4$, C≡C, Si(R$^4$)$_2$, Ge(R$^4$)$_2$, Sn(R$^4$)$_2$, C=O, C=S, C=Se, P(=O)(R$^4$), SO, SO$_2$, O, S or CONR$^4$ and where one or more H atoms may be replaced by D, F, Cl, Br, I, CN or NO$_2$, an aromatic or heteroaromatic ring systems having 5 to 60 aromatic ring atoms, which may in each case be substituted by one or more radicals R$^4$, or an aryloxy groups having 5 to 60 aromatic ring atoms, which may be substituted by one or more radicals R$^4$; where two adjacent substituents R$^C$ may form an aliphatic or aromatic ring system together, which may be substituted by one or more radicals R$^4$; where R$^4$ and Ar have the same meaning as above;

L is an aromatic or heteroaromatic ring system having 5 to 30 aromatic ring atoms, which may be substituted by one or more radicals $R^4$;

m is 0 or 1, preferably 0.

L is preferably an aromatic or heteroaromatic ring system having 5 to 18 aromatic ring atoms, which may be substituted by one or more radicals $R^4$. L is very preferably an aromatic ring system having 6 to 12 aromatic ring atoms, which may be substituted by one or more radicals $R^4$. L is particularly preferably a phenyl group, which may be substituted by one or more radicals $R^4$.

Very suitable groups $Ar^1$ and Are, besides the groups of formula (Cbz-1), are the groups of formulae (Ar1-13) to (Ar1-12) listed in the table below:

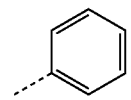
(Ar1-13)

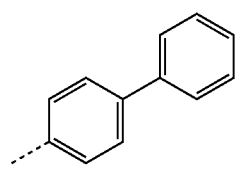
(Ar1-14)

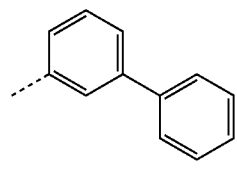
(Ar1-15)

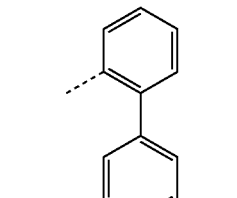
(Ar1-16)

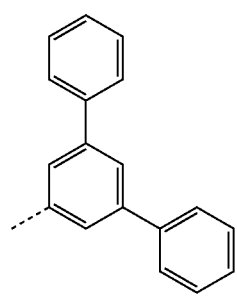
(Ar1-17)

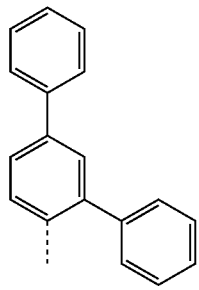
(Ar1-18)

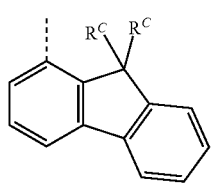
(Ar1-19)

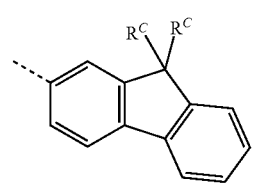
(Ar1-20)

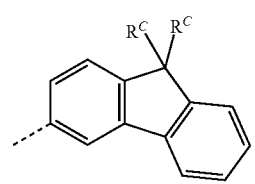
(Ar1-21)

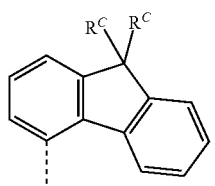
(Ar1-22)

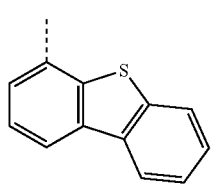
(Ar1-23)

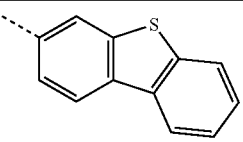
(Ar1-24)
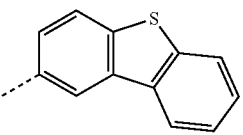
(Ar1-25)
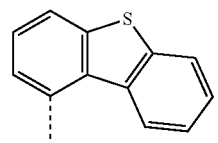
(Ar1-26)
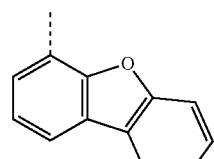
(Ar1-27)
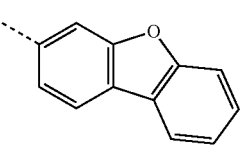
(Ar1-28)
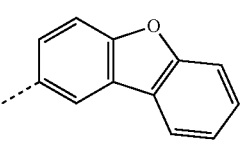
(Ar1-29)
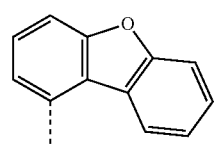
(Ar1-30)
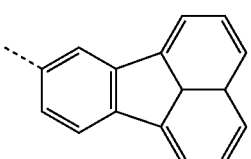
(Ar1-31)
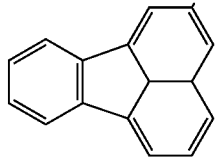
(Ar1-32)
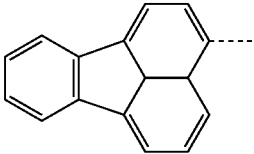
(Ar1-33)
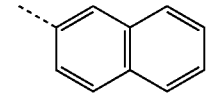
(Ar1-34)
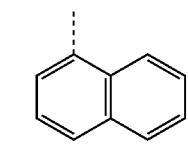
(Ar1-35)
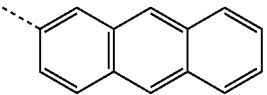
(Ar1-36)
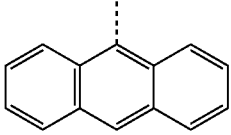
(Ar1-37)
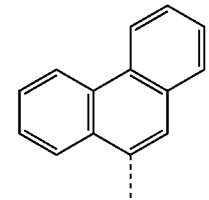
(Ar1-38)
(Ar1-39)

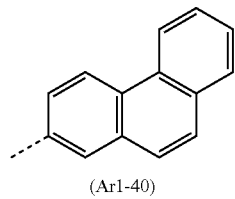

(Ar1-40)

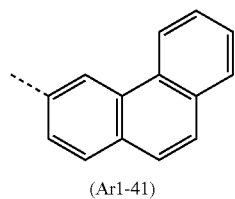

(Ar1-41)

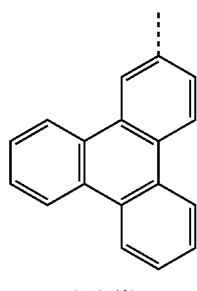

(Ar1-42)

where
the dashed bond indicates the bonding to the group of formula (1);
$R^C$ has the same meaning as above; and
the groups of formulae (Ar1-13) to (Ar1-42) are optionally substituted by one or more radicals $R^3$ at any free positions.

In accordance with a preferred embodiment, the compounds of formula (1) are selected from the compounds of formulae (2-1) to (2-6) as listed below, formula (2-1)

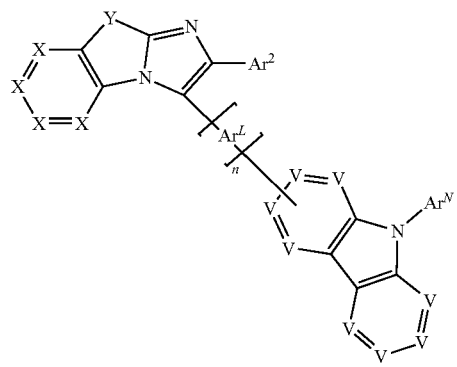

formula (2-2)

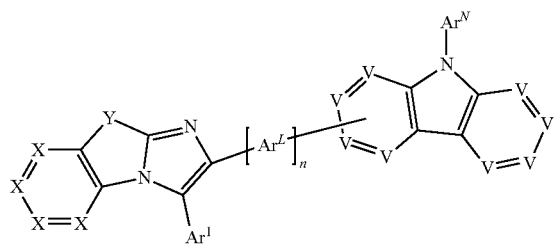

formula (2-3)

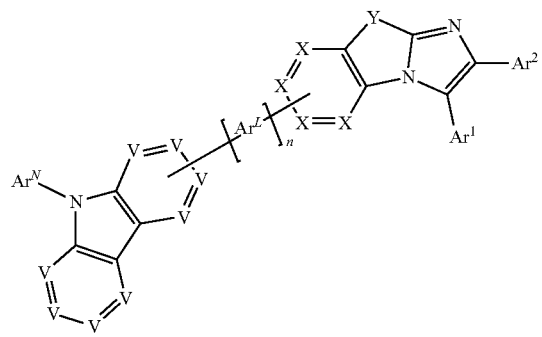

formula (2-4)

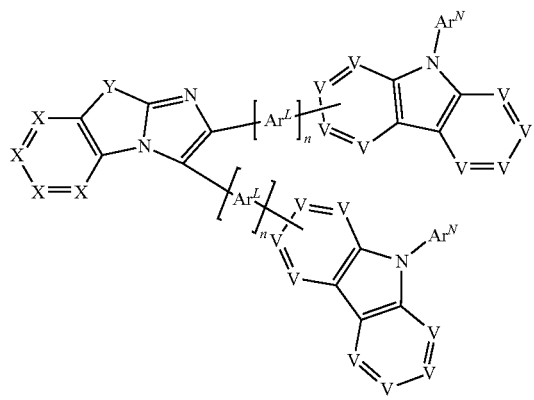

-continued formula (2-5)

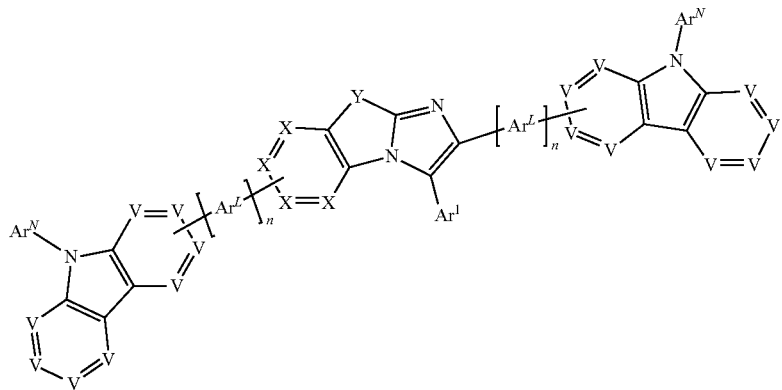

formula (2-6)

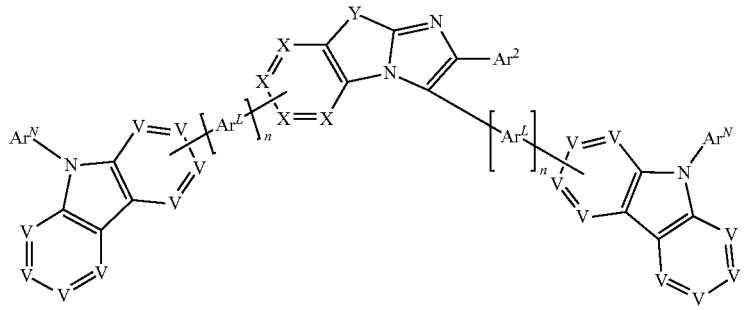

where the symbols V, Y, $Ar^1$, $Ar^2$, $Ar^L$ and $Ar^N$ and the index n have the same meaning as above and the symbol X also has the same meaning as above, with the proviso that X stands for C if it is bonded to an adjacent group in formulae (2-5) to (2-6) (carbazole unit or group $Ar^L$ as depicted in formulae (2-5) and (2-6)).

In accordance with a preferred embodiment of the invention, the index n is 0 or 1, wherein when n is 1, then the group $Ar^L$ is present and stands for a group of formula (Cbz-2):

formula (Cbz-2)

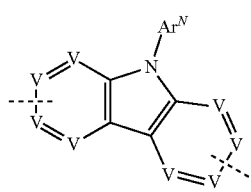

where the dashed bonds indicate the bonding to the group $Ar^1$ or $Ar^2$ and to the structure of formula (1), and where the symbols V and $Ar^N$ have the same meaning as above.

In accordance with a very preferred embodiment of the invention, the index n is 0 or 1, wherein when n is 1, then the group $Ar^L$ is present and stands for a group of formula (Cbz-2a):

formula (Cbz-2a)

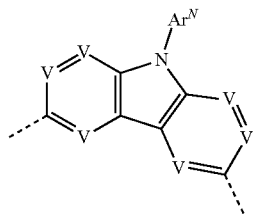

where the dashed bonds indicate the bonding to the group $Ar^1$ or $Ar^2$ and to the structure of formula (1), and where the symbols V and $Ar^N$ have the same meaning as above.

In accordance with a very preferred embodiment, the compounds of formula (1) are selected from the compounds of formulae (3-1) to (3-6) as listed below, formula (3-1)

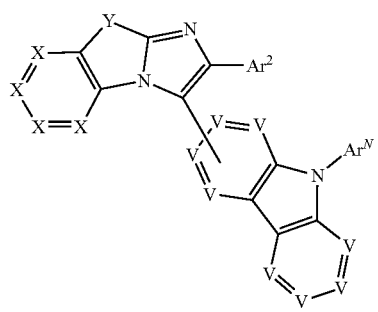

-continued formula (3-2)

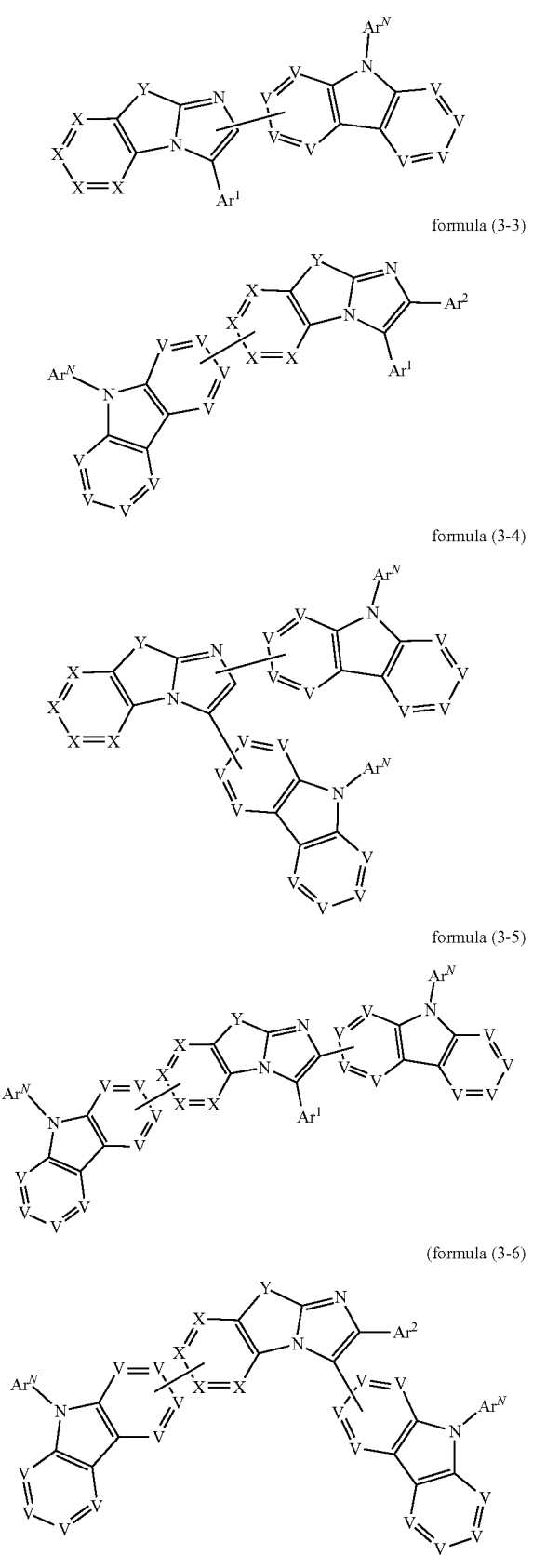

formula (3-3)

formula (3-4)

formula (3-5)

(formula (3-6)

where the symbols V, Y, Ar¹, Ar² and Ar^N have the same meaning as above, the symbol X also has the same meaning as above, with the proviso that X stands for C in formulae (3-5) and (3-6), if it is bonded to the adjacent carbazole unit as depicted in formulae (3-5) and (3-6).

In accordance with a particularly preferred embodiment, the compounds of formula (1) are selected from the compounds of formulae (4-1) to (4-6) as listed below, formula (4-1)

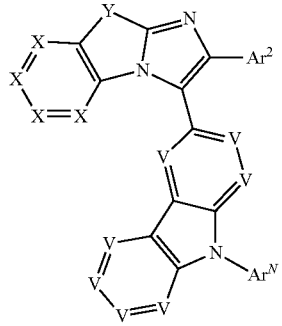

formula (4-2)

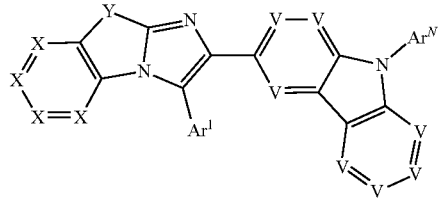

formula (4-3)

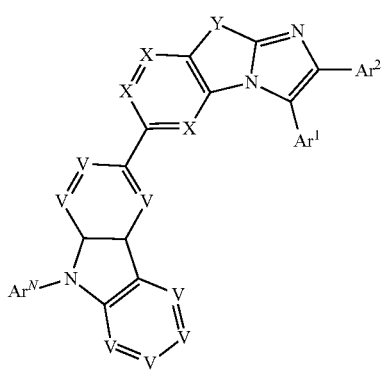

(formula (4-4)

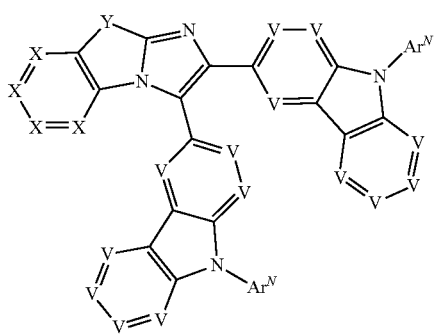

formula (4-5)

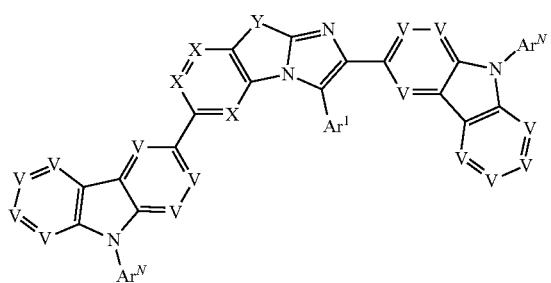

(formula (4-6))

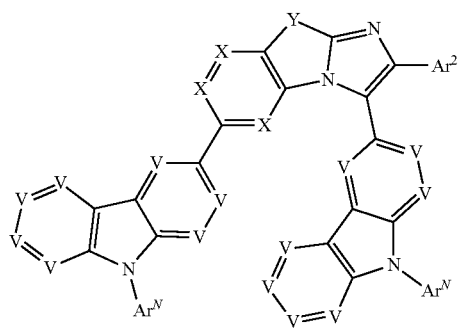

where the symbols X, V, Y, $Ar^1$, $Ar^2$ and $Ar^N$ have the same meaning as above.

In accordance with another particularly preferred embodiment, the compounds of formula (1) are selected from the compounds of formulae (5-1) to (5-3) as listed below, formula (5-1)

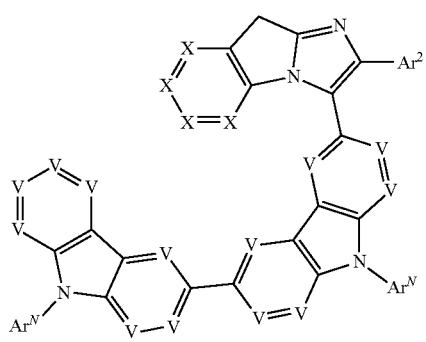

formula (5-2)

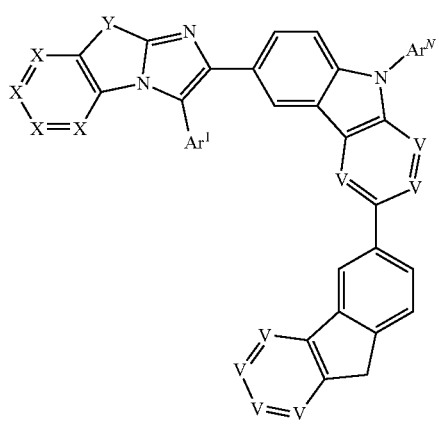

formula (5-3)

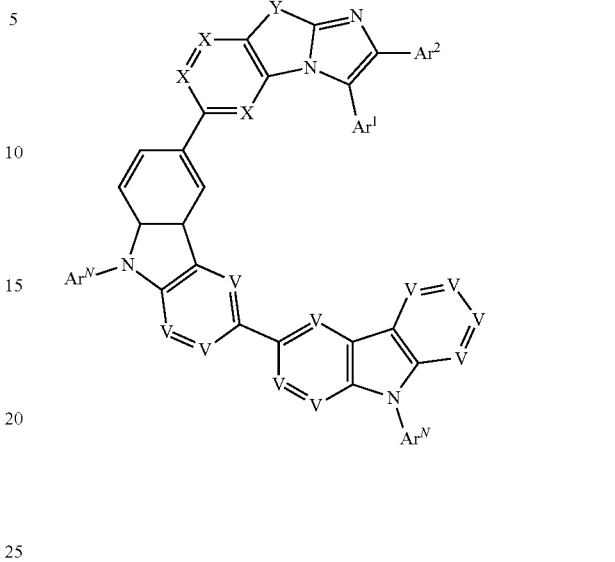

where the symbols X, V, Y, $Ar^1$, $Ar^2$ and $Ar^N$ have the same meaning as above.

In the case that two adjacent groups V stand for a group of formula (V-2) as defined above, it is preferred that $E^1$, $E^2$ are, on each occurrence, identically or differently, selected from a single bond), $C(R^0)_2$, C=O, O, S, S=O, $SO_2$ and) $N(R^0)$, where at least one of the groups $E^1$ and $E^2$, present in the same ring, is not a single bond. Very preferably, one of the groups $E^1$ and $E^2$ is a single bond and the other group is $C(R^0)_2$, C=O, O, S, S=O, $SO_2$ or $N(R^0)$.

Particularly preferably, one of the groups $E^1$ and $E^2$ is a single bond and the other one is $C(R^0)_2$, O, S, or $N(R^0)$.

Furthermore, it is preferred that $R^0$ stands on each occurrence, identically or differently, for H, D, F, a straight-chain alkyl group having 1 to 10 C atoms or branched or a cyclic alkyl group having 3 to 10 C atoms, each of which may be substituted by one or more radicals $R^4$, where one or more H atoms may be replaced by D or F, an aromatic or heteroaromatic ring systems having 5 to 18 aromatic ring atoms, which may in each case be substituted by one or more radicals $R^4$, where two adjacent substituents $R^0$ may form an aliphatic or aromatic ring system together, which may be substituted by one or more radicals $R^4$.

In accordance with a preferred embodiment, the group $Ar^N$ is, on each occurrence, identically or differently, an aromatic or heteroaromatic ring system having 5 to 30 aromatic ring atoms, more preferably 5 to 18 aromatic ring atoms, which may be substituted by one or more radicals $R^2$. Particularly preferably, $Ar^N$ is, on each occurrence, identically or differently, selected from the group consisting of phenyl, biphenyl, terphenyl, quaterphenyl, fluorene, spirobifluorene, naphthalene, anthracene, phenanthrene, triphenylene, fluoranthene, indole, benzofuran, benzothiophen, dibenzofuran, dibenzothiophene, carbazole, indenocarbazole, indolocarbazole, pyridine, pyrimidine, pyrazine, pyridazine, triazine, quinolone, benzopyridine, benzopyridazine, benzopyrimidine, quinazoline, benzimidazole, or a combination of two or three of these groups, each of which may be substituted by one or more radicals $R^2$.

Examples of suitable groups $Ar^N$ are the groups of formulae (ArN-1) to (ArN15) listed in the table below:

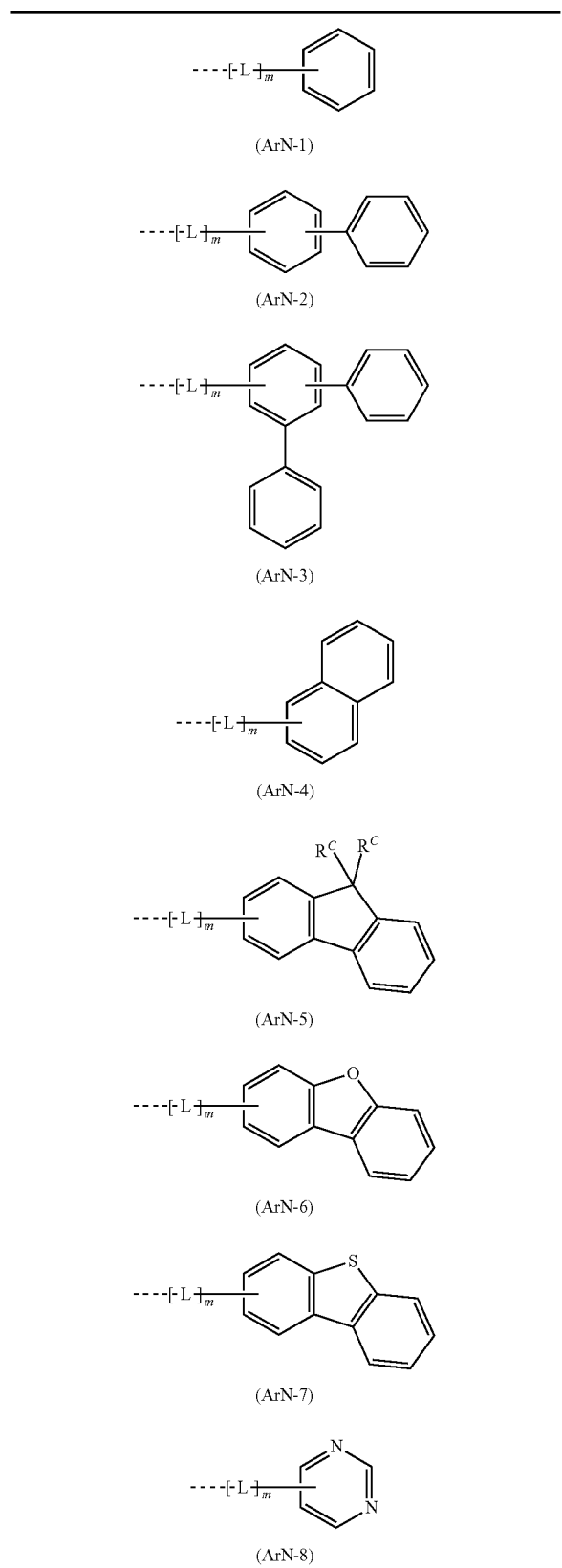

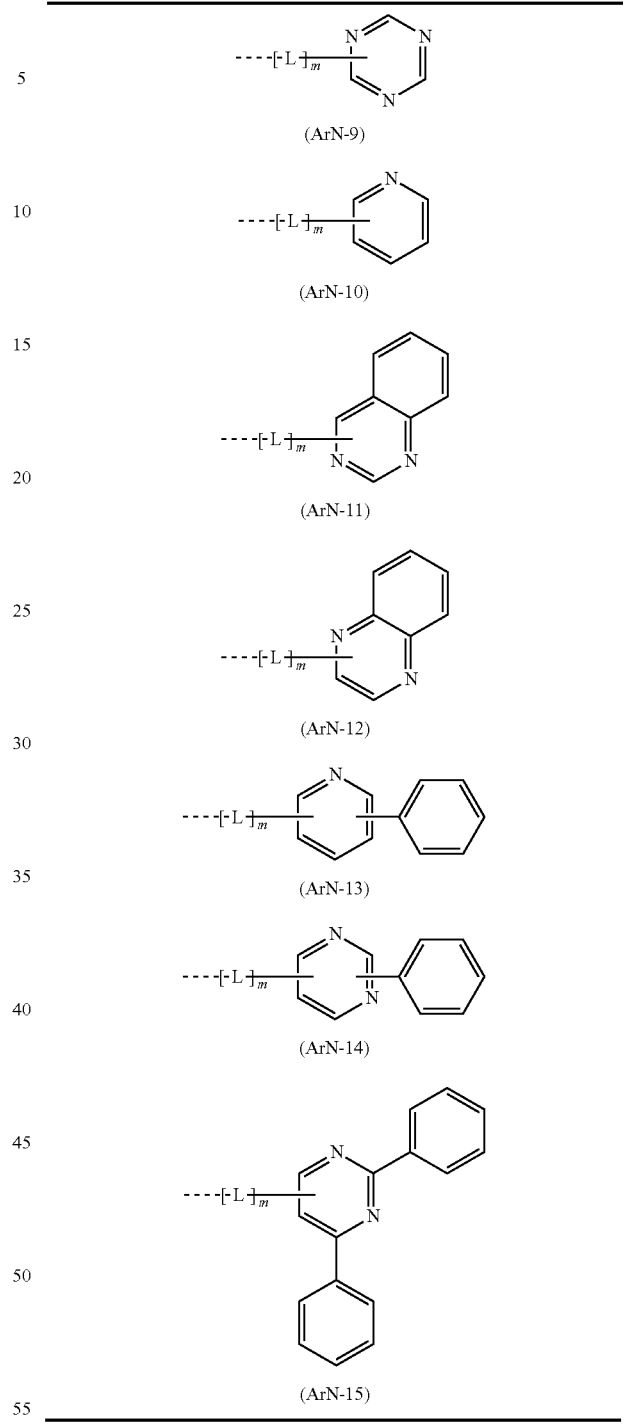

where:
the dashed bond indicates in formulae (ArN-1) to (ArN-15) indicates the bonding of the corresponding group $Ar^N$ to the nitrogen atom of the group "N—$Ar^N$", and where $R^C$, L and m have the same meaning as above.

Among the groups of formulae (ArN-1) to (ArN-15), the groups of formulae (ArN-1), (ArN-2), (ArN-6), (ArN-9) and (ArN-12) are preferred.

Preferably, $R^1$, $R^2$, $R^3$ stand on each occurrence, identically or differently, for H, D, F, CN, $N(Ar)_2$, a straight-chain alkyl group having 1 to 20 C atoms or branched or a cyclic alkyl group having 3 to 20 C atoms, each of which may be substituted by one or more radicals $R^4$, where in each case one or more non-adjacent $CH_2$ groups may be replaced by $R^4C=CR^4$, C=O, O or S and where one or more H atoms may be replaced by D or F, an aromatic or heteroaromatic ring systems having 5 to 40 aromatic ring atoms, preferably 5 to 25 aromatic ring atoms, which may in each case be substituted by one or more radicals $R^4$; where two adjacent substituents $R^1$, two adjacent substituents $R^2$, two adjacent substituent $R^3$ may form an aliphatic or aromatic ring system together, which may be substituted by one or more radicals $R^4$.

Preferably, the group $R^C$ is on each occurence, identically or differently, selected from the group consisting of H, D, F, CN, $Si(R^4)_3$, a straight-chain alkyl group having 1 to 10 C atoms or a branched or cyclic alkyl group having 3 to 10 C atoms, each of which may be substituted by one or more radicals $R^4$, an aromatic or heteroaromatic group having 5 to 25 aromatic ring atoms, each of which may be substituted by one or more radicals $R^4$, where two adjacent substituents $R^C$ may optionally form a mono- or polycyclic, aliphatic ring system or aromatic ring system, each of which may be substituted by one or more radicals $R^4$. More preferably, $R^C$ is selected on each occurrence, identically or differently, from the group consisting of H, a straight-chain alkyl group having 1 to 5 C atoms or a branched or cyclic alkyl group having 3 to 5 C atoms, each of which may be substituted by one or more radicals $R^4$, an aryl or heteroaryl group having 5 to 18 aromatic ring atoms, each of which may be substituted by one or more radicals $R^4$.

It is preferred that $R^4$ stands on each occurrence, for H, D, F, CN, $N(Ar)_2$, a straight-chain alkyl group having 1 to 10 C atoms or branched or a cyclic alkyl group having 3 to 10 C atoms, each of which may be substituted by one or more radicals $R^5$, where one or more H atoms may be replaced by D or F, an aromatic or heteroaromatic ring systems having 5 to 18 aromatic ring atoms, which may in each case be substituted by one or more radicals $R^5$.

It is preferred that Ar is, on each occurrence, identically or differently, an aromatic or heteroaromatic ring system having 5 to 40 aromatic ring atoms, preferably 6 to 30, more preferably 6 to 18 aromatic ring atoms, which may in each case also be substituted by one or more radicals $R^5$.

It is further more preferred that $R^5$ stands on each occurrence, identically or differently, for H, D, F, Cl, Br, I, CN, a straight-chain alkyl, alkoxy or thioalkyl groups having 1 to 10 C atoms or branched or cyclic alkyl, alkoxy or thioalkyl groups having 3 to 10 C atoms, where one or more H atoms may be replaced by D, F, Cl, Br or I, or an aromatic or heteroaromatic ring system having 5 to 24, preferably 6 to 18 atoms aromatic ring atoms.

Examples of suitable compounds according to the invention are the structures shown in the table below:

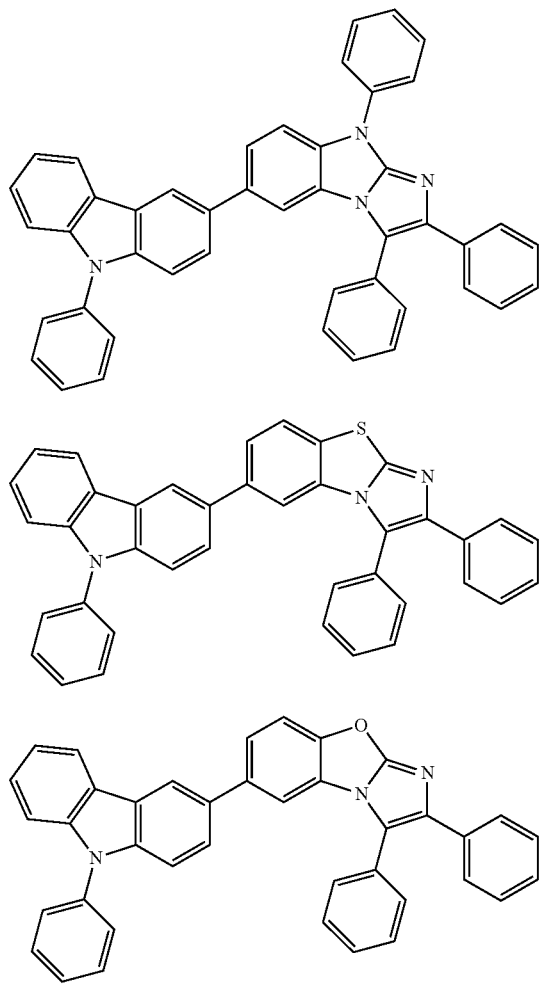

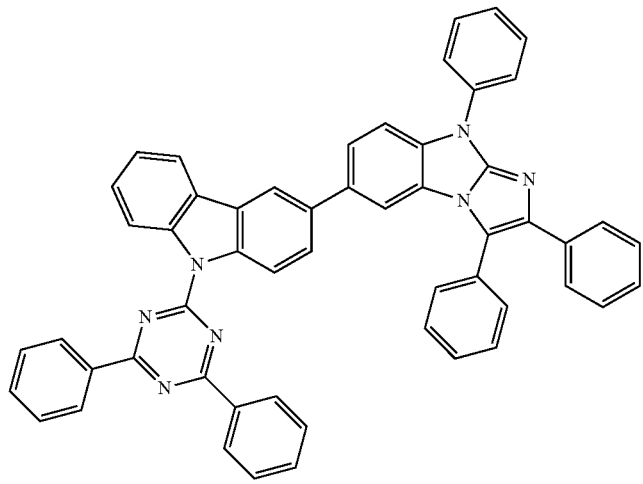 [SMILES: c1ccc(-c2nc(-c3ccccc3)nc(-n3c4ccccc4c4cc(-c5ccc6c(c5)n5c(-c7ccccc7)c(-c7ccccc7)nc5n6-c5ccccc5)ccc43)n2)cc1]
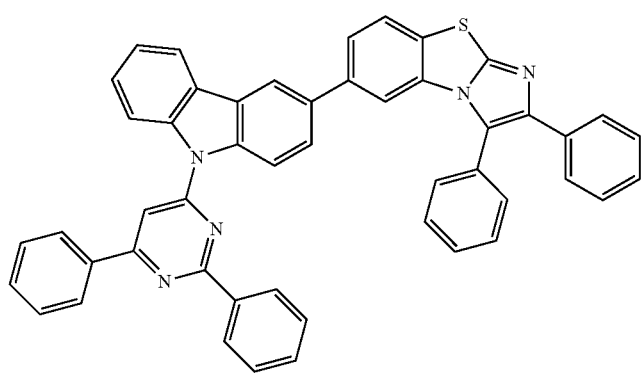 [SMILES: c1ccc(-c2cc(-n3c4ccccc4c4cc(-c5ccc6sc7nc(-c8ccccc8)c(-c8ccccc8)n7c6c5)ccc43)nc(-c3ccccc3)n2)cc1]
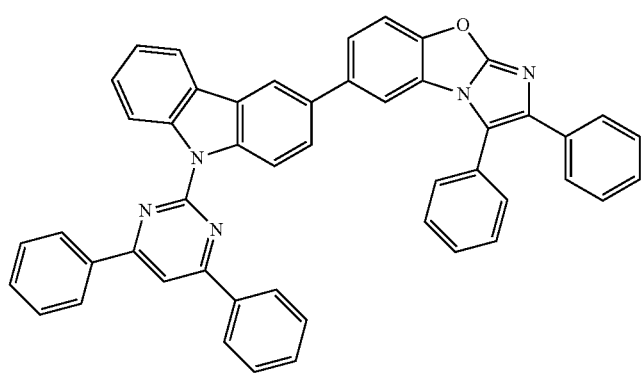 [SMILES: c1ccc(-c2cc(-c3ccccc3)nc(-n3c4ccccc4c4cc(-c5ccc6oc7nc(-c8ccccc8)c(-c8ccccc8)n7c6c5)ccc43)n2)cc1]

-continued
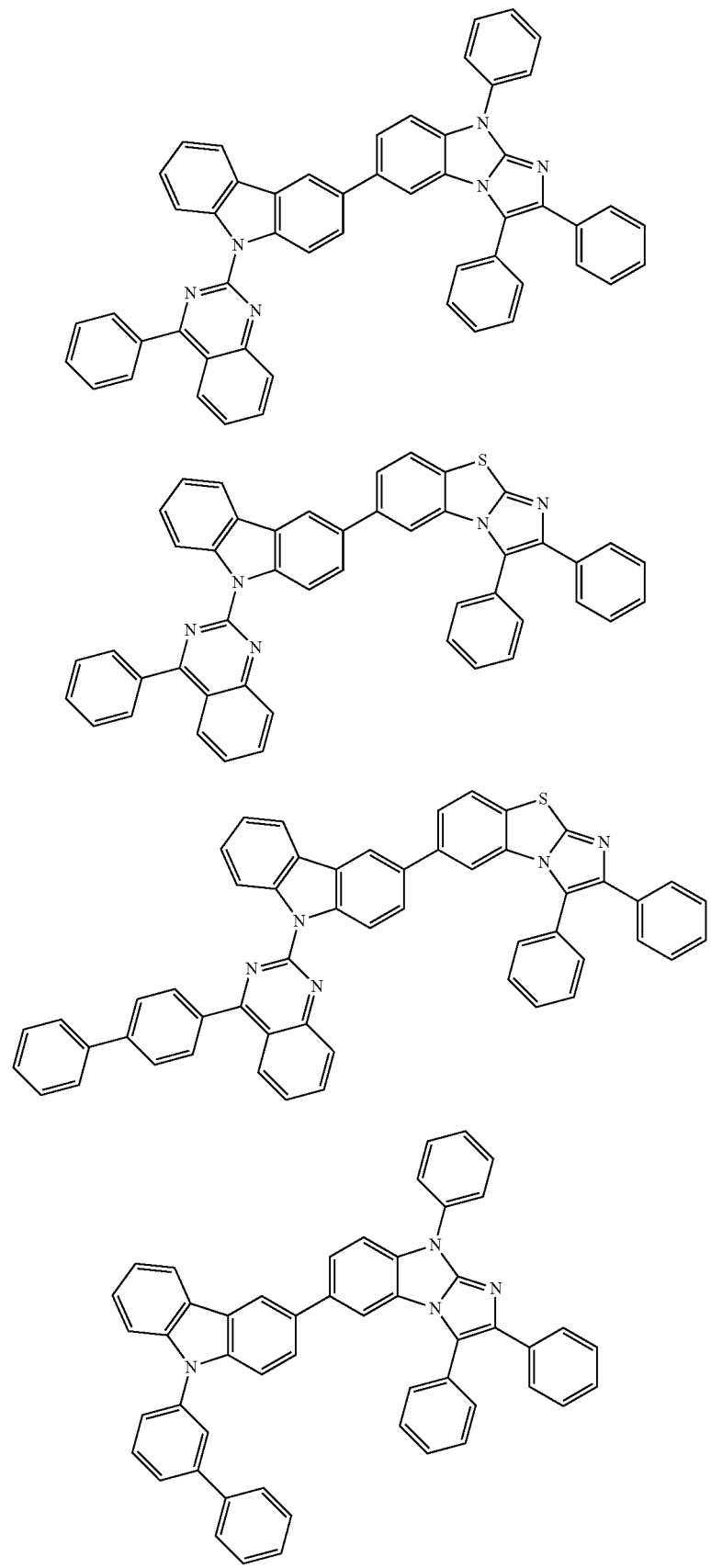

-continued
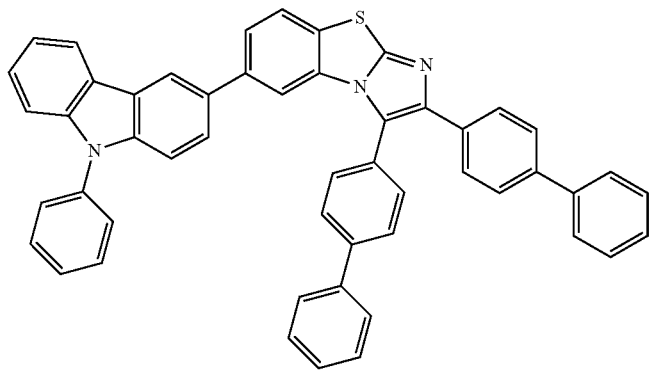 [SMILES: c1ccc(-c2ccc(-c3nc4sc5ccc(-c6ccc7c(c6)c6ccccc6n7-c6ccccc6)cc5n4c3-c3ccc(-c4ccccc4)cc3)cc2)cc1]
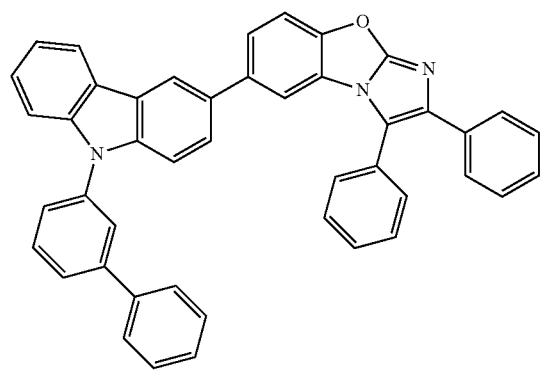 [SMILES: c1ccc(-c2cccc(-n3c4ccccc4c4cc(-c5ccc6oc7nc(-c8ccccc8)c(-c8ccccc8)n7c6c5)ccc43)c2)cc1]
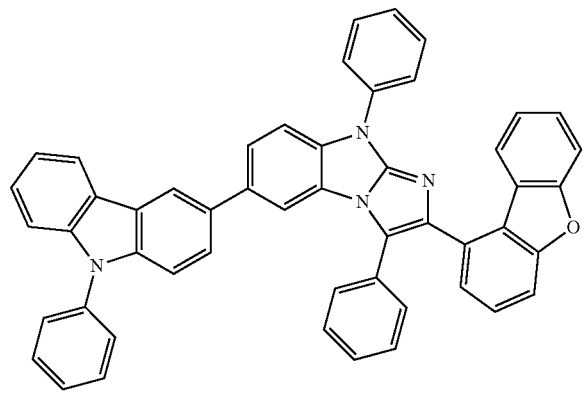 [SMILES: c1ccc(-c2c(-c3cccc4oc5ccccc5c34)nc3n(-c4ccccc4)c4ccc(-c5ccc6c(c5)c5ccccc5n6-c5ccccc5)cc4n23)cc1]
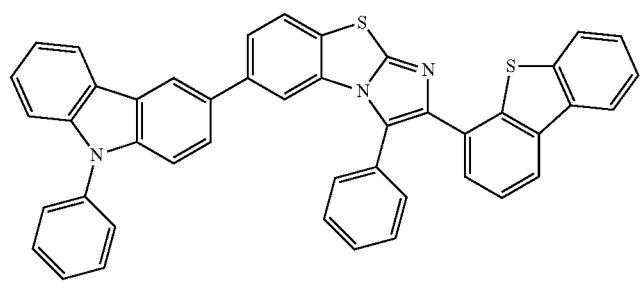 [SMILES: c1ccc(-c2c(-c3cccc4c3sc3ccccc34)nc3sc4ccc(-c5ccc6c(c5)c5ccccc5n6-c5ccccc5)cc4n23)cc1]

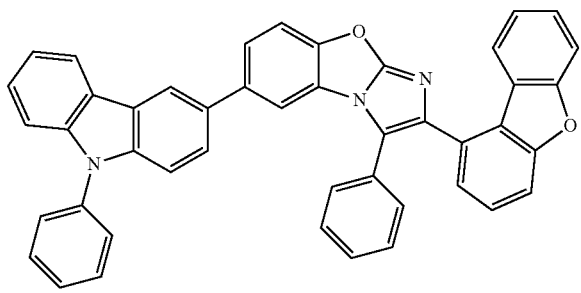 [SMILES: c1ccc(-c2c(-c3cccc4oc5ccccc5c34)nc3oc4ccc(-c5ccc6c(c5)c5ccccc5n6-c5ccccc5)cc4n23)cc1]
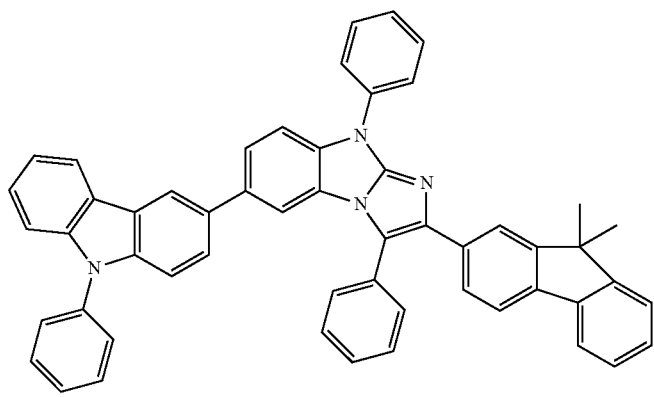 [SMILES: CC1(C)c2ccccc2-c2ccc(-c3nc4n(-c5ccccc5)c5ccc(-c6ccc7c(c6)c6ccccc6n7-c6ccccc6)cc5n4c3-c3ccccc3)cc21]
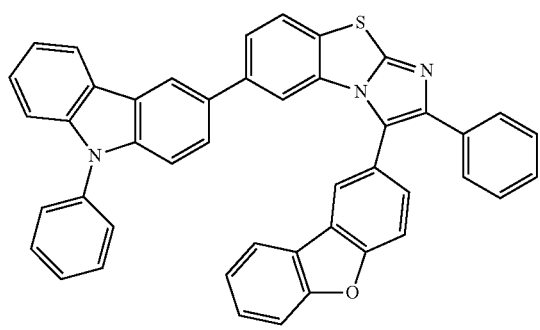 [SMILES: c1ccc(-c2nc3sc4ccc(-c5ccc6c(c5)c5ccccc5n6-c5ccccc5)cc4n3c2-c2ccc3oc4ccccc4c3c2)cc1]
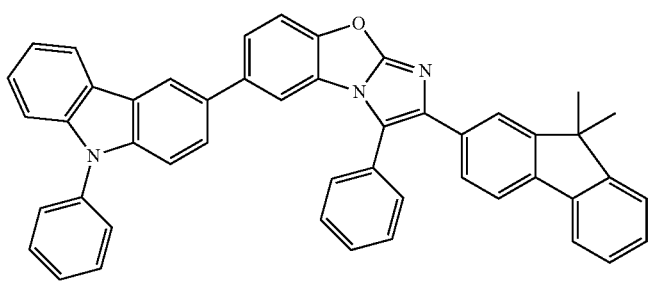 [SMILES: CC1(C)c2ccccc2-c2ccc(-c3nc4oc5ccc(-c6ccc7c(c6)c6ccccc6n7-c6ccccc6)cc5n4c3-c3ccccc3)cc21]

-continued
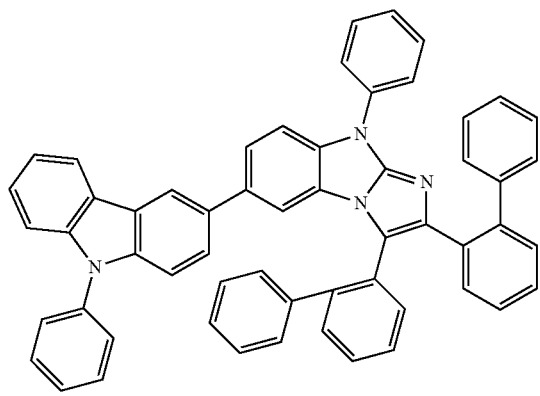 [SMILES: c1ccc(-c2ccccc2-c2nc3n(-c4ccccc4)c4ccc(-c5ccc6c(c5)c5ccccc5n6-c5ccccc5)cc4n3c2-c2ccccc2-c2ccccc2)cc1]
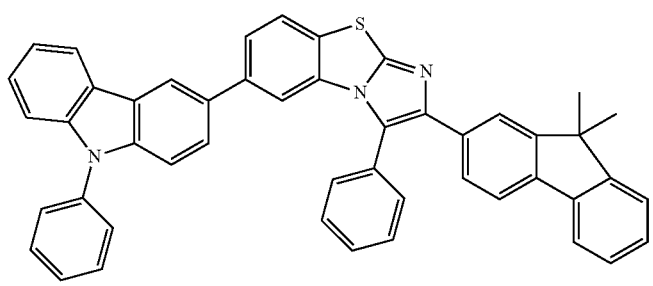 [SMILES: CC1(C)c2ccccc2-c2ccc(-c3nc4sc5ccc(-c6ccc7c(c6)c6ccccc6n7-c6ccccc6)cc5n4c3-c3ccccc3)cc21]
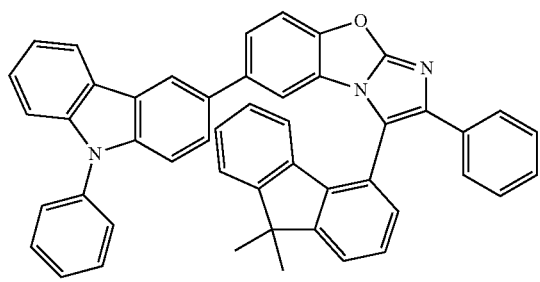 [SMILES: CC1(C)c2ccccc2-c2c(-c3c(-c4ccccc4)nc4oc5ccc(-c6ccc7c(c6)c6ccccc6n7-c6ccccc6)cc5n34)cccc21]
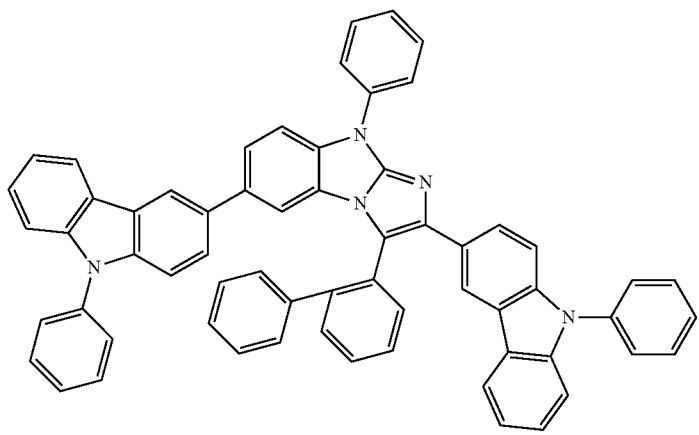 [SMILES: c1ccc(-c2ccccc2-c2c(-c3ccc4c(c3)c3ccccc3n4-c3ccccc3)nc3n(-c4ccccc4)c4ccc(-c5ccc6c(c5)c5ccccc5n6-c5ccccc5)cc4n23)cc1]

-continued
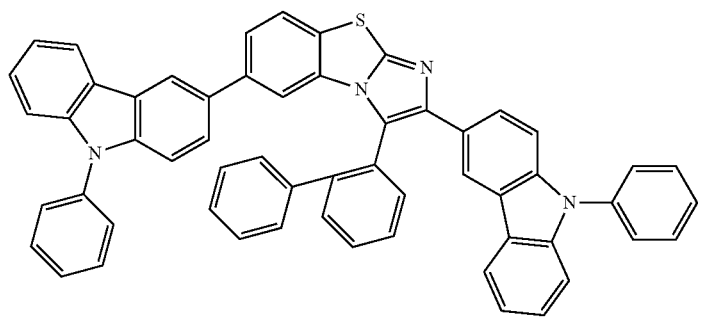 [SMILES: c1ccc(-c2ccccc2-c2c(-c3ccc4c(c3)c3ccccc3n4-c3ccccc3)nc3sc4ccc(-c5ccc6c(c5)c5ccccc5n6-c5ccccc5)cc4n23)cc1]
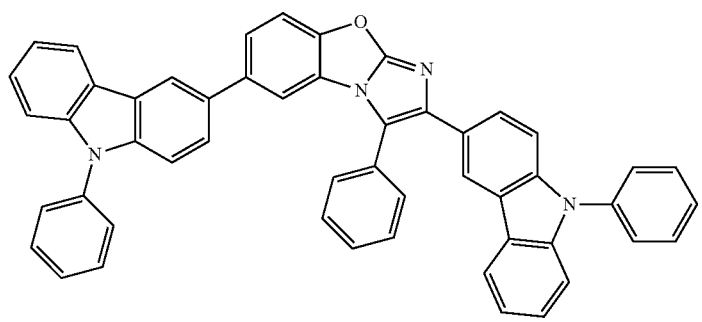 [SMILES: c1ccc(-c2c(-c3ccc4c(c3)c3ccccc3n4-c3ccccc3)nc3oc4ccc(-c5ccc6c(c5)c5ccccc5n6-c5ccccc5)cc4n23)cc1]
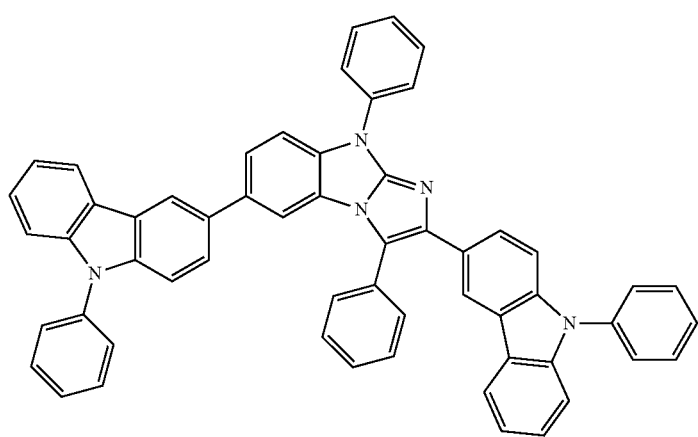 [SMILES: c1ccc(-c2c(-c3ccc4c(c3)c3ccccc3n4-c3ccccc3)nc3n(-c4ccccc4)c4ccc(-c5ccc6c(c5)c5ccccc5n6-c5ccccc5)cc4n23)cc1]
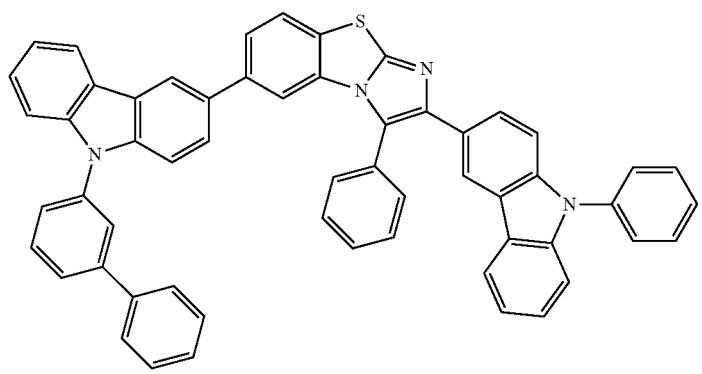 [SMILES: c1ccc(-c2cccc(-n3c4ccccc4c4cc(-c5ccc6sc7nc(-c8ccc9c(c8)c8ccccc8n9-c8ccccc8)c(-c8ccccc8)n7c6c5)ccc43)c2)cc1]

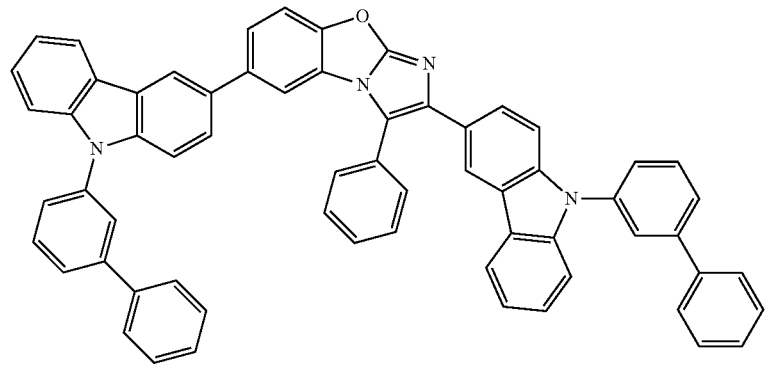 [SMILES: c1ccc(-c2cccc(-n3c4ccccc4c4cc(-c5ccc6oc7nc(-c8ccc9c(c8)c8ccccc8n9-c8cccc(-c9ccccc9)c8)c(-c8ccccc8)n7c6c5)ccc43)c2)cc1]
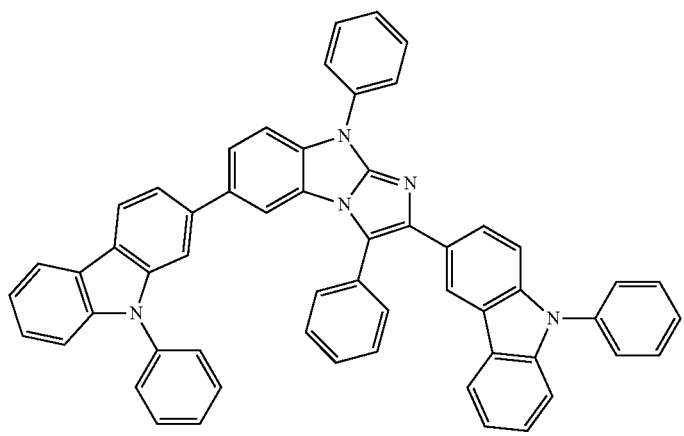 [SMILES: c1ccc(-c2c(-c3ccc4c(c3)c3ccccc3n4-c3ccccc3)nc3n(-c4ccccc4)c4ccc(-c5ccc6c7ccccc7n(-c7ccccc7)c6c5)cc4n23)cc1]
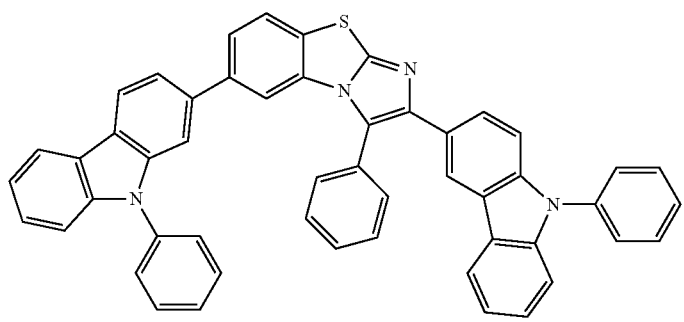 [SMILES: c1ccc(-c2c(-c3ccc4c(c3)c3ccccc3n4-c3ccccc3)nc3sc4ccc(-c5ccc6c7ccccc7n(-c7ccccc7)c6c5)cc4n23)cc1]
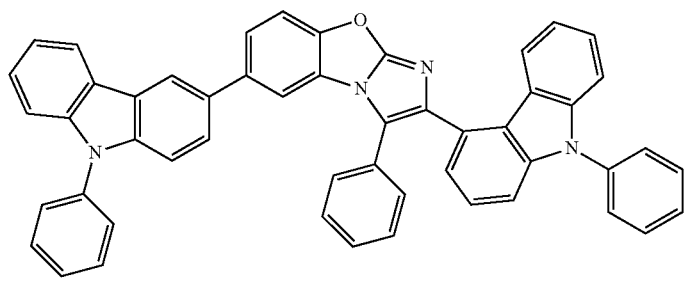 [SMILES: c1ccc(-c2c(-c3cccc4c3c3ccccc3n4-c3ccccc3)nc3oc4ccc(-c5ccc6c(c5)c5ccccc5n6-c5ccccc5)cc4n23)cc1]

-continued
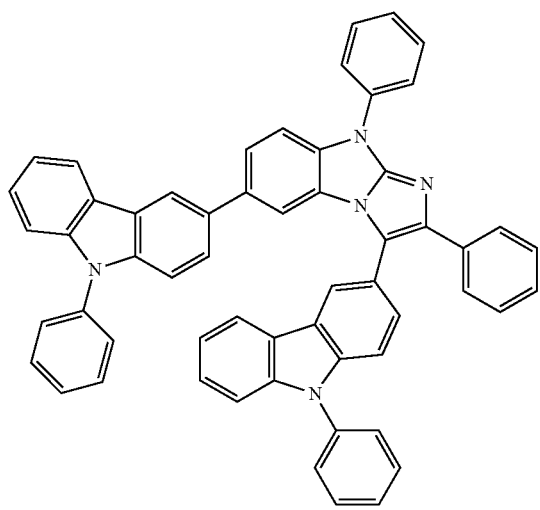 [SMILES: c1ccc(-c2nc3n(-c4ccccc4)c4ccc(-c5ccc6c(c5)c5ccccc5n6-c5ccccc5)cc4n3c2-c2ccc3c(c2)c2ccccc2n3-c2ccccc2)cc1]
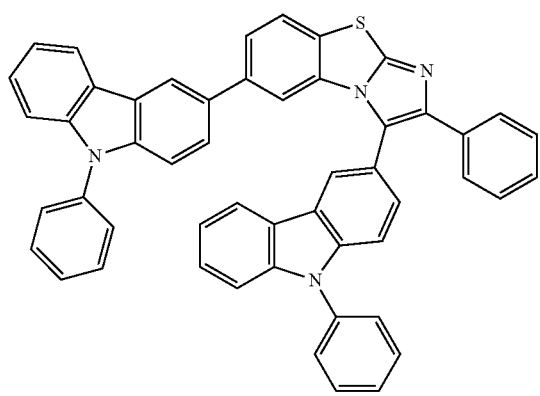 [SMILES: c1ccc(-c2nc3oc4ccc(-c5ccc6c(c5)c5ccccc5n6-c5ccccc5)cc4n3c2-c2ccc3c(c2)c2ccccc2n3-c2ccccc2)cc1]
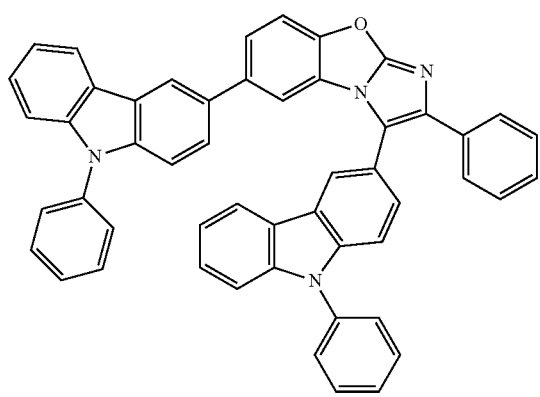

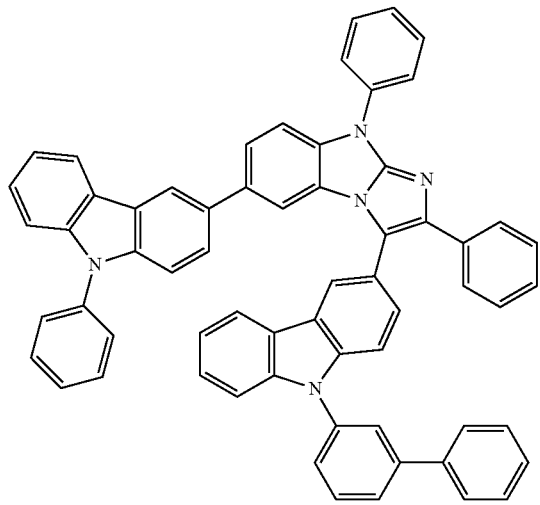 [SMILES: c1ccc(-c2cccc(-n3c4ccccc4c4cc(-c5c(-c6ccccc6)nc6n(-c7ccccc7)c7ccc(-c8ccc9c(c8)c8ccccc8n9-c8ccccc8)cc7n56)ccc43)c2)cc1]
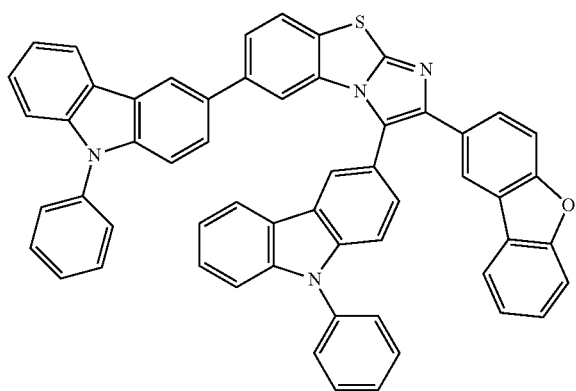 [SMILES: c1ccc(-n2c3ccccc3c3cc(-c4ccc5sc6nc(-c7ccc8oc9ccccc9c8c7)c(-c7ccc8c(c7)c7ccccc7n8-c7ccccc7)n6c5c4)ccc32)cc1]
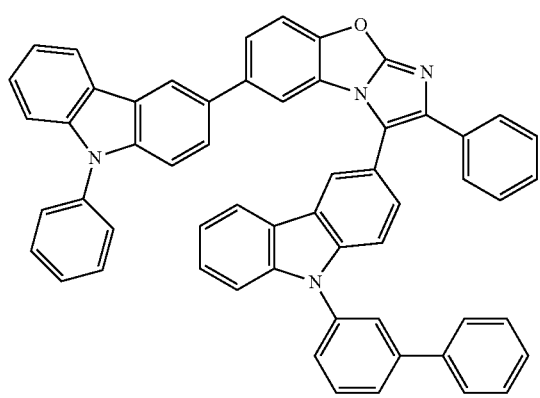 [SMILES: c1ccc(-c2cccc(-n3c4ccccc4c4cc(-c5c(-c6ccccc6)nc6oc7ccc(-c8ccc9c(c8)c8ccccc8n9-c8ccccc8)cc7n56)ccc43)c2)cc1]

-continued
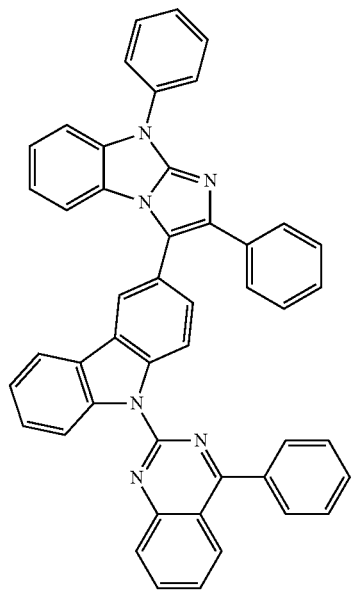 [SMILES: c1ccc(-c2nc3n(-c4ccccc4)c4ccccc4n3c2-c2ccc3c(c2)c2ccccc2n3-c2nc(-c3ccccc3)c3ccccc3n2)cc1]
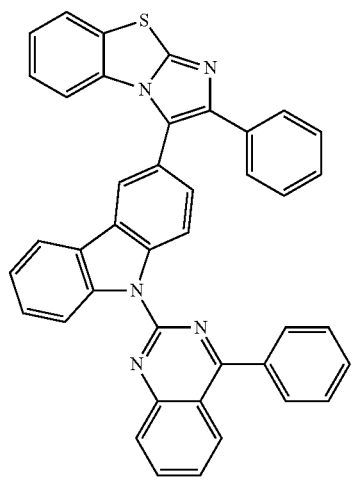 [SMILES: c1ccc(-c2nc3sc4ccccc4n3c2-c2ccc3c(c2)c2ccccc2n3-c2nc(-c3ccccc3)c3ccccc3n2)cc1]
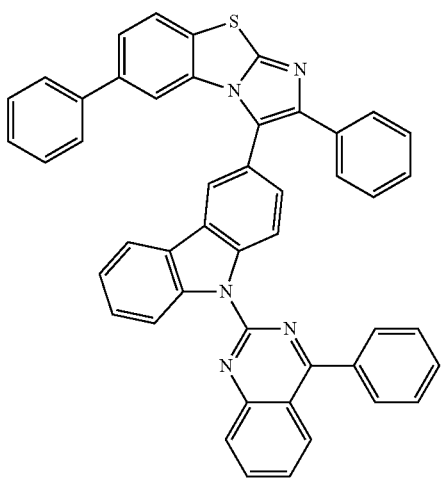 [SMILES: c1ccc(-c2ccc3sc4nc(-c5ccccc5)c(-c5ccc6c(c5)c5ccccc5n6-c5nc(-c6ccccc6)c6ccccc6n5)n4c3c2)cc1]

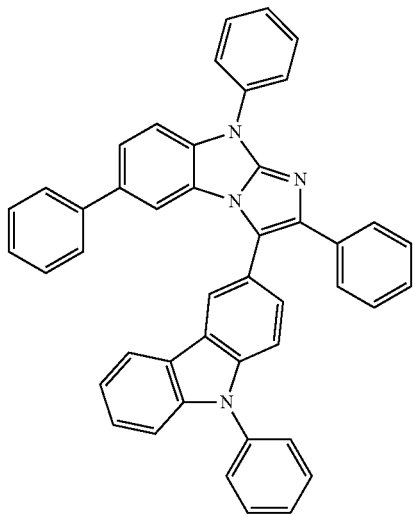 [SMILES: c1ccc(-c2ccc3c(c2)n2c(-c4ccc5c(c4)c4ccccc4n5-c4ccccc4)c(-c4ccccc4)nc2n3-c2ccccc2)cc1]
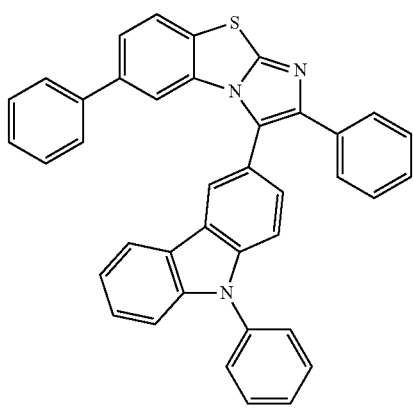 [SMILES: c1ccc(-c2ccc3sc4nc(-c5ccccc5)c(-c5ccc6c(c5)c5ccccc5n6-c5ccccc5)n4c3c2)cc1]
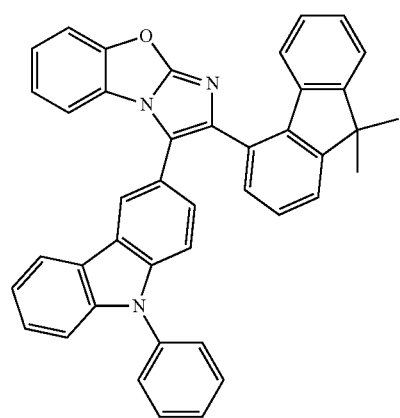 [SMILES: CC1(C)c2ccccc2-c2c(-c3nc4oc5ccccc5n4c3-c3ccc4c(c3)c3ccccc3n4-c3ccccc3)cccc21]

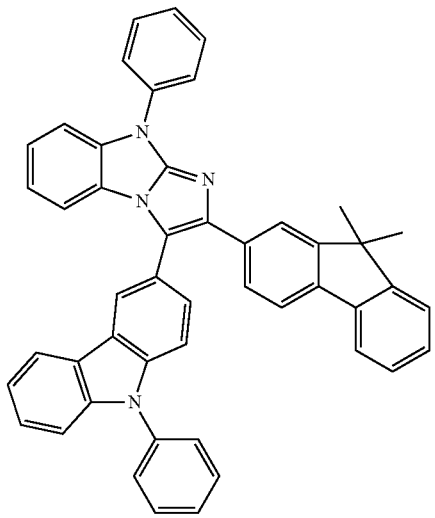 [SMILES: CC1(C)c2ccccc2-c2ccc(-c3nc4n(-c5ccccc5)c5ccccc5n4c3-c3ccc4c(c3)c3ccccc3n4-c3ccccc3)cc21]
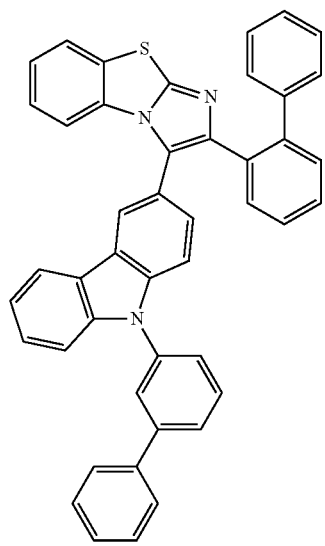 [SMILES: c1ccc(-c2cccc(-n3c4ccccc4c4cc(-c5c(-c6ccccc6-c6ccccc6)nc6sc7ccccc7n56)ccc43)c2)cc1]
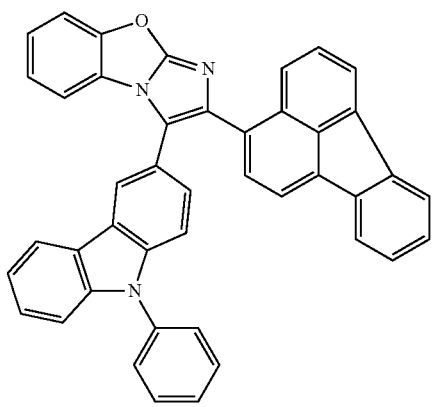 [SMILES: c1ccc(-n2c3ccccc3c3cc(-c4c(-c5ccc6c7c(cccc57)-c5ccccc5-6)nc5oc6ccccc6n45)ccc32)cc1]

-continued
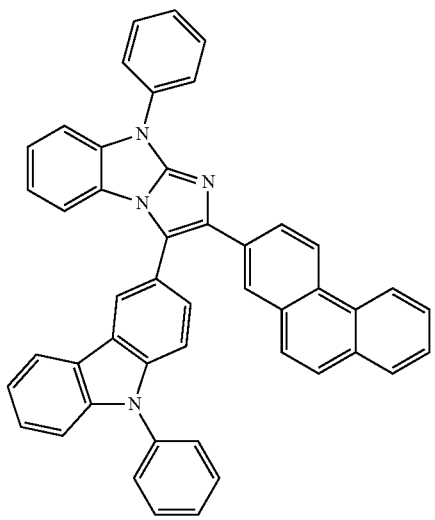 [SMILES: c1ccc(-n2c3ccccc3c3cc(-c4c(-c5ccc6c(ccc7ccccc76)c5)nc5n(-c6ccccc6)c6ccccc6n45)ccc32)cc1]
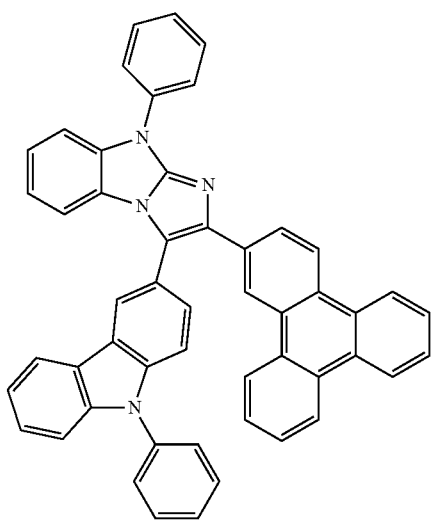 [SMILES: c1ccc(-n2c3ccccc3c3cc(-c4c(-c5ccc6c7ccccc7c7ccccc7c6c5)nc5n(-c6ccccc6)c6ccccc6n45)ccc32)cc1]
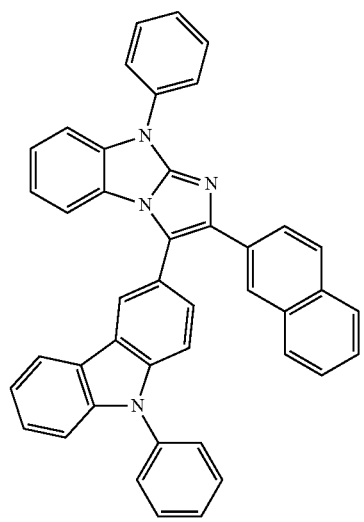 [SMILES: c1ccc(-n2c3ccccc3c3cc(-c4c(-c5ccc6ccccc6c5)nc5n(-c6ccccc6)c6ccccc6n45)ccc32)cc1]

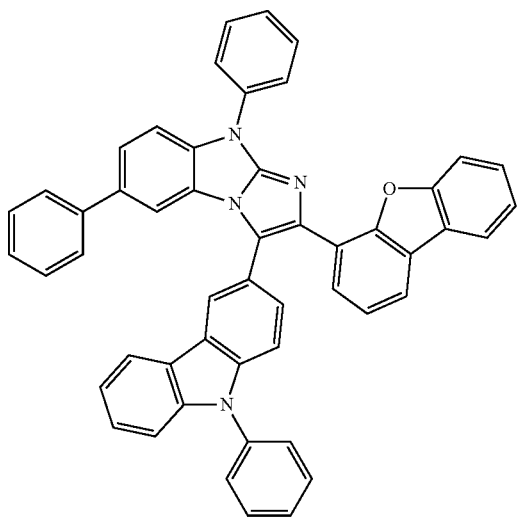 [SMILES: c1ccc(-c2ccc3c(c2)n2c(-c4ccc5c(c4)c4ccccc4n5-c4ccccc4)c(-c4cccc5c4oc4ccccc45)nc2n3-c2ccccc2)cc1]
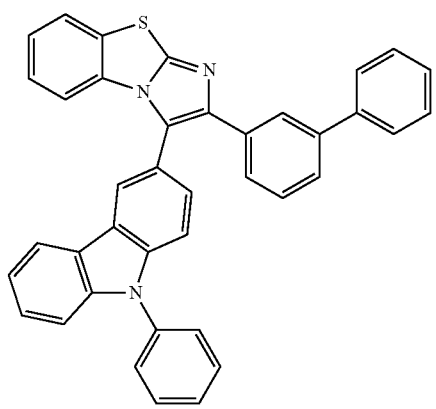 [SMILES: c1ccc(-c2cccc(-c3nc4sc5ccccc5n4c3-c3ccc4c(c3)c3ccccc3n4-c3ccccc3)c2)cc1]
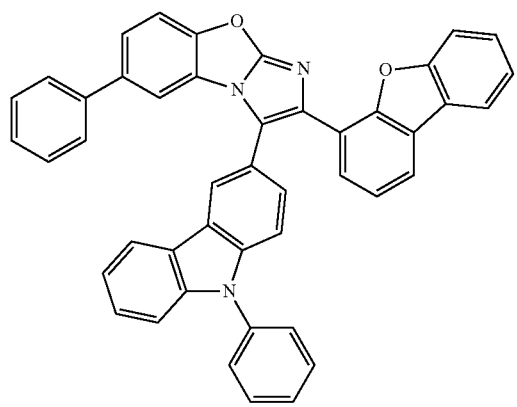 [SMILES: c1ccc(-c2ccc3oc4nc(-c5cccc6c5oc5ccccc56)c(-c5ccc6c(c5)c5ccccc5n6-c5ccccc5)n4c3c2)cc1]

-continued
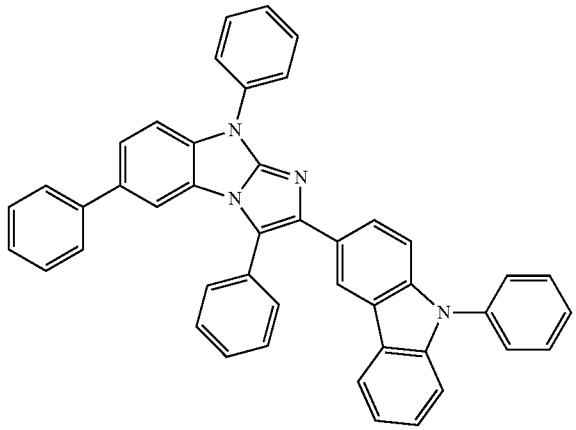 [SMILES: c1ccc(-c2ccc3c(c2)n2c(-c4ccccc4)c(-c4ccc5c(c4)c4ccccc4n5-c4ccccc4)nc2n3-c2ccccc2)cc1]
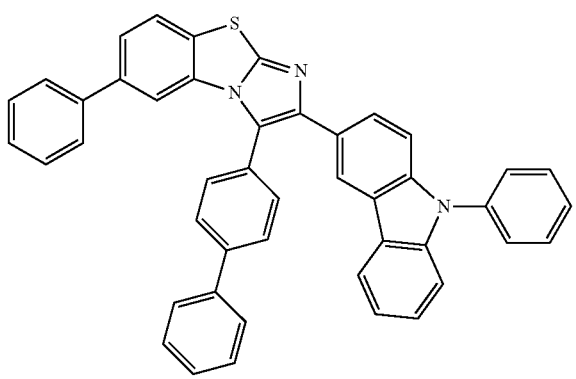 [SMILES: c1ccc(-c2ccc(-c3c(-c4ccc5c(c4)c4ccccc4n5-c4ccccc4)nc4sc5ccc(-c6ccccc6)cc5n34)cc2)cc1]
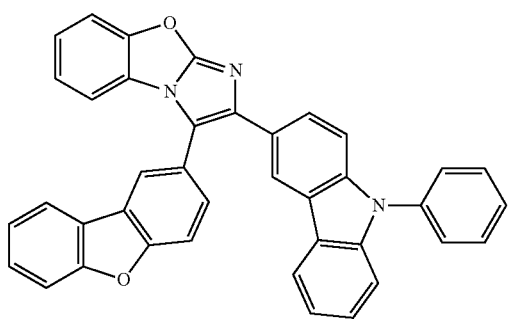 [SMILES: c1ccc(-n2c3ccccc3c3cc(-c4nc5oc6ccccc6n5c4-c4ccc5oc6ccccc6c5c4)ccc32)cc1]
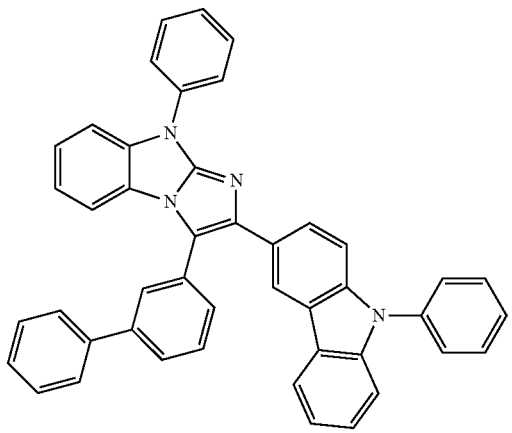 [SMILES: c1ccc(-c2cccc(-c3c(-c4ccc5c(c4)c4ccccc4n5-c4ccccc4)nc4n(-c5ccccc5)c5ccccc5n34)c2)cc1]

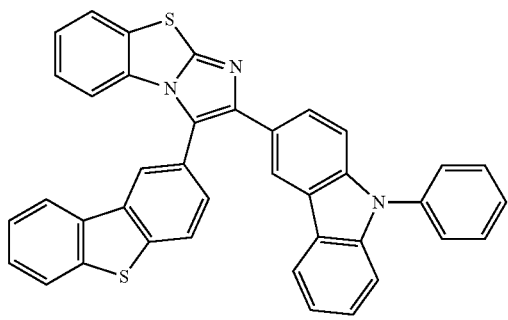
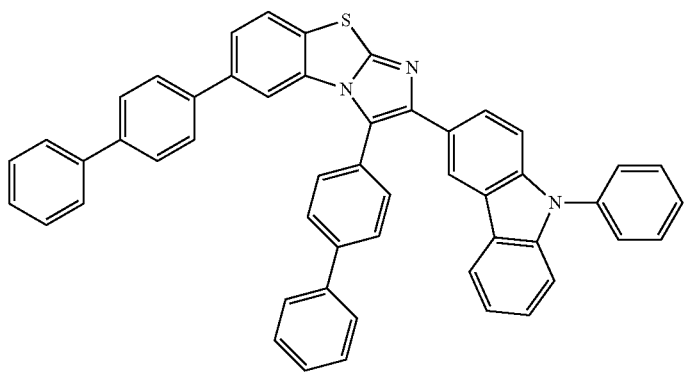 [SMILES: c1ccc(-c2ccc(-c3ccc4sc5nc(-c6ccc7c(c6)c6ccccc6n7-c6ccccc6)c(-c6ccc(-c7ccccc7)cc6)n5c4c3)cc2)cc1]
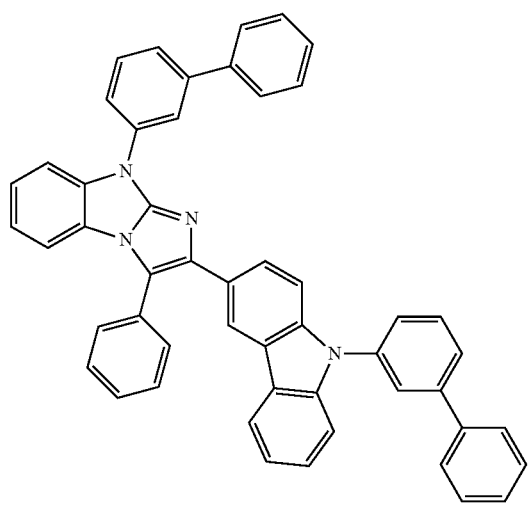 [SMILES: c1ccc(-c2cccc(-n3c4ccccc4c4cc(-c5nc6n(-c7cccc(-c8ccccc8)c7)c7ccccc7n6c5-c5ccccc5)ccc43)c2)cc1]

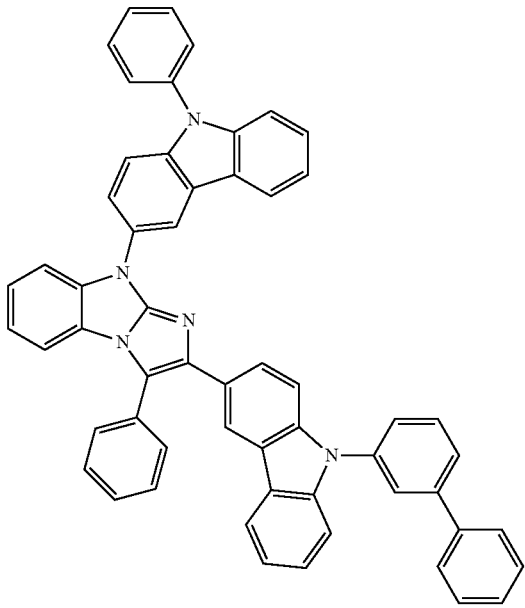 [SMILES: c1ccc(-c2cccc(-n3c4ccccc4c4cc(-c5nc6n(-c7ccc8c(c7)c7ccccc7n8-c7ccccc7)c7ccccc7n6c5-c5ccccc5)ccc43)c2)cc1]
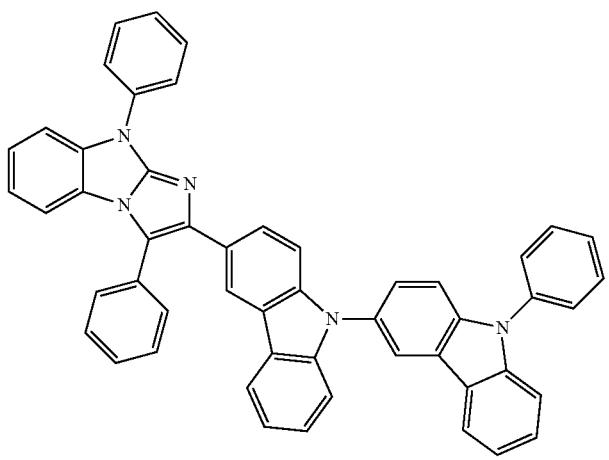 [SMILES: c1ccc(-c2c(-c3ccc4c(c3)c3ccccc3n4-c3ccc4c(c3)c3ccccc3n4-c3ccccc3)nc3n(-c4ccccc4)c4ccccc4n23)cc1]
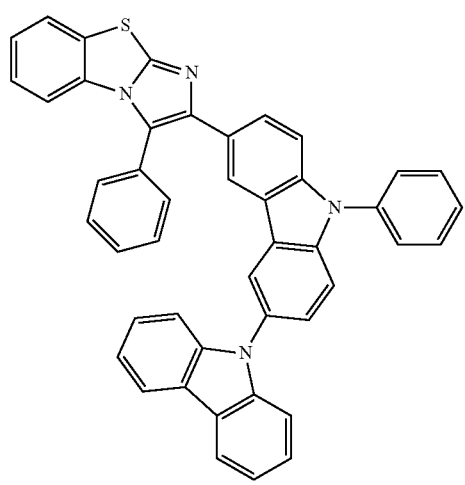 [SMILES: c1ccc(-c2c(-c3ccc4c(c3)c3cc(-n5c6ccccc6c6ccccc65)ccc3n4-c3ccccc3)nc3sc4ccccc4n23)cc1]

-continued
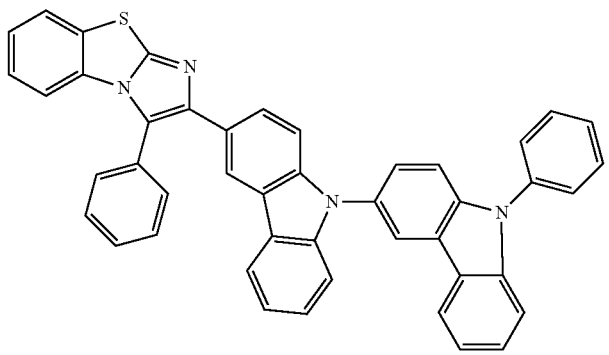 [SMILES: c1ccc(-c2c(-c3ccc4c(c3)c3ccccc3n4-c3ccc4c(c3)c3ccccc3n4-c3ccccc3)nc3sc4ccccc4n23)cc1]
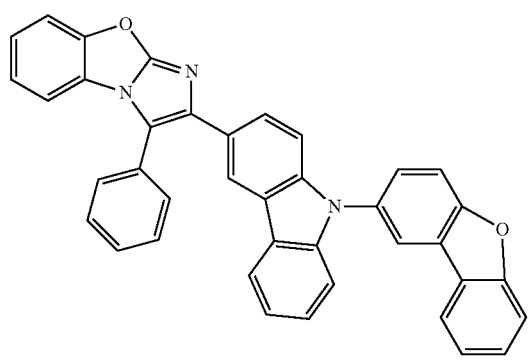 [SMILES: c1ccc(-c2c(-c3ccc4c(c3)c3ccccc3n4-c3ccc4oc5ccccc5c4c3)nc3oc4ccccc4n23)cc1]
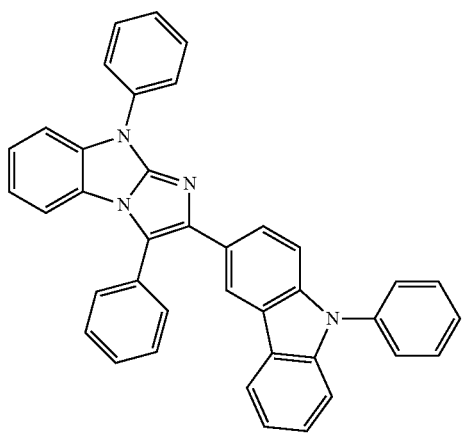 [SMILES: c1ccc(-c2c(-c3ccc4c(c3)c3ccccc3n4-c3ccccc3)nc3n(-c4ccccc4)c4ccccc4n23)cc1]
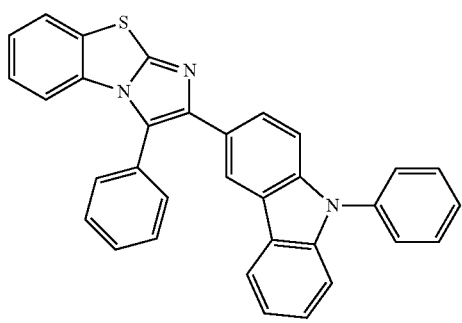 [SMILES: c1ccc(-c2c(-c3ccc4c(c3)c3ccccc3n4-c3ccccc3)nc3oc4ccccc4n23)cc1]

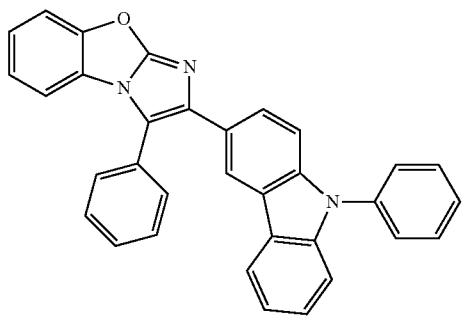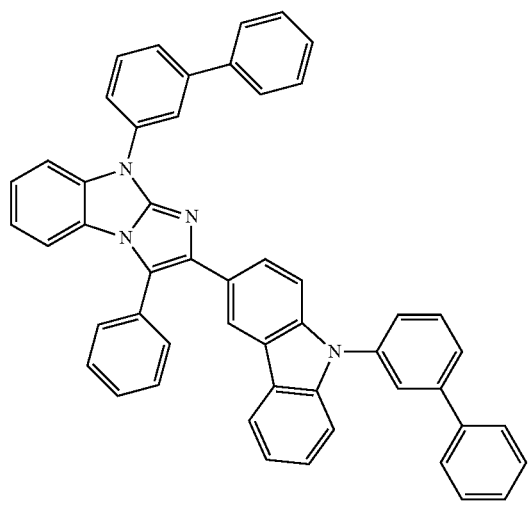 [SMILES: c1ccc(-c2cccc(-n3c4ccccc4c4cc(-c5nc6n(-c7cccc(-c8ccccc8)c7)c7ccccc7n6c5-c5ccccc5)ccc43)c2)cc1]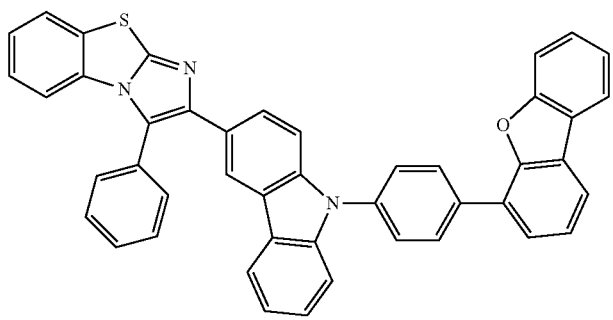 [SMILES: c1ccc(-c2c(-c3ccc4c(c3)c3ccccc3n4-c3ccc(-c4cccc5c4oc4ccccc45)cc3)nc3sc4ccccc4n23)cc1]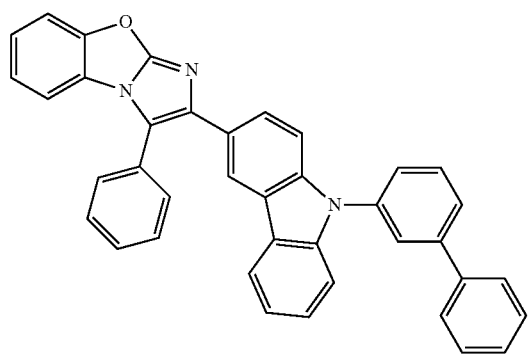 [SMILES: c1ccc(-c2cccc(-n3c4ccccc4c4cc(-c5nc6oc7ccccc7n6c5-c5ccccc5)ccc43)c2)cc1]

-continued
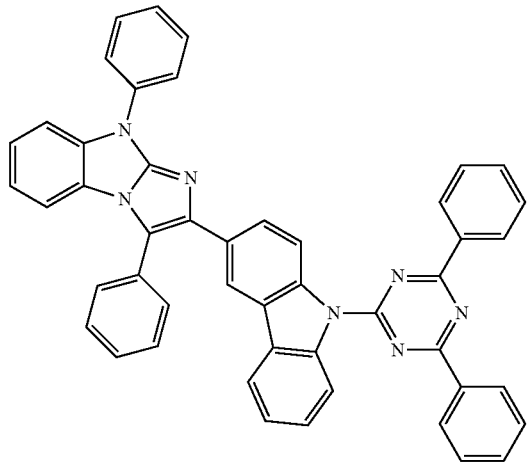 [SMILES: c1ccc(-c2nc(-c3ccccc3)nc(-n3c4ccccc4c4cc(-c5nc6n(-c7ccccc7)c7ccccc7n6c5-c5ccccc5)ccc43)n2)cc1]
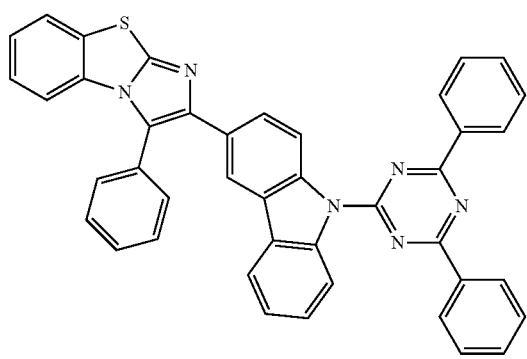
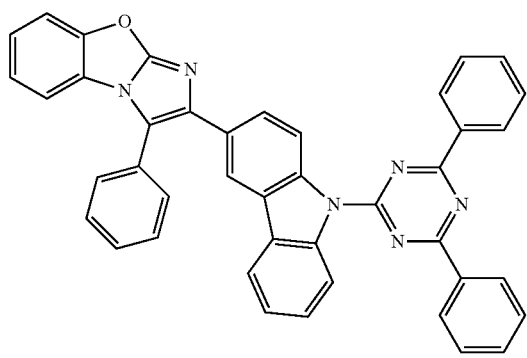 [SMILES: c1ccc(-c2nc(-c3ccccc3)nc(-n3c4ccccc4c4cc(-c5nc6oc7ccccc7n6c5-c5ccccc5)ccc43)n2)cc1]
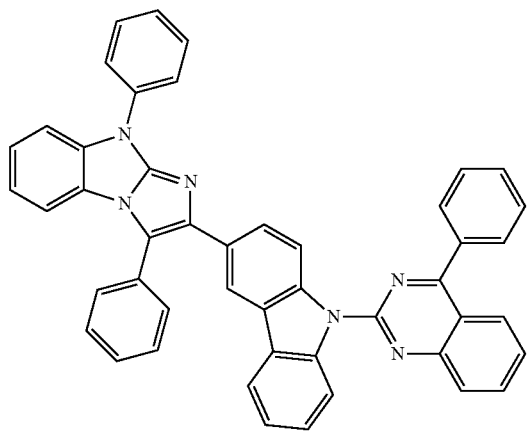 [SMILES: c1ccc(-c2nc(-n3c4ccccc4c4cc(-c5nc6n(-c7ccccc7)c7ccccc7n6c5-c5ccccc5)ccc43)nc3ccccc23)cc1]

-continued
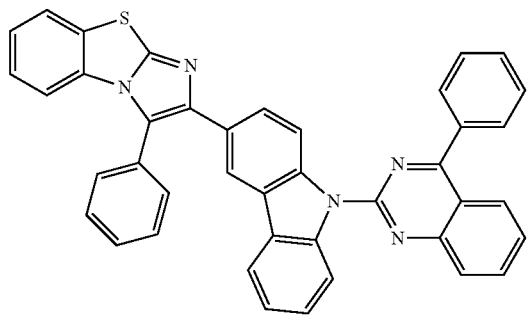 [SMILES: c1ccc(-c2nc(-n3c4ccccc4c4cc(-c5nc6sc7ccccc7n6c5-c5ccccc5)ccc43)nc3ccccc23)cc1]

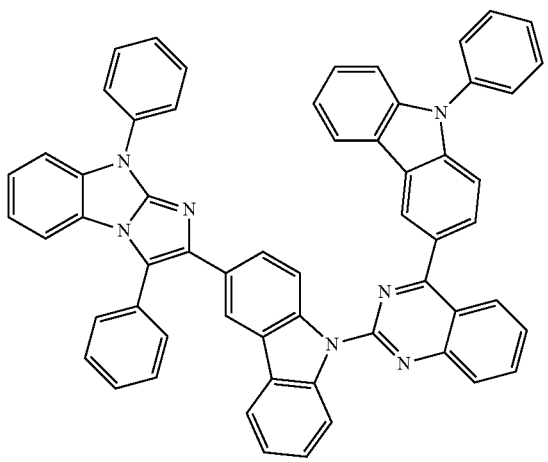 [SMILES: c1ccc(-c2c(-c3ccc4c(c3)c3ccccc3n4-c3nc(-c4ccc5c(c4)c4ccccc4n5-c4ccccc4)c4ccccc4n3)nc3n(-c4ccccc4)c4ccccc4n23)cc1]
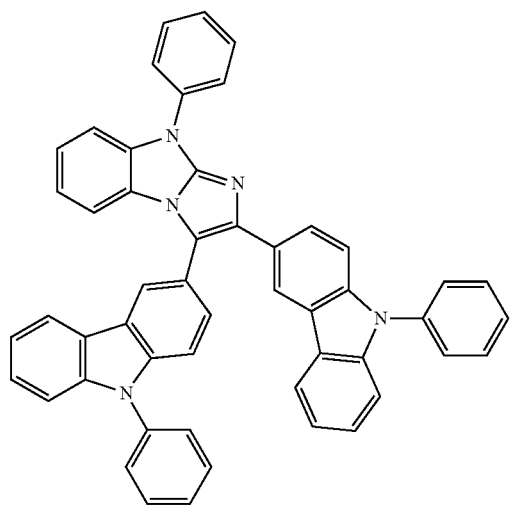 [SMILES: c1ccc(-n2c3ccccc3c3cc(-c4nc5n(-c6ccccc6)c6ccccc6n5c4-c4ccc5c(c4)c4ccccc4n5-c4ccccc4)ccc32)cc1]
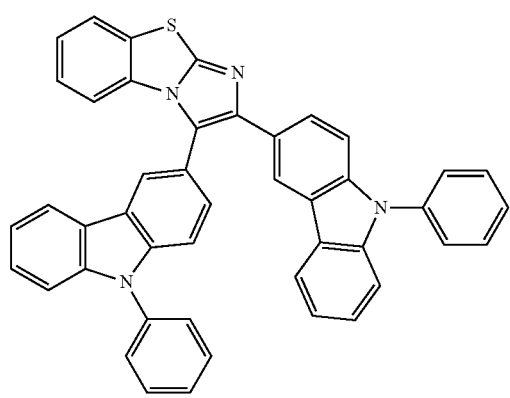 [SMILES: c1ccc(-n2c3ccccc3c3cc(-c4nc5sc6ccccc6n5c4-c4ccc5c(c4)c4ccccc4n5-c4ccccc4)ccc32)cc1]

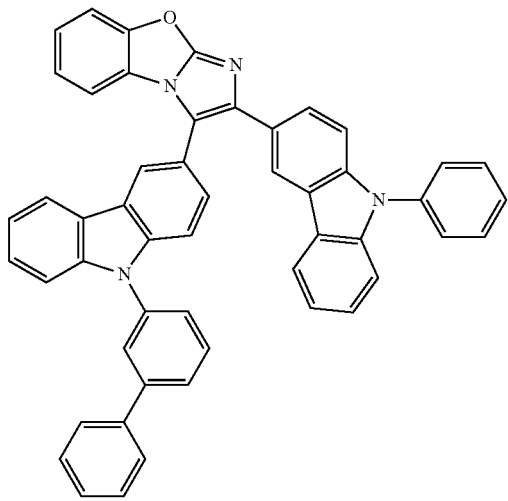 [SMILES: c1ccc(-c2cccc(-n3c4ccccc4c4cc(-c5c(-c6ccc7c(c6)c6ccccc6n7-c6ccccc6)nc6oc7ccccc7n56)ccc43)c2)cc1]
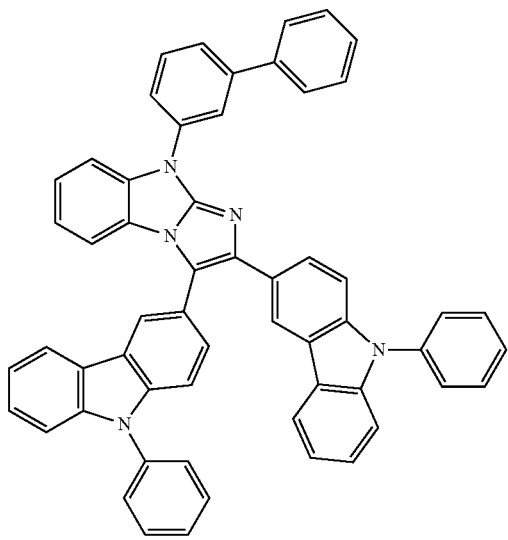 [SMILES: c1ccc(-c2cccc(-n3c4ccccc4n4c(-c5ccc6c(c5)c5ccccc5n6-c5ccccc5)c(-c5ccc6c(c5)c5ccccc5n6-c5ccccc5)nc34)c2)cc1]
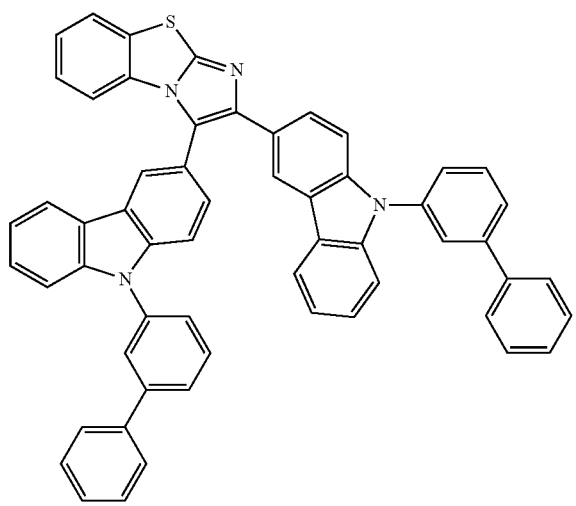 [SMILES: c1ccc(-c2cccc(-n3c4ccccc4c4cc(-c5nc6sc7ccccc7n6c5-c5ccc6c(c5)c5ccccc5n6-c5cccc(-c6ccccc6)c5)ccc43)c2)cc1]

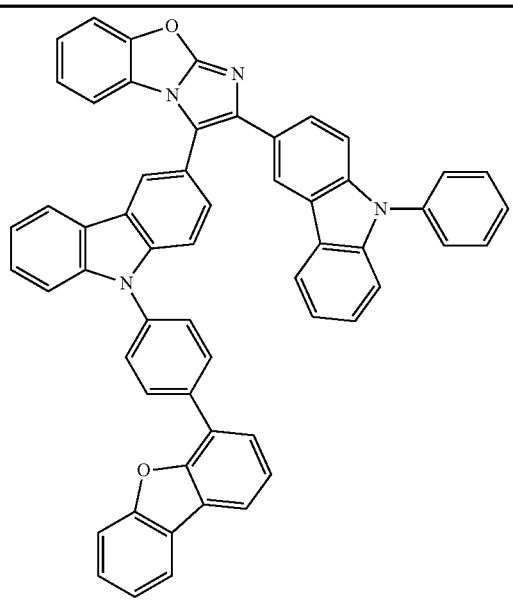
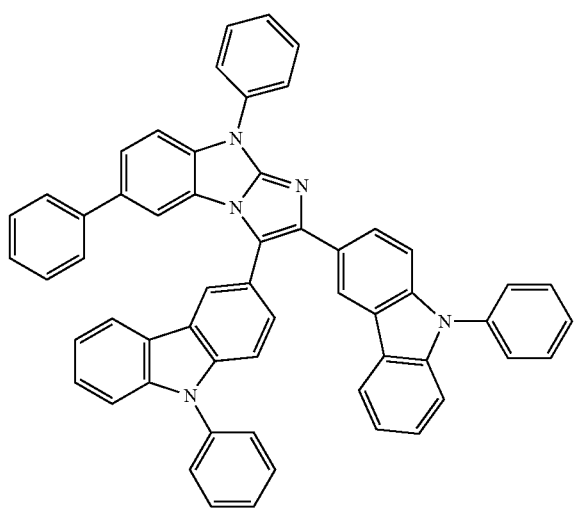 [SMILES: c1ccc(-c2ccc3c(c2)n2c(-c4ccc5c(c4)c4ccccc4n5-c4ccccc4)c(-c4ccc5c(c4)c4ccccc4n5-c4ccccc4)nc2n3-c2ccccc2)cc1]
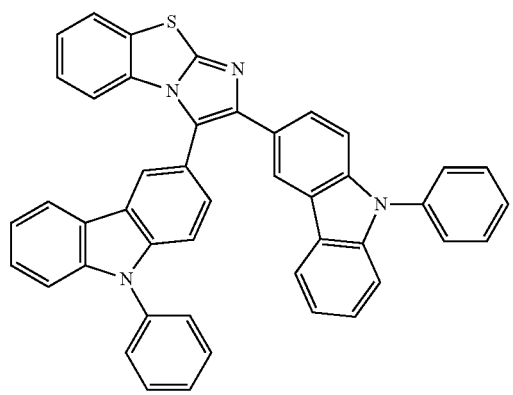 [SMILES: c1ccc(-n2c3ccccc3c3cc(-c4nc5sc6ccccc6n5c4-c4ccc5c(c4)c4ccccc4n5-c4ccccc4)ccc32)cc1]

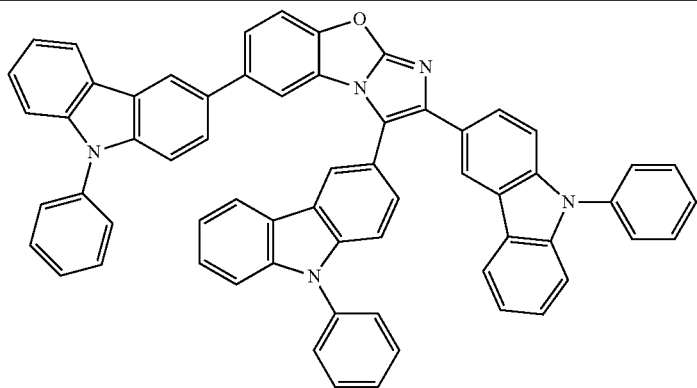
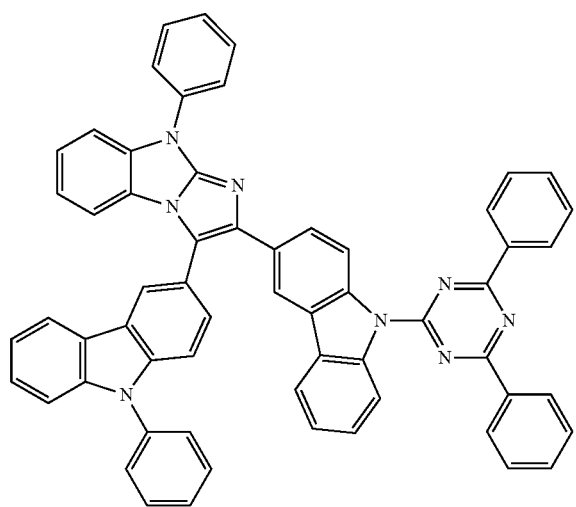 [SMILES: c1ccc(-c2nc(-c3ccccc3)nc(-n3c4ccccc4c4cc(-c5nc6n(-c7ccccc7)c7ccccc7n6c5-c5ccc6c(c5)c5ccccc5n6-c5ccccc5)ccc43)n2)cc1]
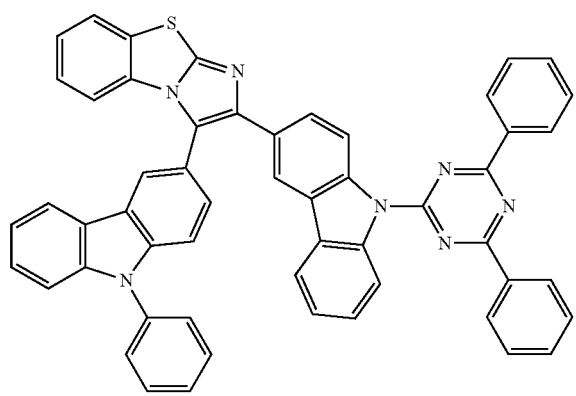 [SMILES: c1ccc(-c2nc(-c3ccccc3)nc(-n3c4ccccc4c4cc(-c5nc6oc7ccccc7n6c5-c5ccc6c(c5)c5ccccc5n6-c5ccccc5)ccc43)n2)cc1]

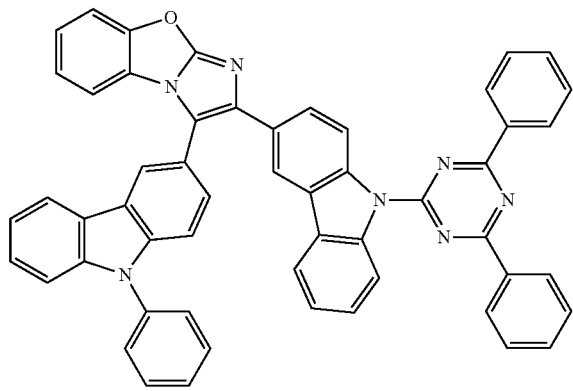
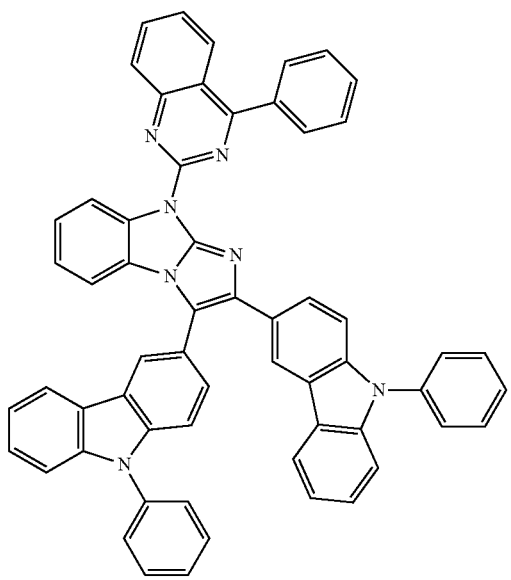 [SMILES: c1ccc(-c2nc(-n3c4ccccc4n4c(-c5ccc6c(c5)c5ccccc5n6-c5ccccc5)c(-c5ccc6c(c5)c5ccccc5n6-c5ccccc5)nc34)nc3ccccc23)cc1]
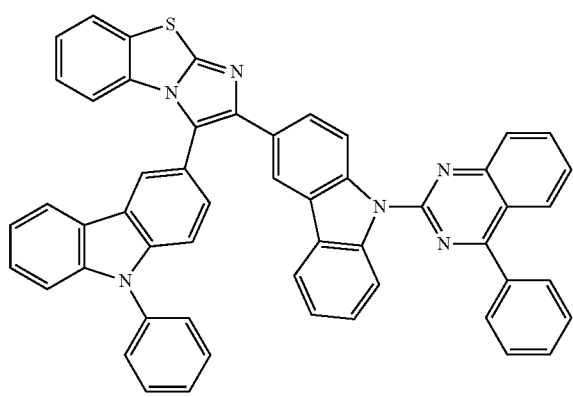 [SMILES: c1ccc(-c2nc(-n3c4ccccc4c4cc(-c5nc6sc7ccccc7n6c5-c5ccc6c(c5)c5ccccc5n6-c5ccccc5)ccc43)nc3ccccc23)cc1]

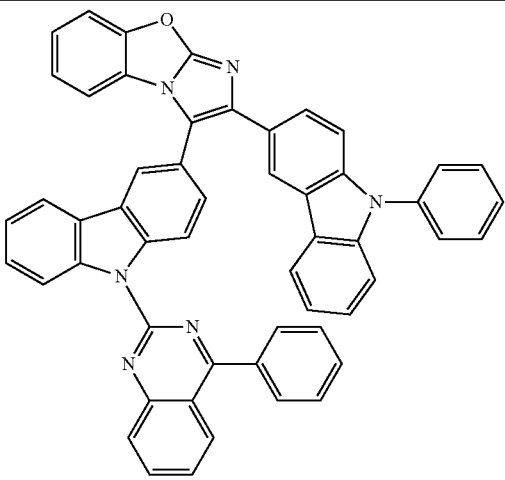
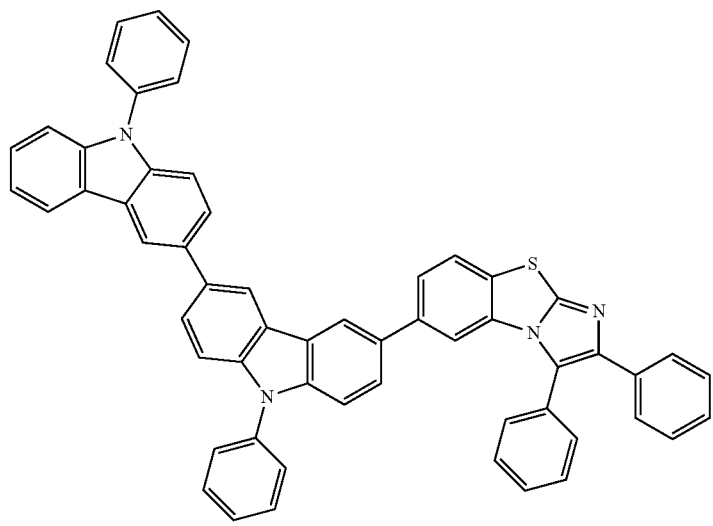 [SMILES: c1ccc(-c2nc3sc4ccc(-c5ccc6c(c5)c5cc(-c7ccc8c(c7)c7ccccc7n8-c7ccccc7)ccc5n6-c5ccccc5)cc4n3c2-c2ccccc2)cc1]
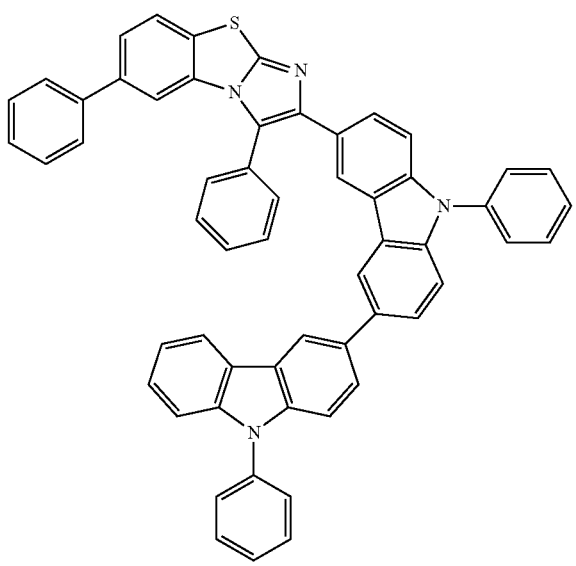 [SMILES: c1ccc(-c2ccc3sc4nc(-c5ccc6c(c5)c5cc(-c7ccc8c(c7)c7ccccc7n8-c7ccccc7)ccc5n6-c5ccccc5)c(-c5ccccc5)n4c3c2)cc1]

-continued
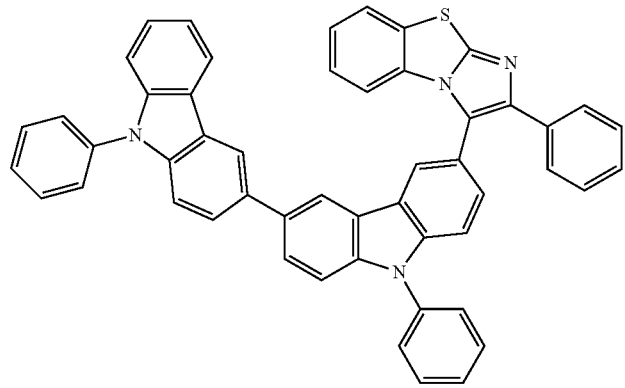 [SMILES: c1ccc(-c2nc3sc4ccccc4n3c2-c2ccc3c(c2)c2cc(-c4ccc5c(c4)c4ccccc4n5-c4ccccc4)ccc2n3-c2ccccc2)cc1]
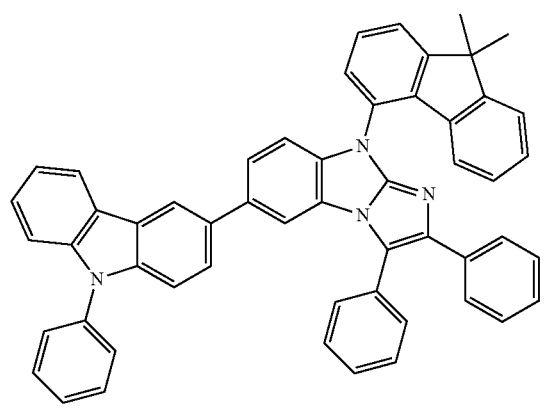 [SMILES: CC1(C)c2ccccc2-c2c(-n3c4ccc(-c5ccc6c(c5)c5ccccc5n6-c5ccccc5)cc4n4c(-c5ccccc5)c(-c5ccccc5)nc34)cccc21]
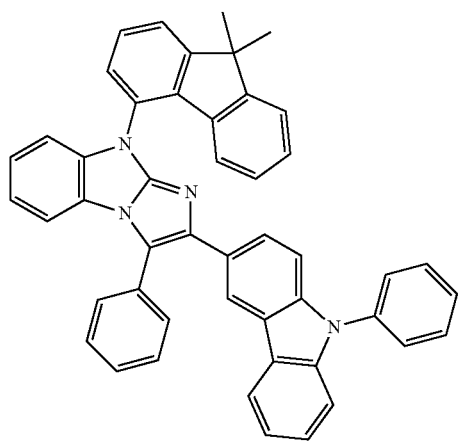 [SMILES: CC1(C)c2ccccc2-c2c(-n3c4ccccc4n4c(-c5ccccc5)c(-c5ccc6c(c5)c5ccccc5n6-c5ccccc5)nc34)cccc21]
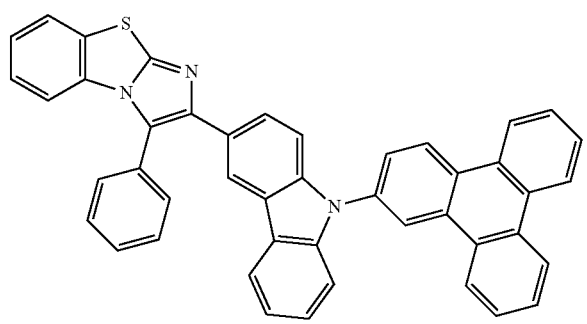 [SMILES: c1ccc(-c2c(-c3ccc4c(c3)c3ccccc3n4-c3ccc4c5ccccc5c5ccccc5c4c3)nc3sc4ccccc4n23)cc1]

-continued
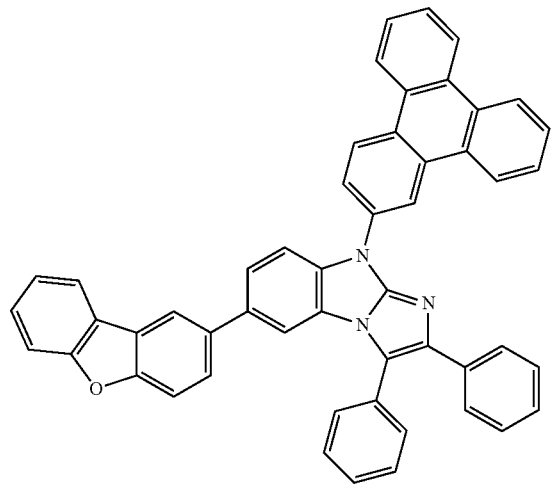 [SMILES: c1ccc(-c2nc3n(-c4ccc5c6ccccc6c6ccccc6c5c4)c4ccc(-c5ccc6oc7ccccc7c6c5)cc4n3c2-c2ccccc2)cc1]
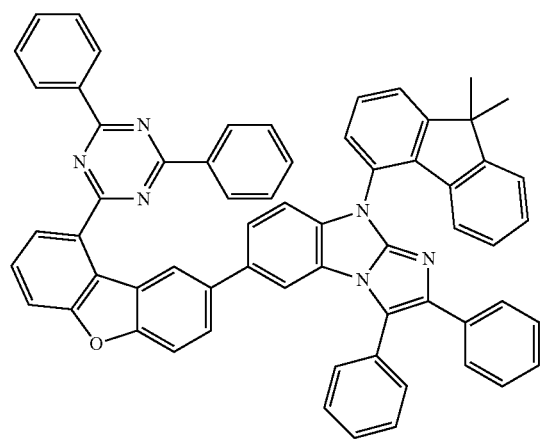 [SMILES: CC1(C)c2ccccc2-c2c(-n3c4ccc(-c5ccc6oc7cccc(-c8nc(-c9ccccc9)nc(-c9ccccc9)n8)c7c6c5)cc4n4c(-c5ccccc5)c(-c5ccccc5)nc34)cccc21]
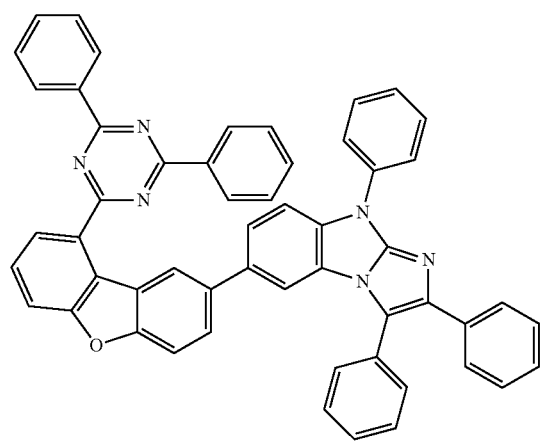 [SMILES: c1ccc(-c2nc(-c3ccccc3)nc(-c3cccc4oc5ccc(-c6ccc7c(c6)n6c(-c8ccccc8)c(-c8ccccc8)nc6n7-c6ccccc6)cc5c34)n2)cc1]

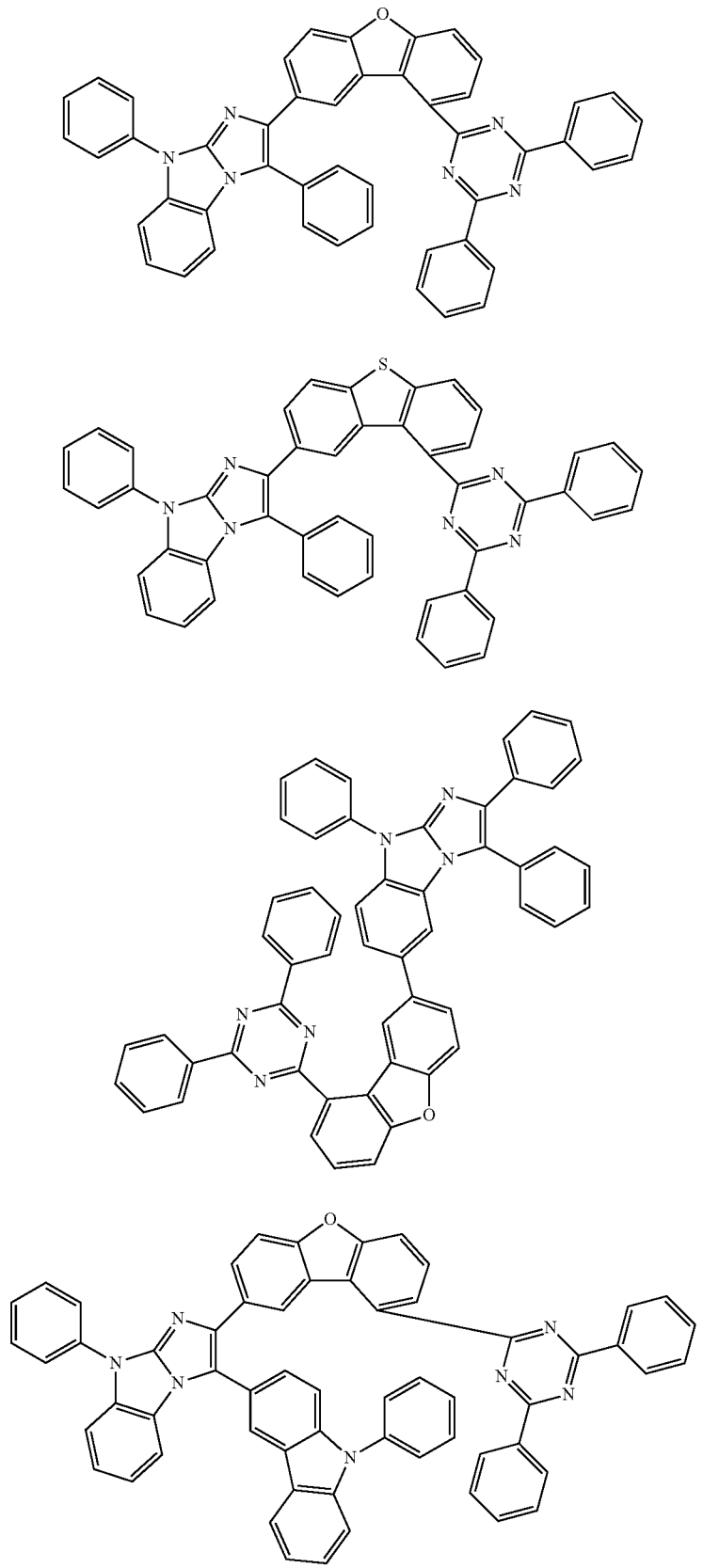

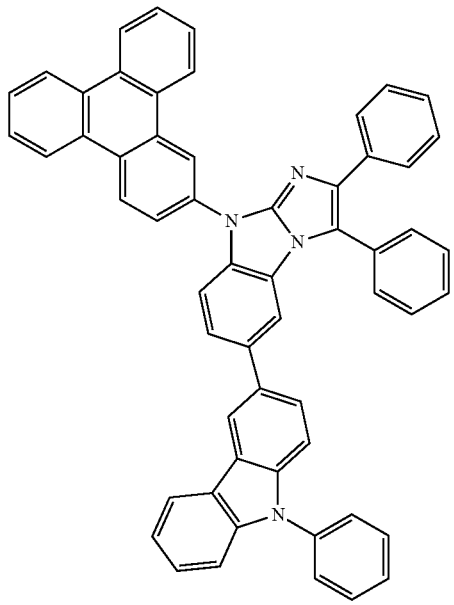 [SMILES: c1ccc(-c2nc3n(-c4ccc5c6ccccc6c6ccccc6c5c4)c4ccc(-c5ccc6c(c5)c5ccccc5n6-c5ccccc5)cc4n3c2-c2ccccc2)cc1]
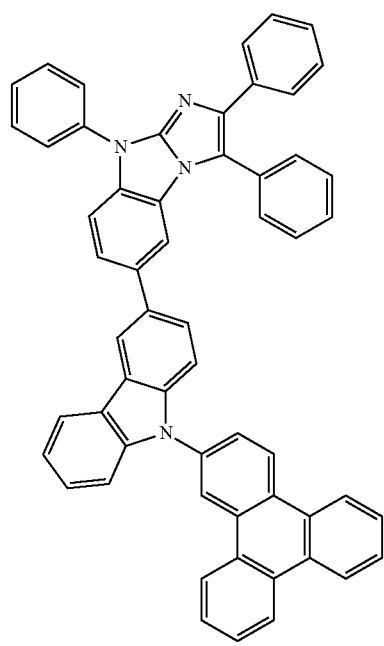 [SMILES: c1ccc(-c2nc3n(-c4ccccc4)c4ccc(-c5ccc6c(c5)c5ccccc5n6-c5ccc6c7ccccc7c7ccccc7c6c5)cc4n3c2-c2ccccc2)cc1]

-continued
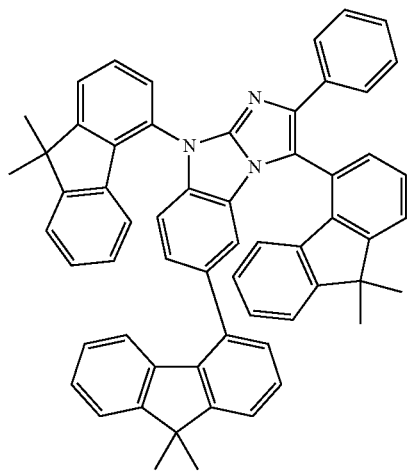 [SMILES: CC1(C)c2ccccc2-c2c(-c3ccc4c(c3)n3c(-c5cccc6c5-c5ccccc5C6(C)C)c(-c5ccccc5)nc3n4-c3cccc4c3-c3ccccc3C4(C)C)cccc21]
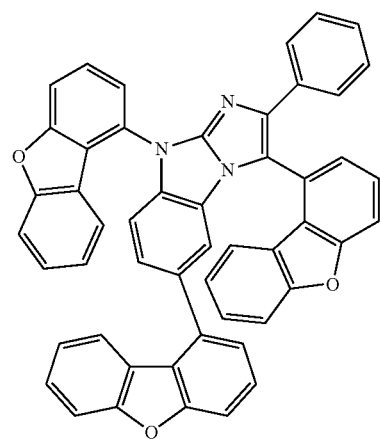 [SMILES: c1ccc(-c2nc3n(-c4cccc5oc6ccccc6c45)c4ccc(-c5cccc6oc7ccccc7c56)cc4n3c2-c2cccc3oc4ccccc4c23)cc1]
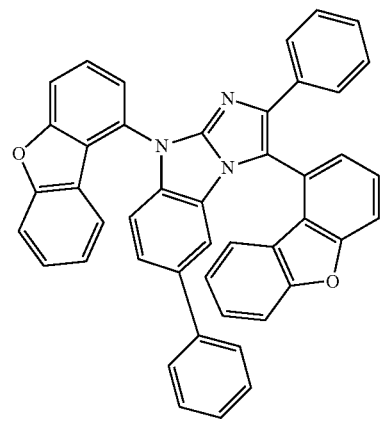 [SMILES: c1ccc(-c2ccc3c(c2)n2c(-c4cccc5oc6ccccc6c45)c(-c4ccccc4)nc2n3-c2cccc3oc4ccccc4c23)cc1]

The compounds according to the invention can be prepared by synthesis steps known to the person skilled in the art, such as, for example, bromination, Suzuki coupling, Ullmann coupling, Hartwig-Buchwald coupling, etc.

Suitable synthesis processes are depicted in general terms in Schemes 1 and 2 below.

Scheme 1—Synthesis Heterocycle (Int-1)

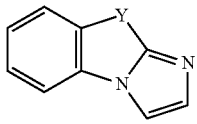

formula (Int-1)

Where Y is NAr$^N$, O or S and where the intermediate of formula (Int-1) may be substituted by a radical at any free position.

Intermediate of formula (Int-1) may be synthesized as follows:

Route 1:

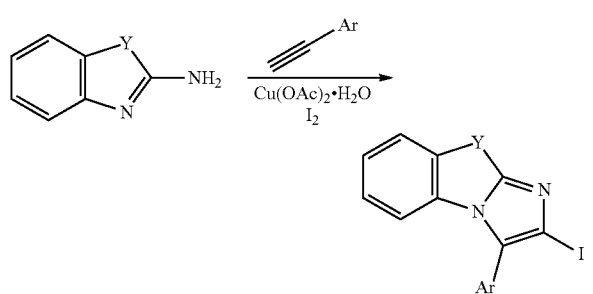

Such a synthesis is known from the literature (for example in Org. Biomol. Chem. 2016, 14, 5073-78)

Route 2:

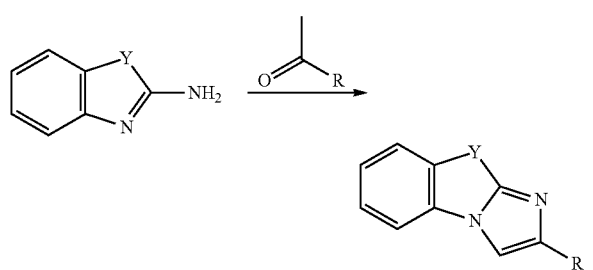

Such a synthesis pathway is known from the literature (for example in Org. Lett. Chem. 2014, 16, 6084)

Route 3:

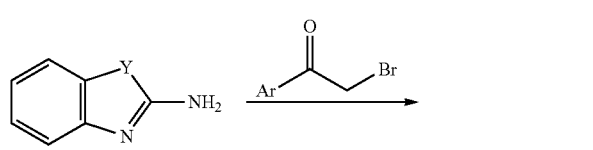

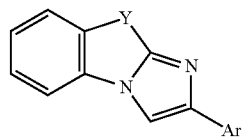

Such a synthesis pathway is known from the literature (for example in KR 2015034029).

Route 4:

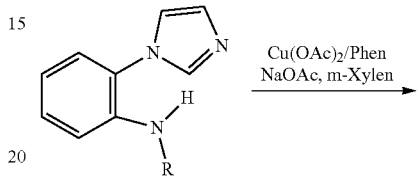

Such a synthesis pathway is known from the literature (for example in Org. Lett. 2012, 14(2), 452-55).

Scheme 2—Halogenation and Arylation

Route 1:

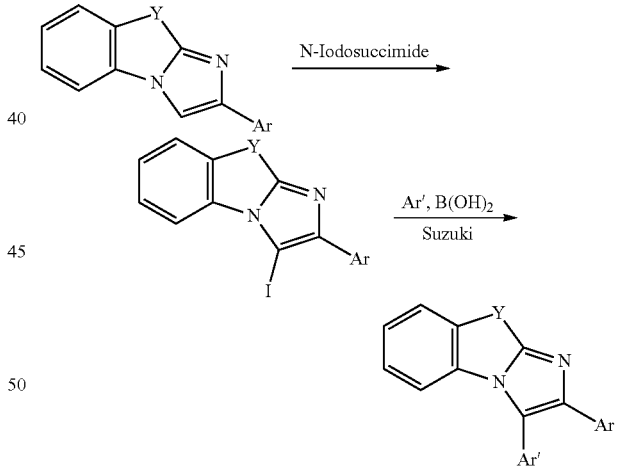

Such a halogenation reaction is known from the literature (for example in Angewandte Chemie, Int. Ed., 50(8), 1896-1900, S1896/1-S1896/10, 2011).

Route 2:

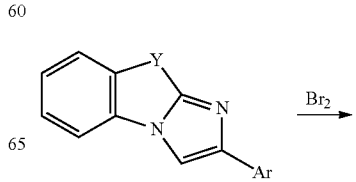

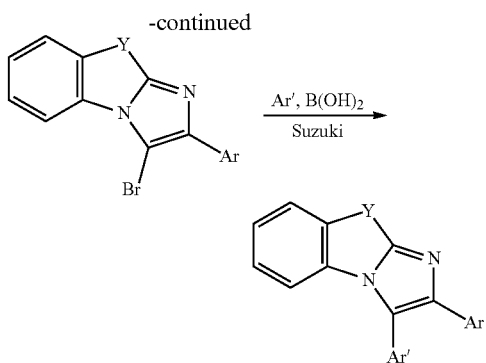

Such a halogenation reaction is known from the literature (for example in Khimiya Geterotsiklicheskikh Soedinenii, (1), 136-34, 1976)

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol-monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be at least one further organic or inorganic compound which is likewise employed in the electronic device, for example an emitting compound, in particular a phosphorescent dopant, and/or a further matrix material. Suitable emitting compounds and further matrix materials are indicated below in connection with the organic electroluminescent device. This further compound may also be polymeric.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound of the formula (1) or in accordance with the preferred embodiments as matrix material for fluorescent emitters, phosphorescent emitters or emitters showing TADF (Thermally Activated Delayed Fluorescence), in particular for phosphorescent emitters, and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1) or in accordance with the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or in accordance with the preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having spin multiplicity>1, in particular from an excited triplet state. For the purposes of this application, all luminescent transition-metal complexes and luminescent lanthanide complexes, in particular all iridium, platinum and copper complexes, are to be regarded as phosphorescent compounds.

Preferably, when the compounds of the formula (1) or in accordance with the preferred embodiments are employed as matrix materials for an emitting compound in an emitting layer, they are preferably employed in combination with one or more phosphorescent material (triplet emitters).

The mixture comprising the compound of the formula (1) or in accordance with the preferred embodiments and the emitting compound comprises between 99 and 1% by vol., preferably between 98 and 10% by vol., particularly preferably between 97 and 60% by vol., in particular between 95 and 80% by vol., of the compound of the formula (1) or in accordance with the preferred embodiments, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1) or in accordance with the preferred embodiments as matrix material for a phosphorescent emitter in combination with a further matrix material. Particularly suitable matrix materials which can be employed in combination with the compounds of the formula (1) or in accordance with the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or in accordance with EP 11003232.3, triphenylene derivatives, for example in accordance with WO 2012/048781, or lactams, for example in accordance with WO 2011/116865 or WO 2011/137951. A further phosphorescent emitter which emits at shorter wavelength than the actual emitter may likewise be present in the mixture as co-host.

Preferred co-host materials are triarylamine derivatives, in particular monoamines, lactams, carbazole derivatives and indenocarbazole derivatives.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094962, WO 2014/094961, WO 2014/094960, WO 2016/124304, WO 2016/125715, WO 2017/032439 as well as the not yet published applications EP16179378.1 and EP16186313.9. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

Examples of suitable phosphorescent emitters are the phosphorescent emitters listed in the table below:

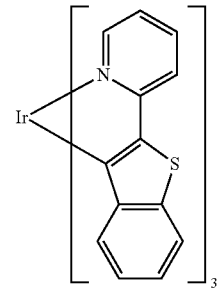

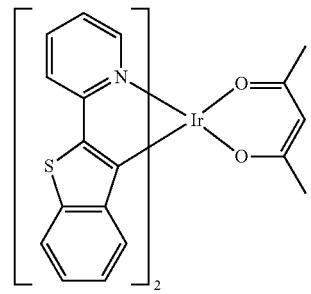

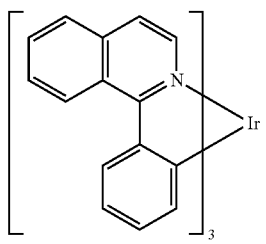
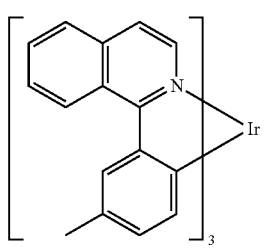
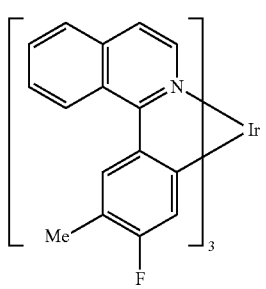
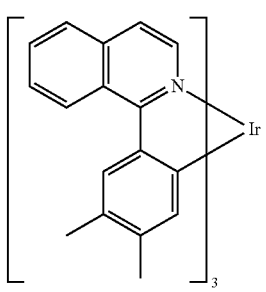
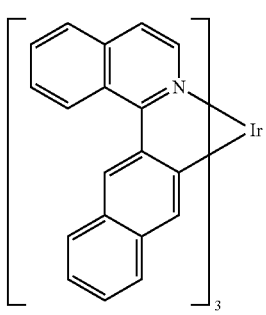
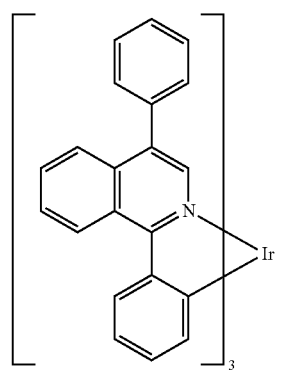
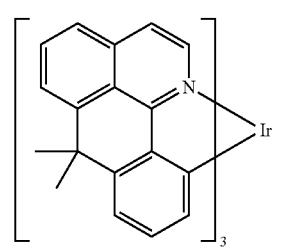
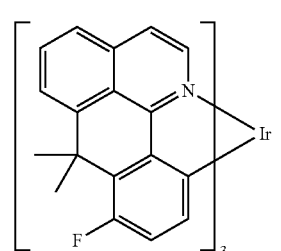
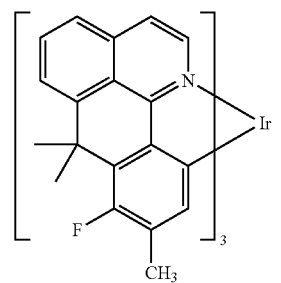
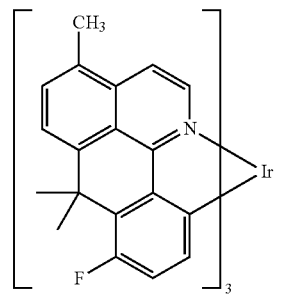

-continued
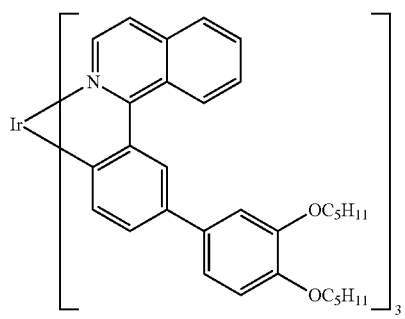
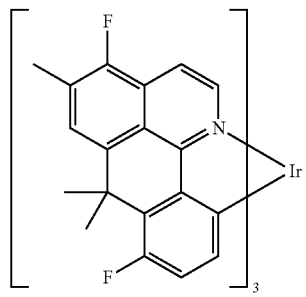
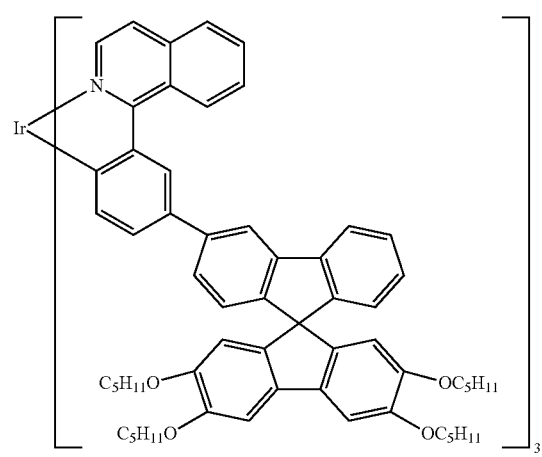
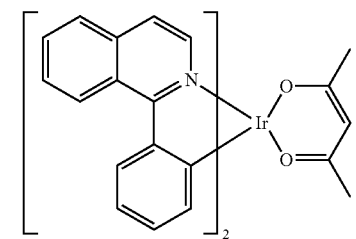
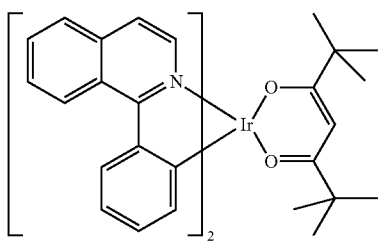
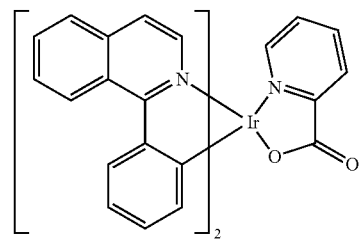
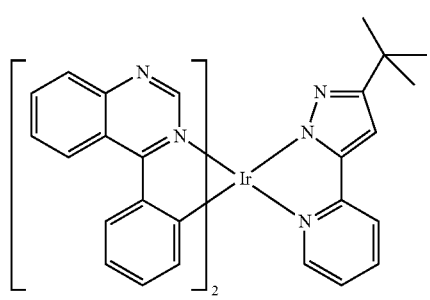
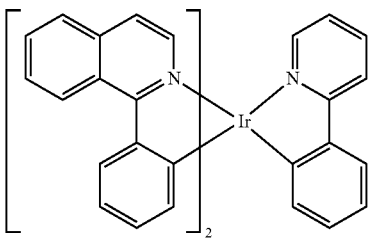
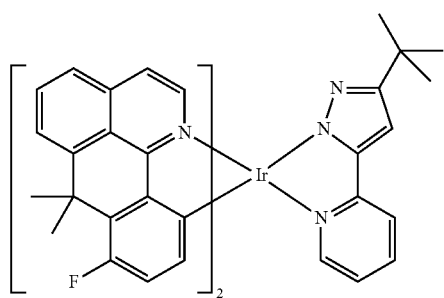

101
-continued
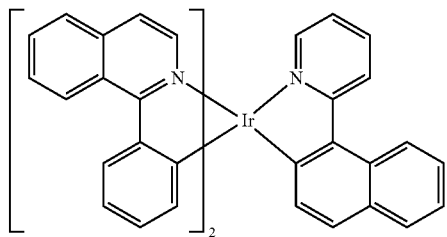
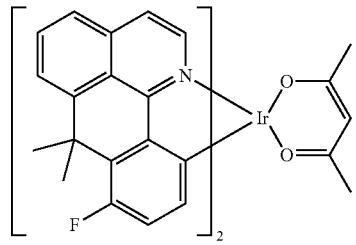
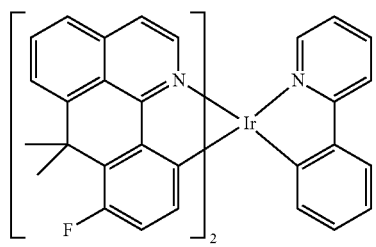
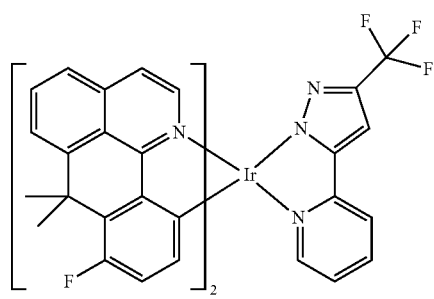
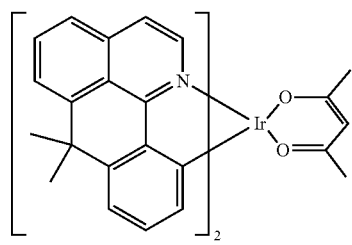
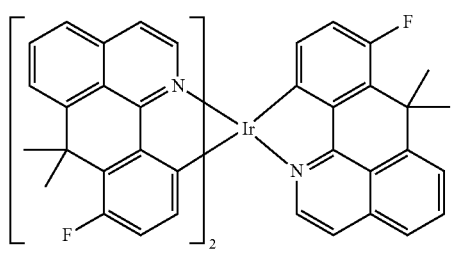
102
-continued
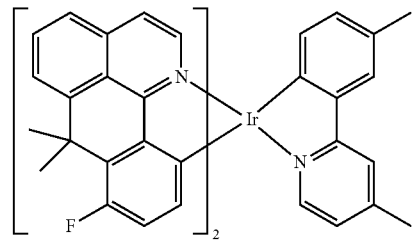
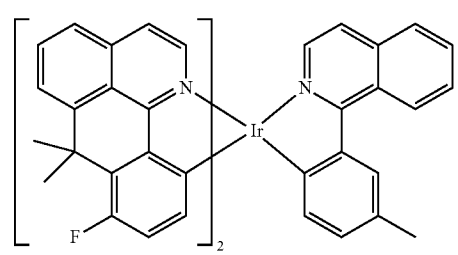
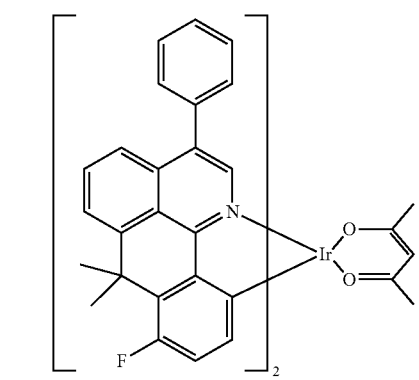
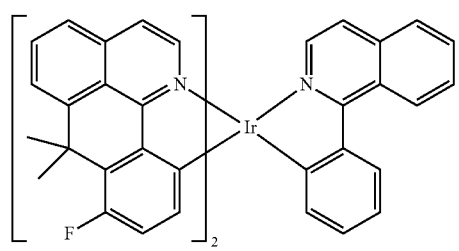
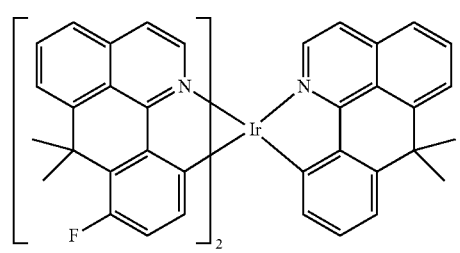

| 103 -continued | 104 -continued |
|---|---|
| 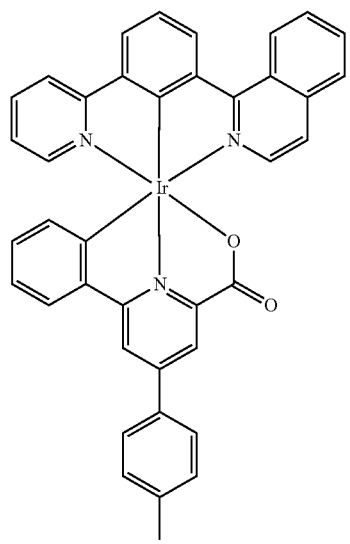 | 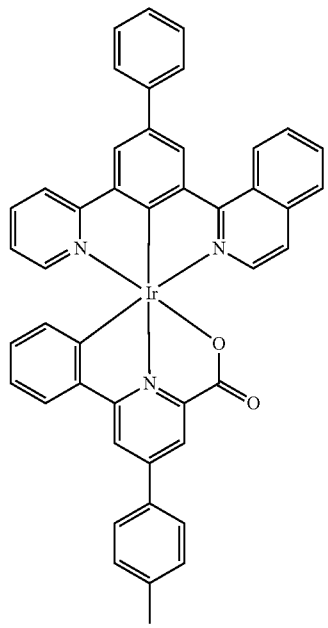 |
| 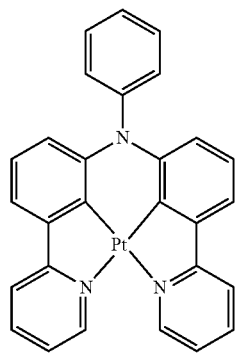 | 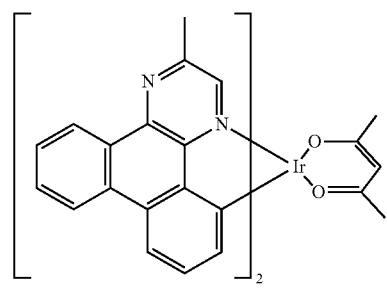 |
| 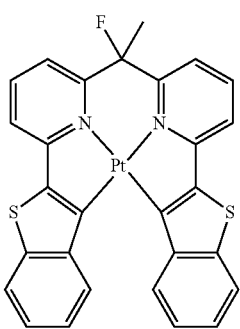 | 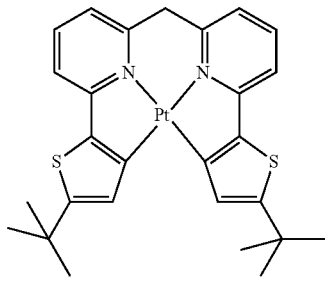 |
|  | 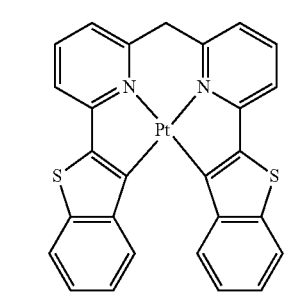 |

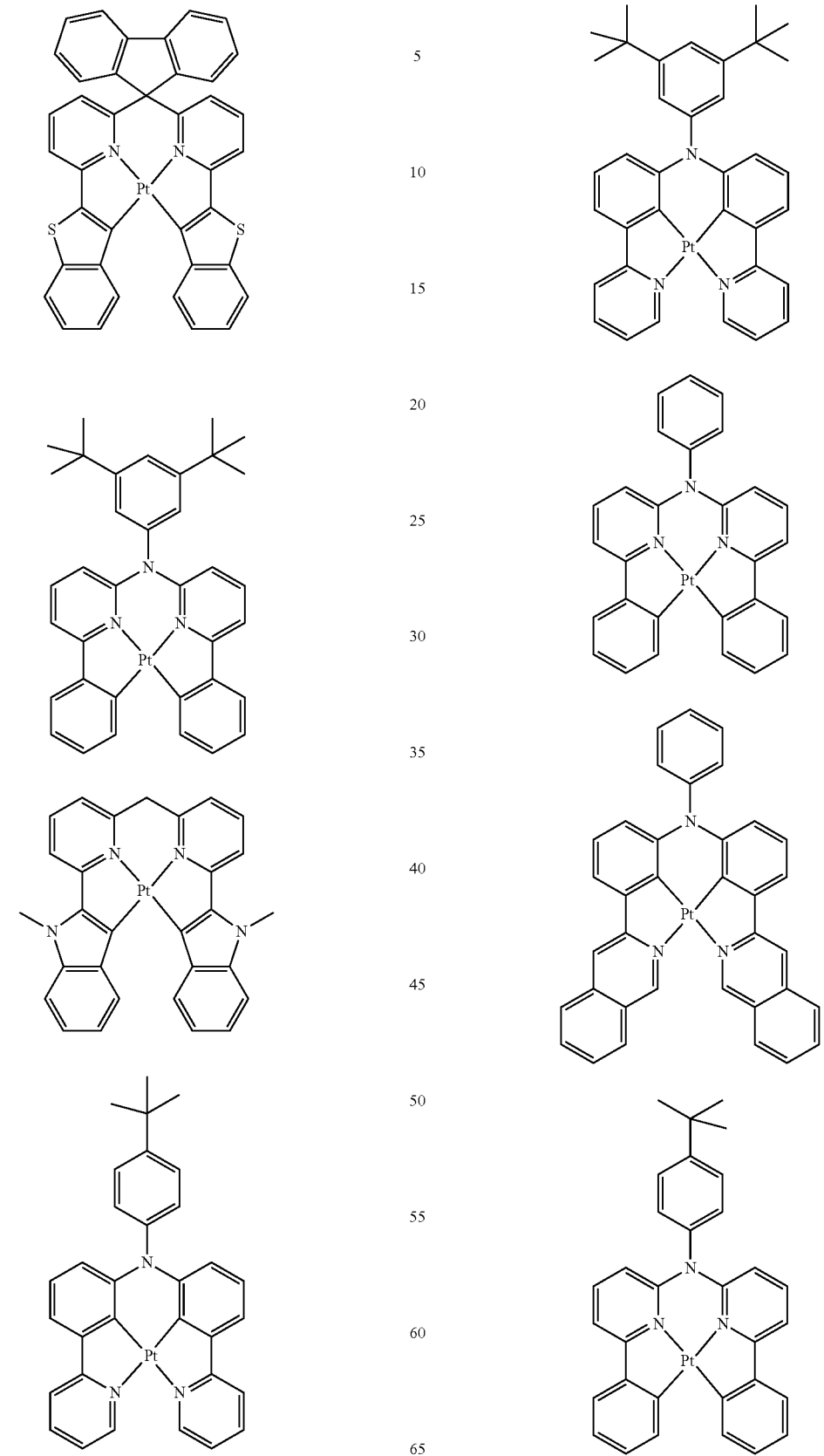

107
-continued
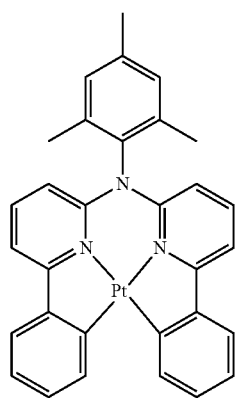
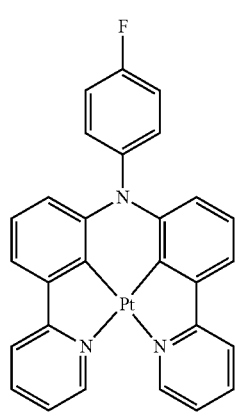
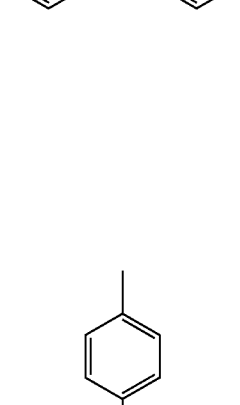
108
-continued
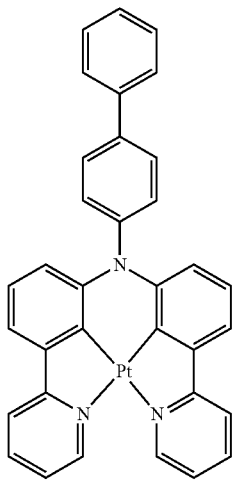
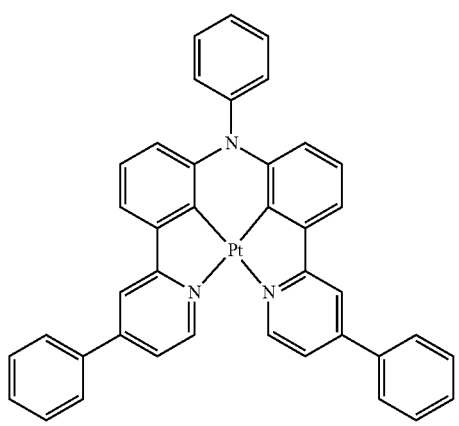
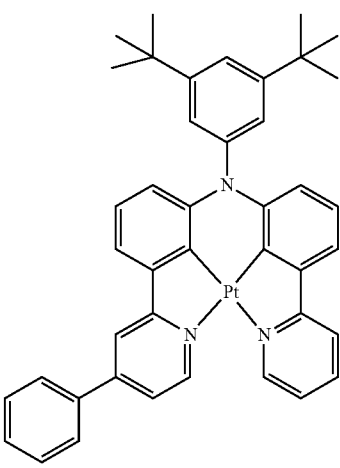

109
-continued
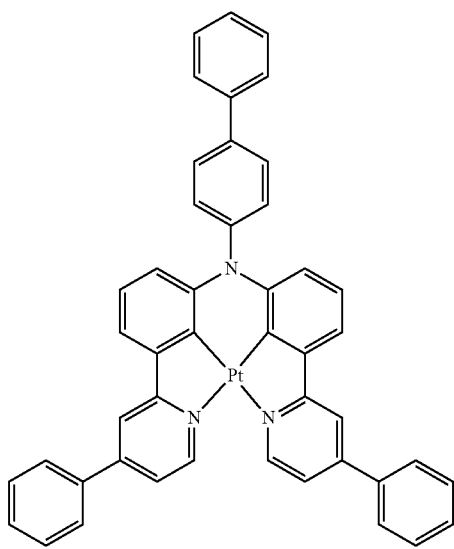
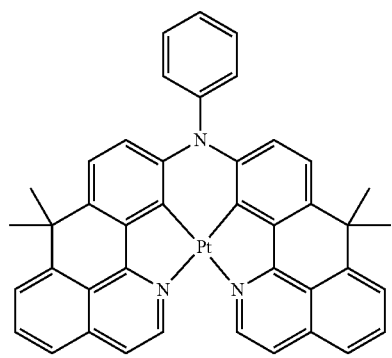
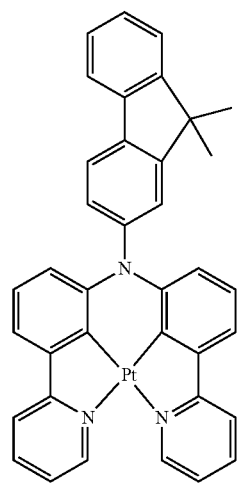
110
-continued
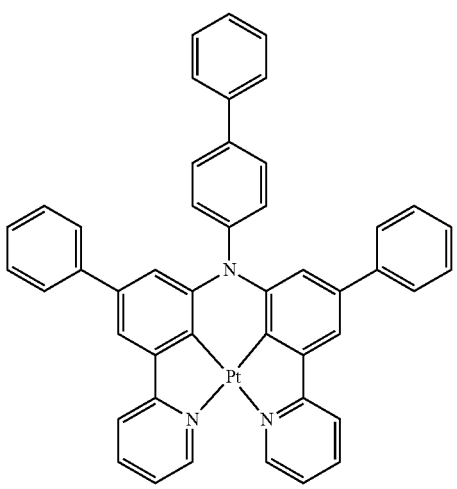
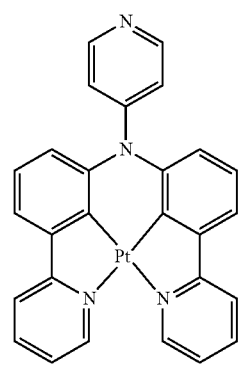
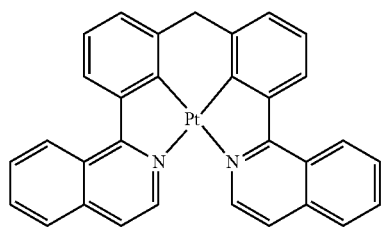
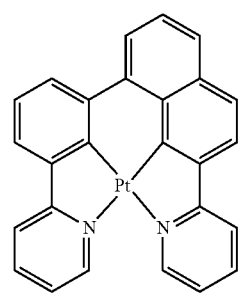

| 111 -continued | 112 -continued |
|---|---|
| 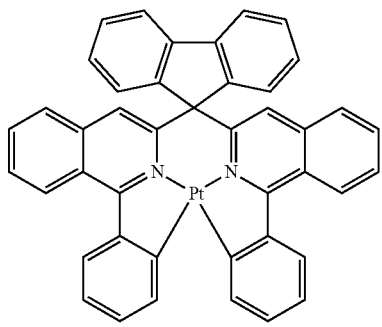 | 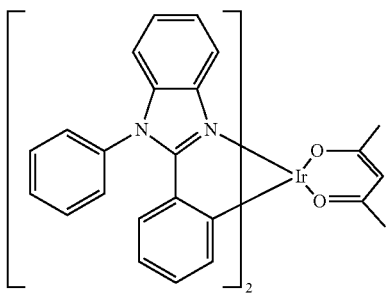 |
| 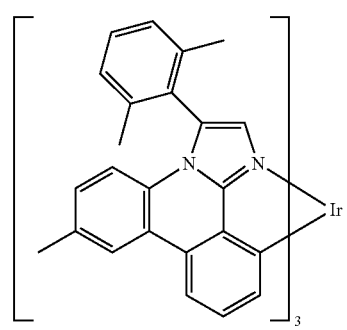 | 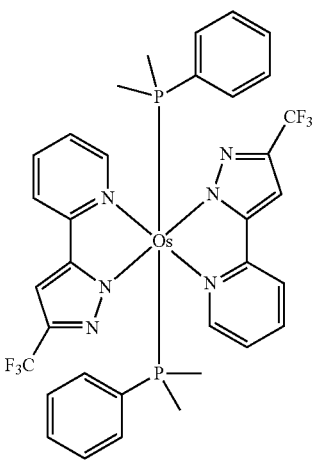 |
| 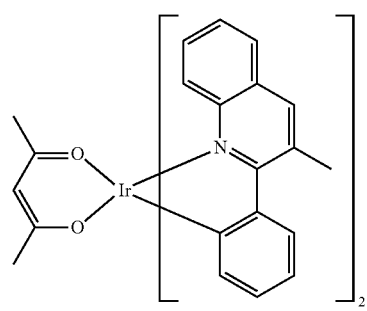 | 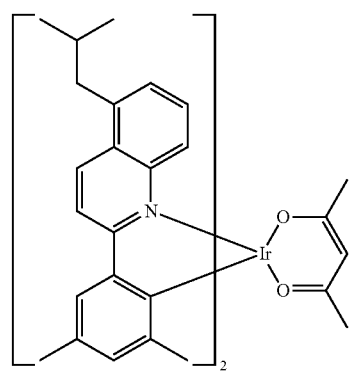 |
| 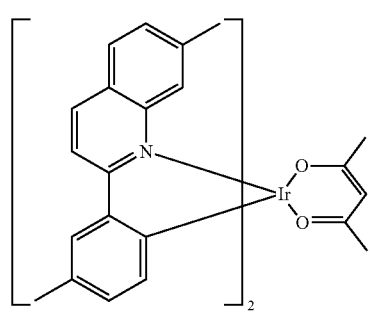 | 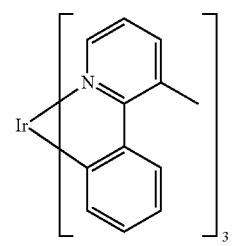 |
| 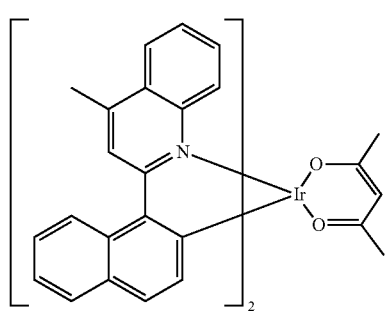 | 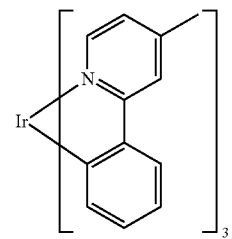 |

-continued
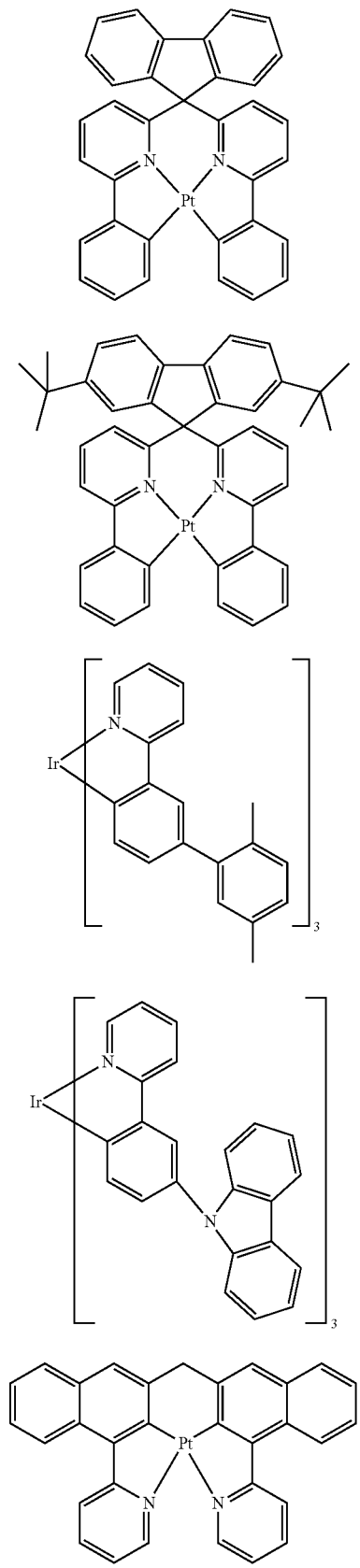
-continued
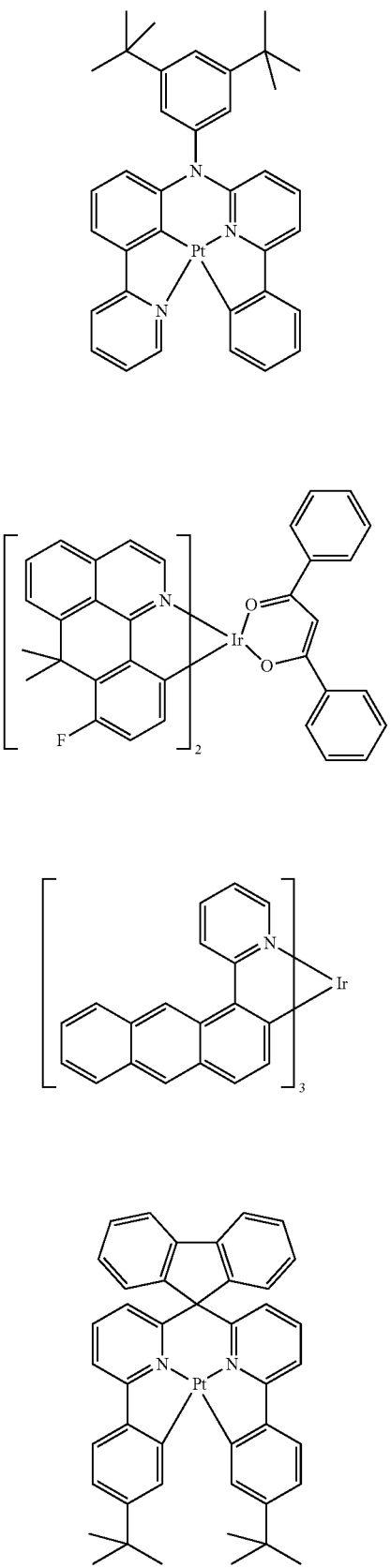

| 115 -continued | 116 -continued |
|---|---|
| 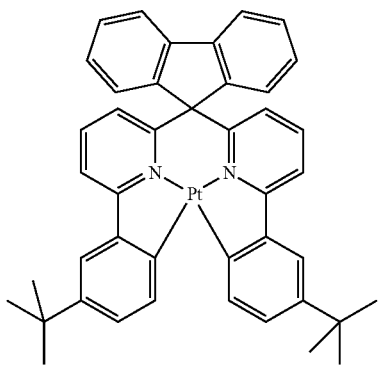 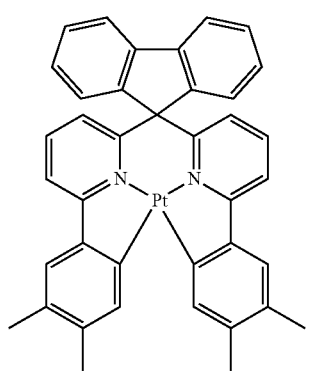 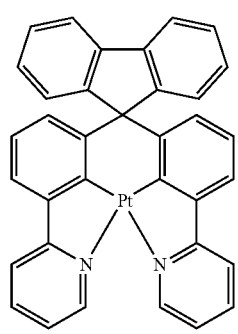 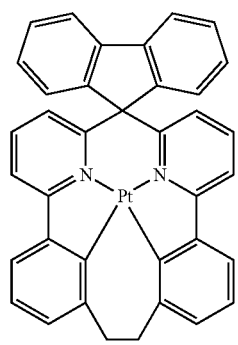 | 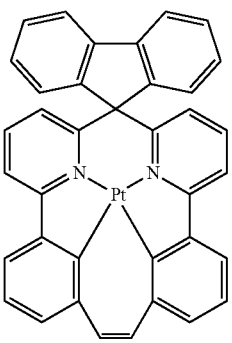 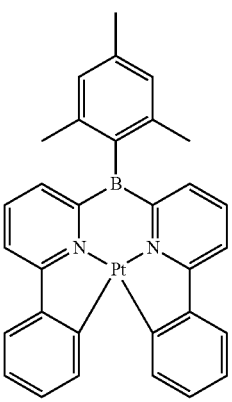 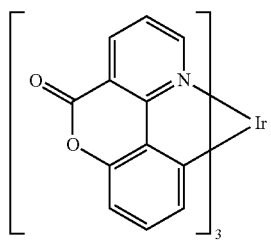 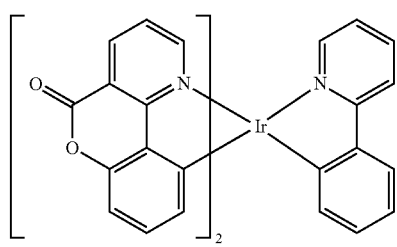 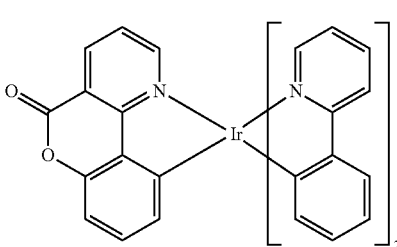 |

117
-continued
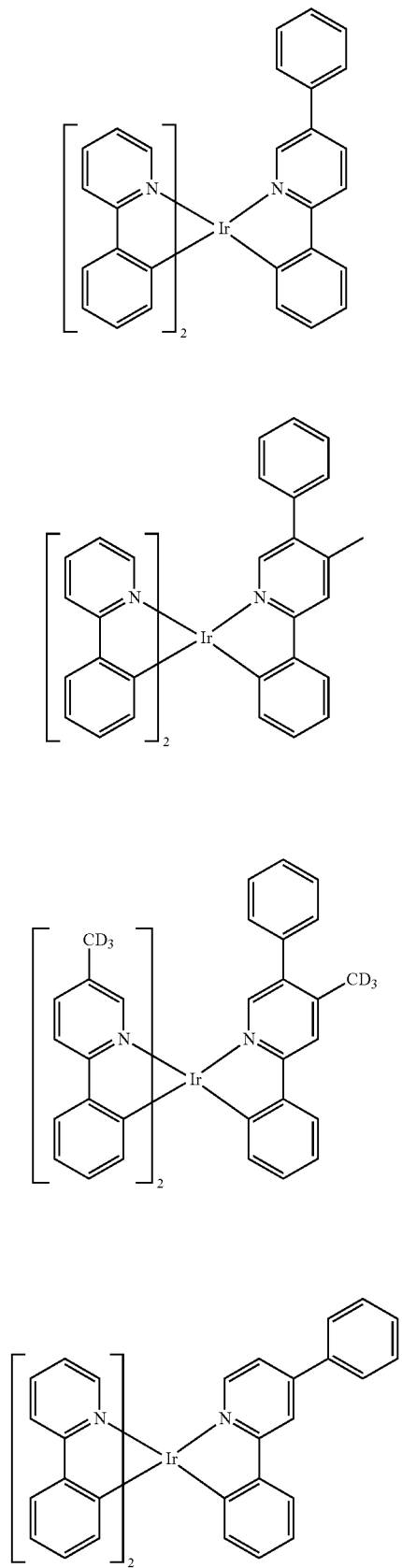
118
-continued
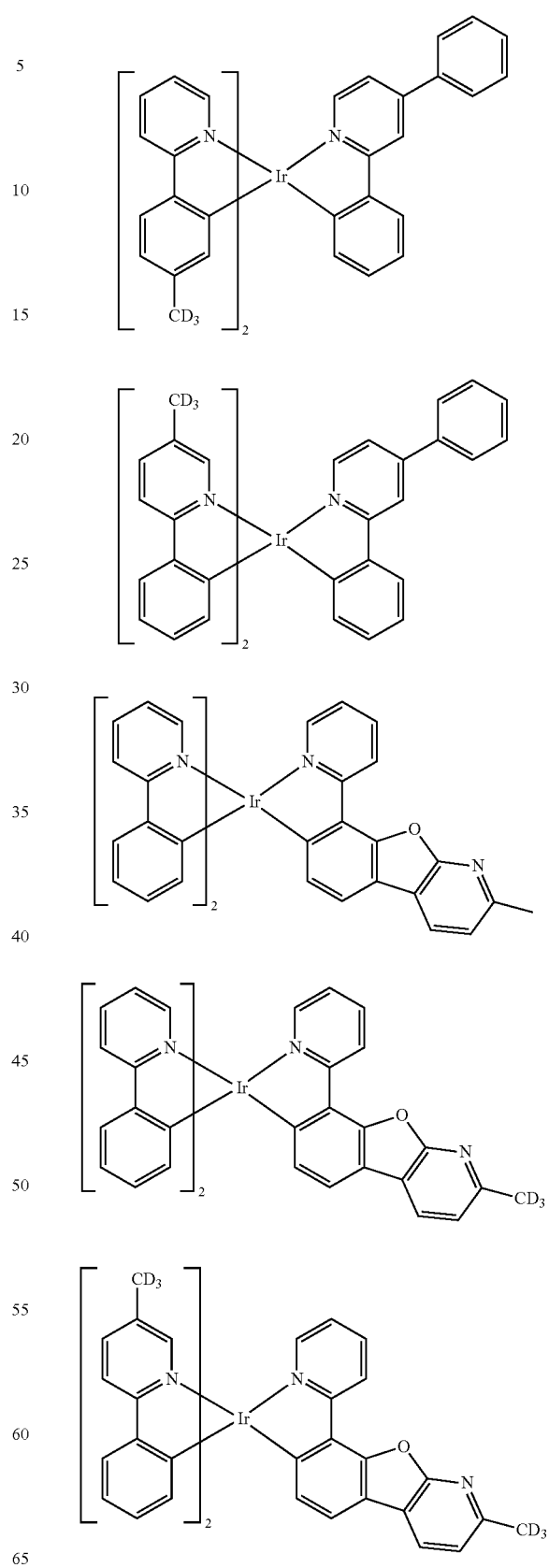

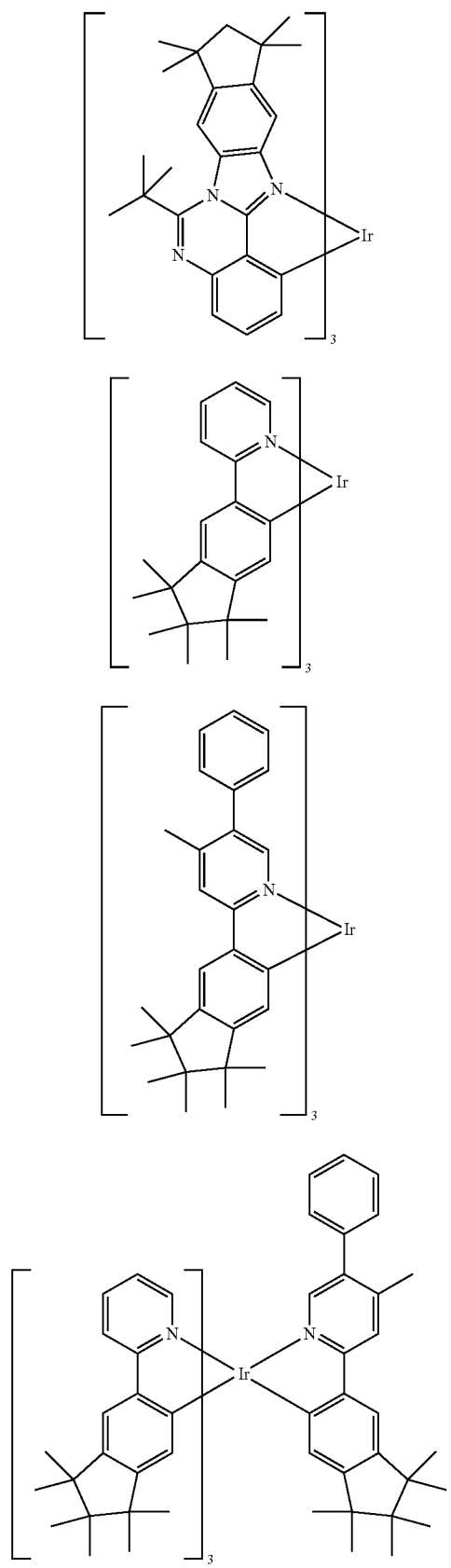
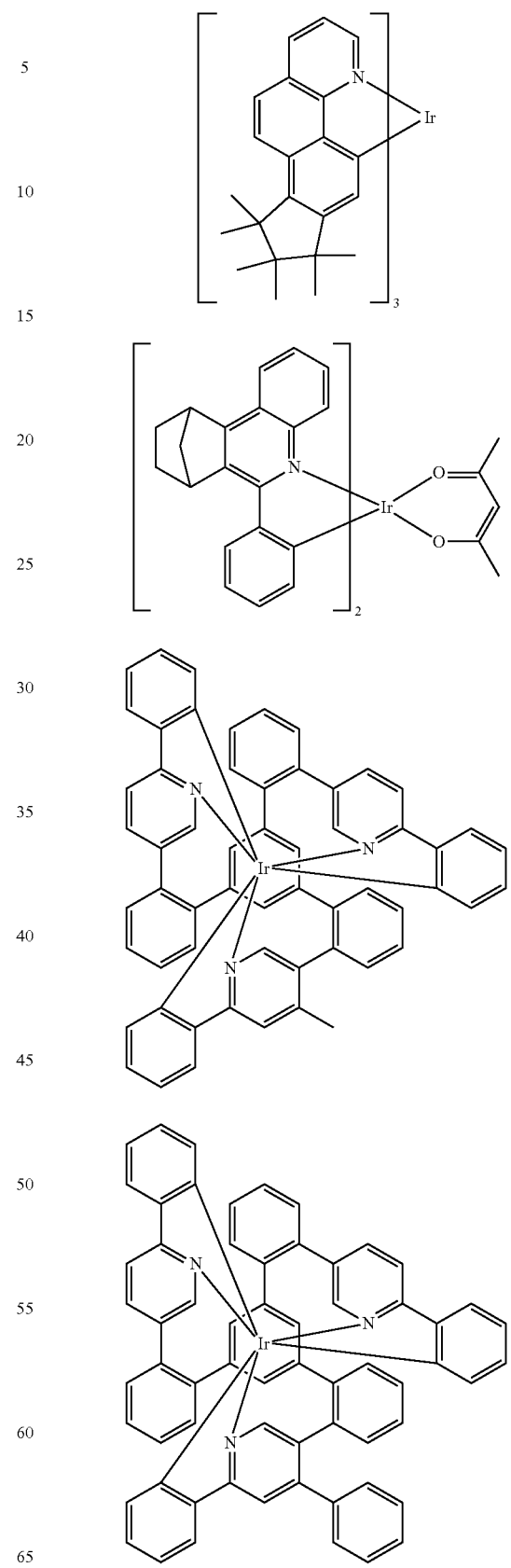

121
-continued

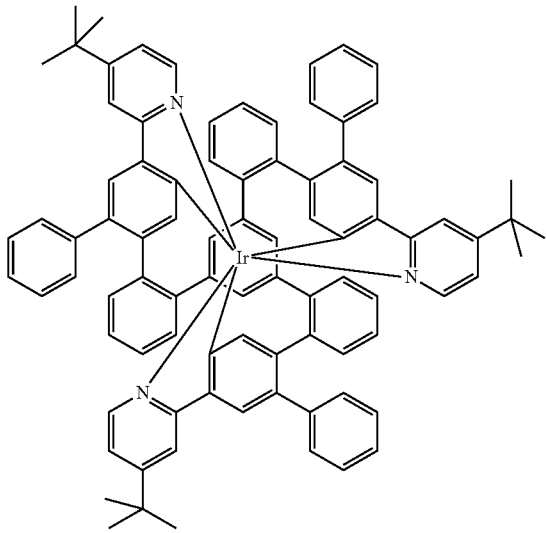

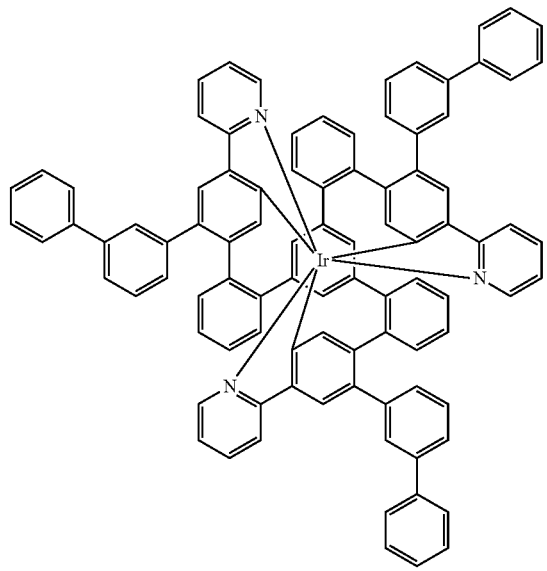

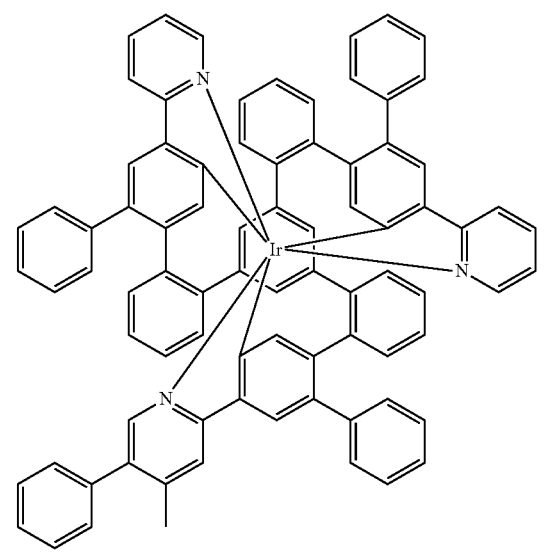

122
-continued

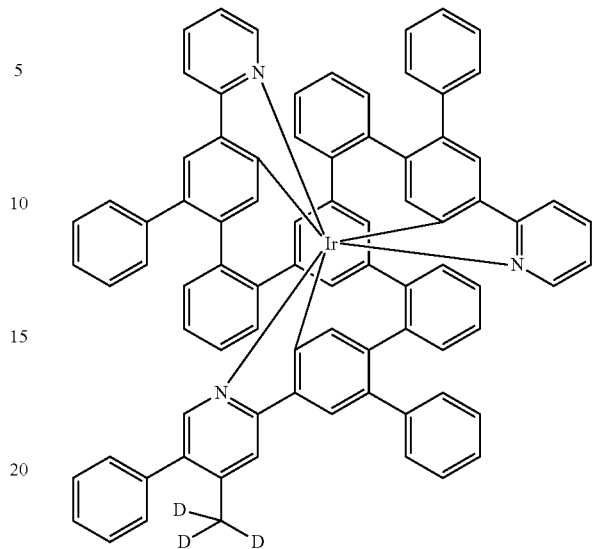

Suitable phosphorescent materials (=triplet emitters) that can be advantageously combined with the compounds of formula (1) are, as mentioned above, compounds which emit a red light on suitable excitation, which means phosphorescent materials having an excited triplet state level (T1) comprised between 550 and 680 nm.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to employ the compounds according to the invention in a hole-blocking or electron-transport layer. This applies, in particular, to compounds according to the invention which do not have a carbazole structure. These may preferably also be substituted by one or more further electron-transporting groups, for example benzimidazole groups.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) or in accordance with the preferred embodiments.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

The compounds according to the invention generally have very good properties on use in organic electroluminescent devices. In particular, the lifetime on use of the compounds according to the invention in organic electroluminescent devices is significantly better compared with similar compounds in accordance with the prior art. The other properties of the organic electroluminescent device, in particular the efficiency and the voltage, are likewise better or at least comparable. Furthermore, the compounds have a high glass transition temperature and high thermal stability.

The invention will now be explained in greater detail by the following examples, without wishing to restrict it thereby.

A) SYNTHESES EXAMPLES

The following syntheses are carried out, unless indicated otherwise, under a protective-gas atmosphere in dried solvents. The solvents and reagents can be purchased, for example, from Sigma-ALDRICH or ABCR. The corresponding CAS numbers are also indicated in each case from the compounds known from the literature.

a) 3-Benzo[d]imidazo[2,1-b]thiazol-2-yl-9-phenyl-9H-carbazole

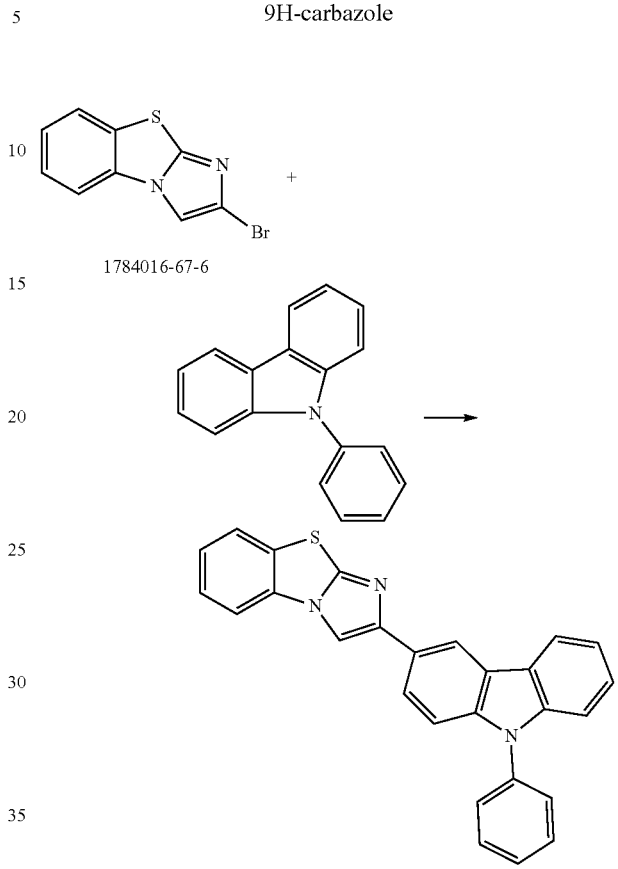

39.2 g (155 mmol) of 2-bromo-benzo[d]imidazo[2,1-b]thiazole, 59 g (169 mmol) of N-phenylcarbazole-3-boronic acid and 36 g (340 mmol) of sodium carbonate are suspended in 1000 mL of ethylene glycol dimethyl ether and 280 mL of water. Subsequently, 1.8 g (1.5 mmol) of tetrakies(triphenylphosphine)-palladium(0) are added to this suspension, and the reaction mixture is heated under reflux during 16 h. After cooling, the organic phase is separated off, filtered over silica gel, washed three times with 200 mL of water and then concentrated to dryness. The yield is 46 g (113 mmol), corresponding to 73% of the theory.

Analogously, the following compounds are prepared:

| | Educt 1 | Educt 2 | Product | Yield |
|---|---|---|---|---|
| 1a | 159063-07-7 | [1642121-58-1] | | 65% |
| 2a | 1896016-95-7 | [1361094-91-8] | | 67% |

| Educt 1 | Educt 2 | Product | Yield |
|---|---|---|---|
| 3a 1934400-76-6 | B(OH)₂ | | 76% |
| 4a 1783654-86-3 | phenylcarbazole-B(OH)₂ | | 71% |

| | Educt 1 | Educt 2 | Product | Yield |
|---|---|---|---|---|
| 5a | (structure, 368874-69-5) | (structure) | (structure) | 70% |
| 6a | (structure, 1188024-88-5) | (structure) | (structure) | 70% |

-continued

| | Educt 1 | Educt 2 | Product | Yield |
|---|---|---|---|---|
| 7a | 1188024-88-5 | [1251825-65-6] | | 63% |
| 8a | 38956-37-5 | [1416814-68-0] | | 57% |
| 9a | 159063-07-7 | | | 6% |

| Educt 1 | Educt 2 | Product | Yield |
|---|---|---|---|
| 10a 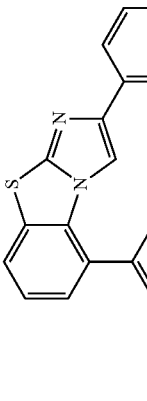<br>1188024-88-5 | 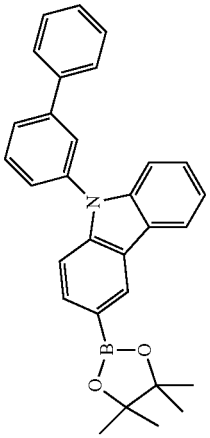<br>[1416814-68-0] | 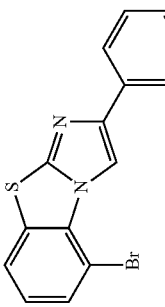 | 72% |
| 11a 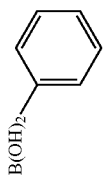<br>1783654-86-3 | B(OH)₂ | 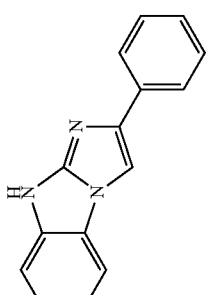 | 78% |

-continued

| | Educt 1 | Educt 2 | Product | Yield |
|---|---|---|---|---|
| 12a | [1933523-30-8] | [1572537-61-1] | | 74% |
| 13a | [1933523-31-9] | [1642121-58-1] | | 80% |

-continued

| | Educt 1 | Educt 2 | Product | Yield |
|---|---|---|---|---|
| 14a | | | | 88% |
| 15a | | | | 65% |

-continued
| | Educt 1 | Educt 2 | Product | Yield |
|---|---|---|---|---|
| 16a | 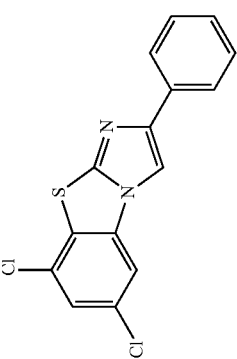 [1118217-24-4] | 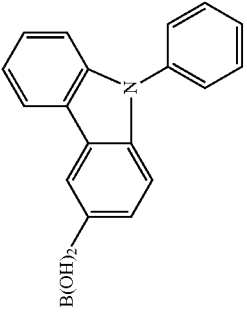 | 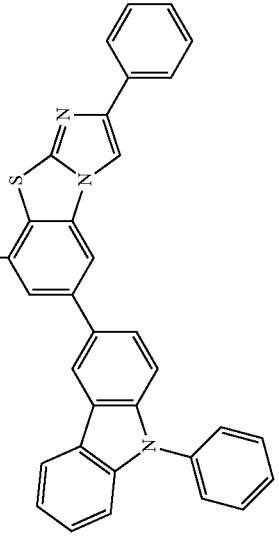 | 61% |
| 17a | 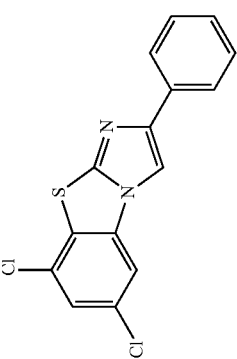 [67088-54-4] | 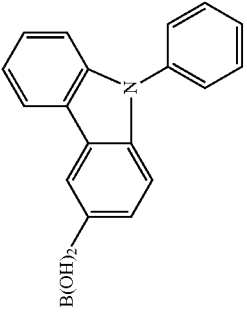 | 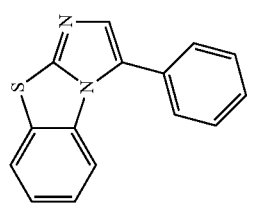 | 76% |

-continued

| | Educt 1 | Educt 2 | Product | Yield |
|---|---|---|---|---|
| 18a | [37654-58-3] | [1642121-58-1] | | 70% |
| 19a | [29200-18-8] | | | 75% |

| | Educt 1 | Educt 2 | Product | Yield |
|---|---|---|---|---|
| 20a | [159063-07-7] | carbazole-phenyl boronic acid | | 72% |
| 21a | 1934400-76-6 | carbazole-phenyl boronic acid | | 68% |
| 22a | 1783654-86-3 | B(OH)$_2$-phenyl | | 65% |

| | Educt 1 | Educt 2 | Product | Yield |
|---|---|---|---|---|
| 23a | 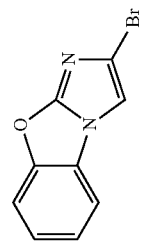 | 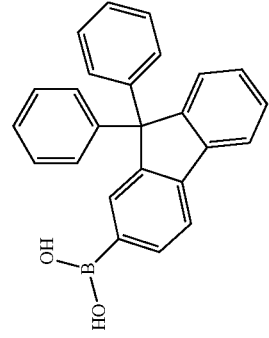[400607-31-0] | 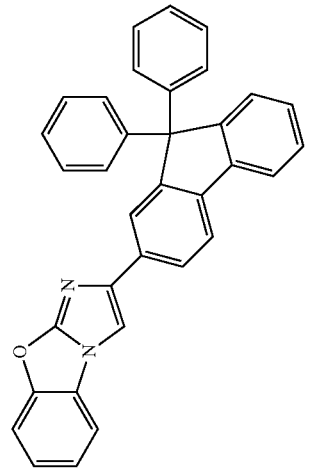 | 78% | b) 2-Bromo-3-phenyl-benzo[d]imidazo[2,1-b]thiazole

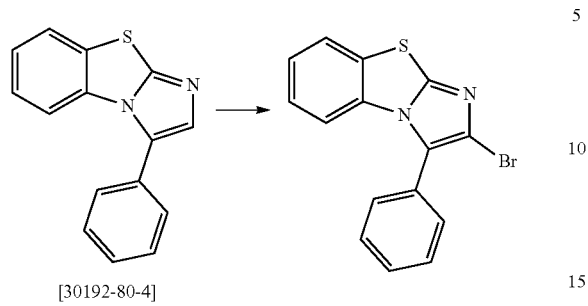

[30192-80-4]

35 g (100 mmol) of 3-phenyl-benzo[d]imidazo[2,1-b]thiazole are suspended in 400 ml of DMF and then little by little mixed with, in total, 18.8 g (100 mmol) of N-bromosuccinimide at −150° C. The mixture is then mixed for 18 hours. After cooling, the reaction mixture is concentrated using a rotavapor, dissolved with dichloromethane and washed with water. It is then dried, concentrated, and then recrystallized from toluene to arrive at a purity of 97%. The yield is 30 g (93 mmol), corresponding to 67% of the theory.

Analogously, the following compounds are prepared:

| | Educt 1 | Product | Yield |
|---|---|---|---|
| 1b | | | 48% |
| 2b | | | 73% |
| 3a | | | 70% |

-continued

| Educt 1 | Product | Yield |
|---|---|---|
| 4b | | 63% |
| 5b | | 69% |
| 6b | | 66% |
| 7b | | 71% |
| 8b 30452-31-4 | | 81% |
| 9b 1692899-56-1 | | 84% |

-continued
| Educt 1 | Product | Yield |
|---|---|---|
| 10b 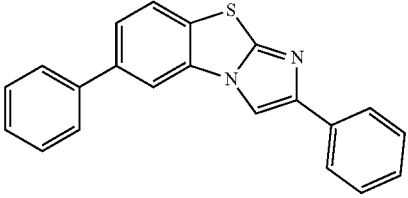 1692899-49-2 | 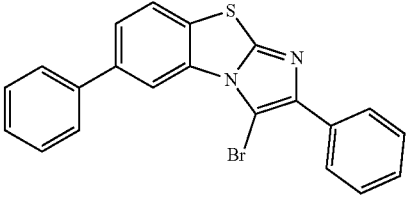 [SMILES: Brc1c(-c2ccccc2)nc2sc3ccc(-c4ccccc4)cc3n12] | 83% |
| 11b 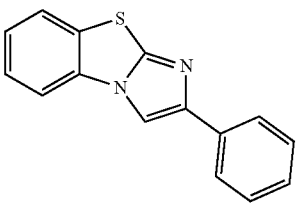 17833-07-7 | 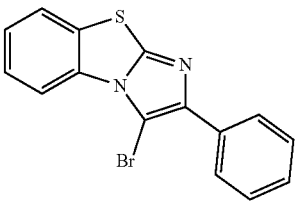 [SMILES: Brc1c(-c2ccccc2)nc2sc3ccccc3n12] | 80% |
| 12b 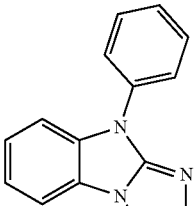 1352820-73-5 | 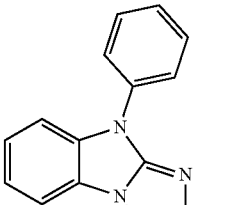 | 54% |
| 13b 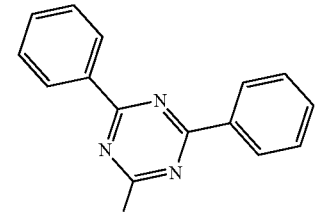 1434438-07-9 | 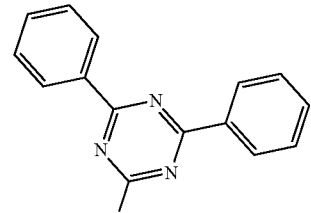 | 50% |
| 14b 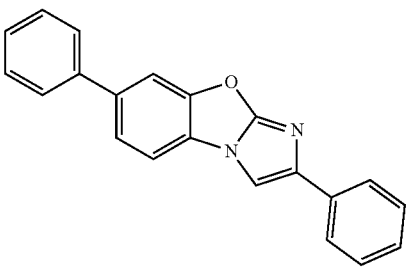 [SMILES: Brc1c(-c2ccccc2)nc2oc3cc(-c4ccccc4)ccc3n12] 1692899-55-0 | 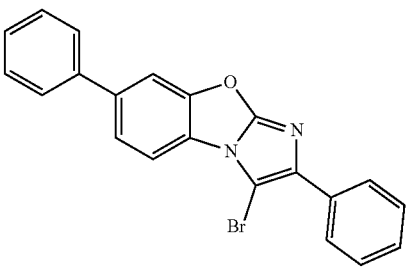 [SMILES: Brc1c(-c2ccccc2)nc2oc3cc(-c4ccccc4)ccc3n12] | 71% |

-continued
| Educt 1 | Product | Yield |
|---|---|---|
| 15b 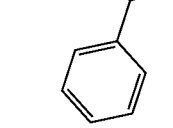 [345219-12-7] | 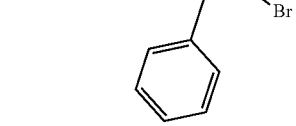 | 87% |
| 16b 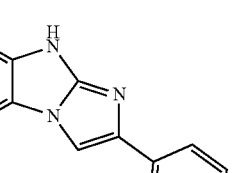 | 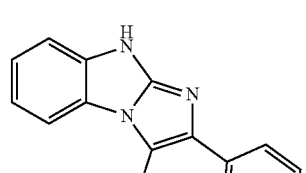 | 77% |
| 17b 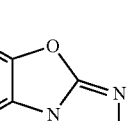 [28648-04-6] | 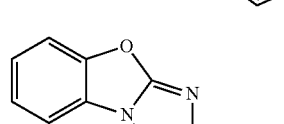 | 78% |
| 18b 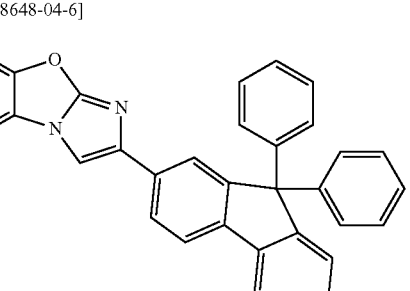 | 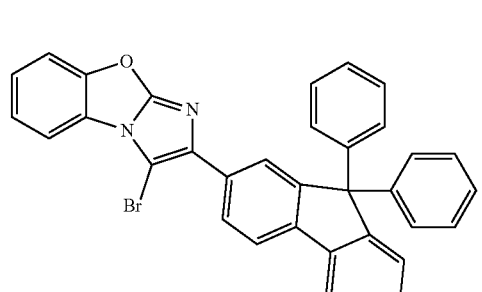 | 79% |
| 19b 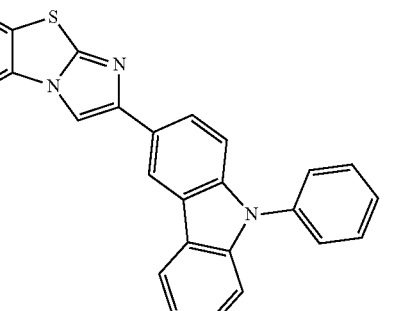 | 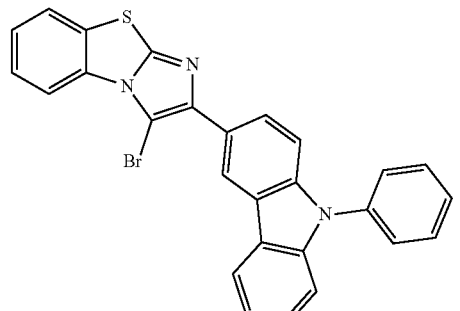 | 65% |
| 20b 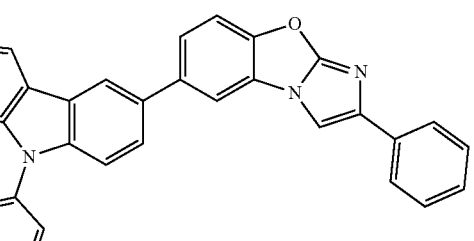 | 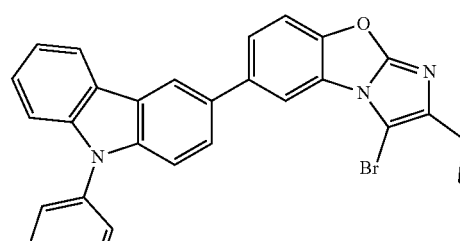 | 60% |

-continued

| Educt 1 | Product | Yield |
|---|---|---|
| 21b | | 61% |
| 22b | | 80% |

Analogously, the following compounds are prepared:

| Educt 1 | Educt 2 | Product | Yield |
|---|---|---|---|
| 24a | [1642121-58-1] | | 65% |
| 25a | | | 67% |

-continued

| | Educt 1 | Educt 2 | Product | Yield |
|---|---|---|---|---|
| 26a | | | | 76% |
| 27a | | | | 71% |
| 28a | | | | 70% |
| 29a | | | | 70% |

-continued

| | Educt 1 | Educt 2 | Product | Yield |
|---|---|---|---|---|
| 30a | | [1361094-91-8] | | 63% |
| 31a | | [1416814-68-0] | | 57% |
| 32a | | | | 6% |
| 33a | | [1361094-91-8] | | 72% |

| Educt 1 | Educt 2 | Product | Yield |
|---|---|---|---|
| 34a | [1416814-68-0] | | 78% |
| 35a | [1572537-61-1] | | 74% |
| 36a | | | 80% |
| 37a | | | 88% |

-continued

| Educt 1 | Educt 2 | Product | Yield |
|---|---|---|---|
| 38a | | | 65% |
| 39a | 854952-60-6 | | 61% |
| 40a [1933523-30-8] | 1001911-63-2 | | 76% |
| 41a [1933523-30-8] | [1391729-63-7] | | 70% |
| 42a [1933523-30-8] | [1379585-25-7] | | 75% |

-continued

| | Educt 1 | Educt 2 | Product | Yield |
|---|---|---|---|---|
| 43a | [1933523-30-8] | [1373359-67-1] | | 72% |
| 45a | [1933523-30-8] | [1314019-74-3] | | 68% |
| 46a | | [1642121-58-1] | | 60% |
| 47a | [1933523-31-9] | | | 61% |
| 48a | | | | 63% |

-continued

| Educt 1 | Educt 2 | Product | Yield |
|---|---|---|---|
| 49a | | | 71% |
| 50a | [1642121-58-1] | | 68% |
| 51a | [1572537-61-1] | | 66% |
| 52a | | | 77% |

-continued

| Educt 1 | Educt 2 | Product | Yield |
|---|---|---|---|
| 53a | [1572537-61-1] | | 69% |
| 54a | B(OH)₂–Ph | | 90% |
| 55a [1933523-31-9] | | | 56% |
| 56a | | | 75% |
| 57a 1783654-86-3 | | | 65% |

-continued
| Educt 1 | Educt 2 | Product | Yield |
|---|---|---|---|
| 58a 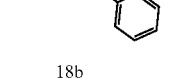 18b | 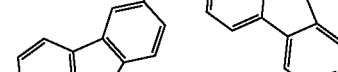 |  | 67% |
| 59a  | 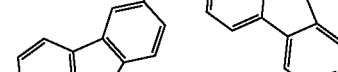 | 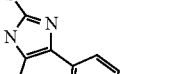 | 66% |
| 60a 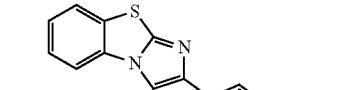 | 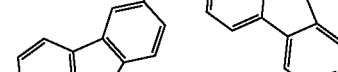 |  | 71% |
| 61a 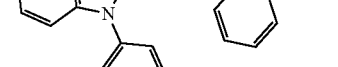 | 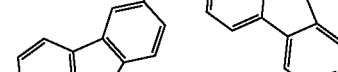 | | 74% |

| Educt 1 | Educt 2 | Product | Yield |
|---|---|---|---|
| 62a 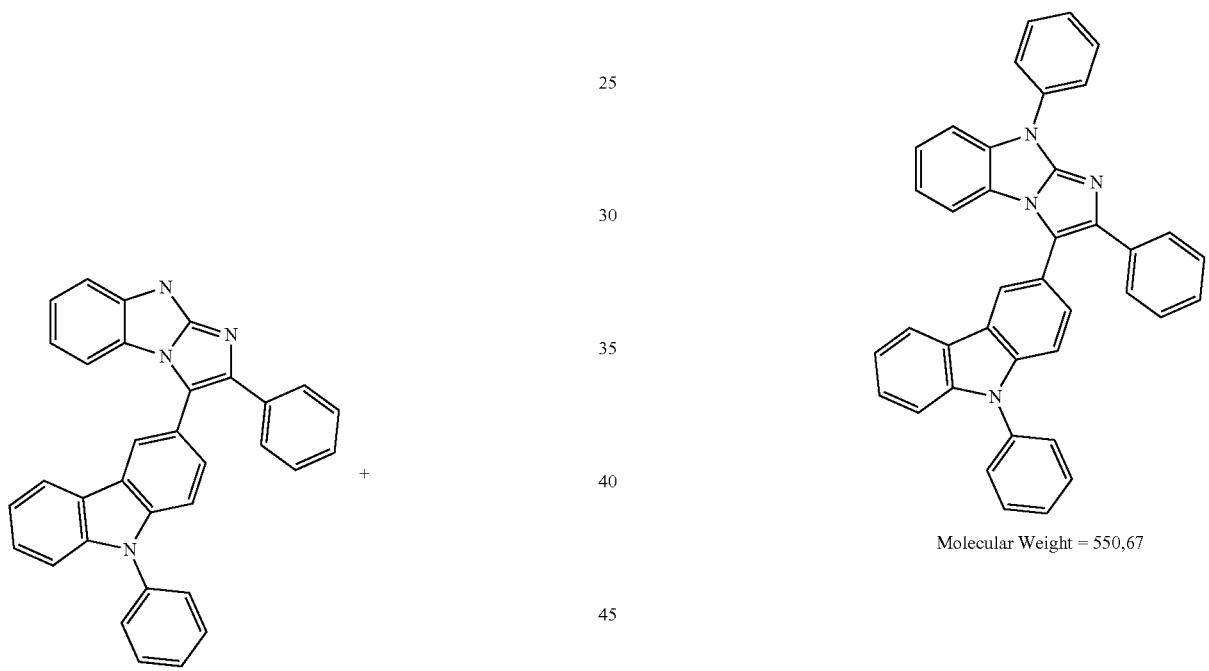 | | | 65% | c) 3-(2,9-diphenyl-9H-benzo[d]imidazo[1,2-a]imidazol-3-yl)-9-phenyl-9H-carbazole

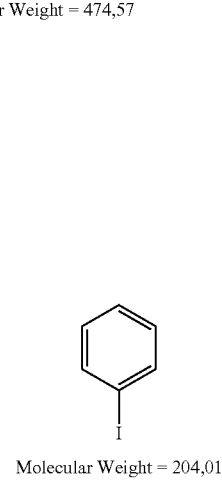

A degassed solution of 29 g (146 mmol) of iodobenzene and 69 g (146 mmol) of 9-phenyl-3-(2-phenyl-9H-benzo[d]imidazo[1,2-a]imidazol-3-yl)9H-carbazole, in 700 mL of toluene, is saturated with N2 during 1 h.

Subsequently, 2.09 ml (8.5 mmol) of P(tBu)$_3$ are mixed with the mixture followed by 1.38 g (6.1 mmol) of palladium (II)acetate and by the addition of 17.5 g (184 mmol) of NaOtBu in the solid state. The reaction mixture is then heated under reflux during 1 h. After cooling to room temperature, 500 mL of water are carefully added. The aqueous phase is washed with 3×50 ml of toluene, dried over MgSO$_4$ and the solvent is removed in vacuo. The crude product is then purified by chromatography on silica gel using heptane/acetic acid ester (20:2). The residue is recrystallized from toluene and finally sublimated in high vacuum (p=5×10$^{-6}$ mbar).

The yield is 64 g (116 mmol), corresponding to 80% of the theory.

Analogously, the following compounds are prepared:
| Educt 1 | Educt 2 | Product | Yield |
|---|---|---|---|
| 1c 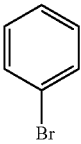 | 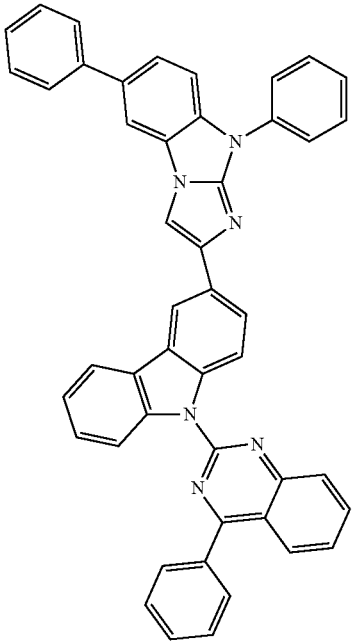 [SMILES: c1ccc(-c2ccc3c(c2)n2cc(-c4ccc5c(c4)c4ccccc4n5-c4nc(-c5ccccc5)c5ccccc5n4)nc2n3-c2ccccc2)cc1] | 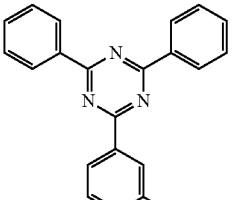 | 58% |
| 2c 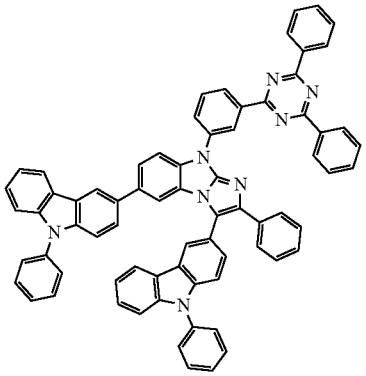 [SMILES: c1ccc(-c2nc(-c3ccccc3)nc(-c3cccc(-n4c5ccc(-c6ccc7c(c6)c6ccccc6n7-c6ccccc6)cc5n5c(-c6ccc7c(c6)c6ccccc6n7-c6ccccc6)c(-c6ccccc6)nc45)c3)n2)cc1] | 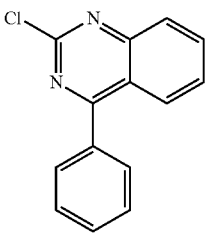 [864377-31-1] | 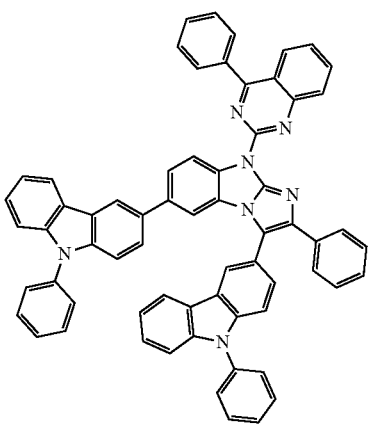 [SMILES: c1ccc(-c2nc3n(-c4nc(-c5ccccc5)c5ccccc5n4)c4ccc(-c5ccc6c(c5)c5ccccc5n6-c5ccccc5)cc4n3c2-c2ccc3c(c2)c2ccccc2n3-c2ccccc2)cc1] | 60% |
| 3c | Cl—... [29874-83-7] | | 57% |

| Educt 1 | Educt 2 | Product | Yield |
|---|---|---|---|
| 4c 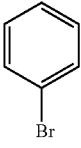 | 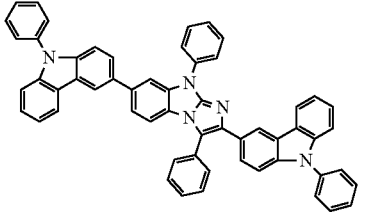 [SMILES: c1ccc(-c2c(-c3ccc4c(c3)c3ccccc3n4-c3ccccc3)nc3n(-c4ccccc4)c4cc(-c5ccc6c(c5)c5ccccc5n6-c5ccccc5)ccc4n23)cc1] | 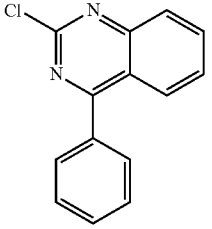 | 62% |
| 5c 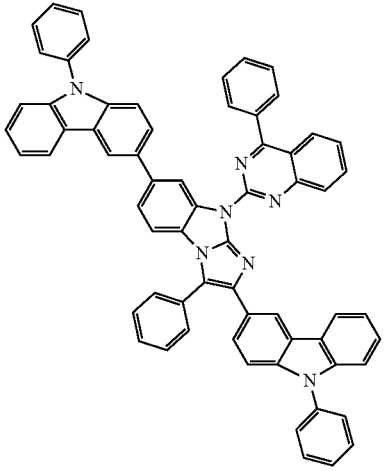 [SMILES: c1ccc(-c2nc(-n3c4cc(-c5ccc6c(c5)c5ccccc5n6-c5ccccc5)ccc4n4c(-c5ccccc5)c(-c5ccc6c(c5)c5ccccc5n6-c5ccccc5)nc34)nc3ccccc23)cc1] | [29874-83-7] | | 63% |

| Educt 1 | Educt 2 | Product | Yield |
|---|---|---|---|
| 6c 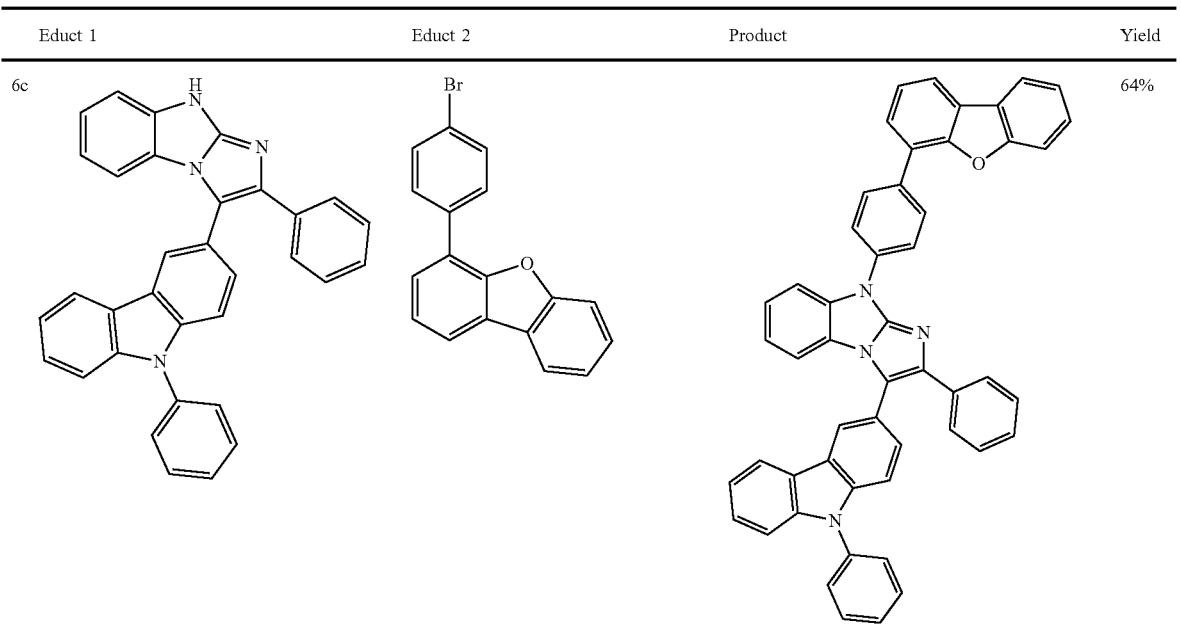 | | | 64% |
| 7c 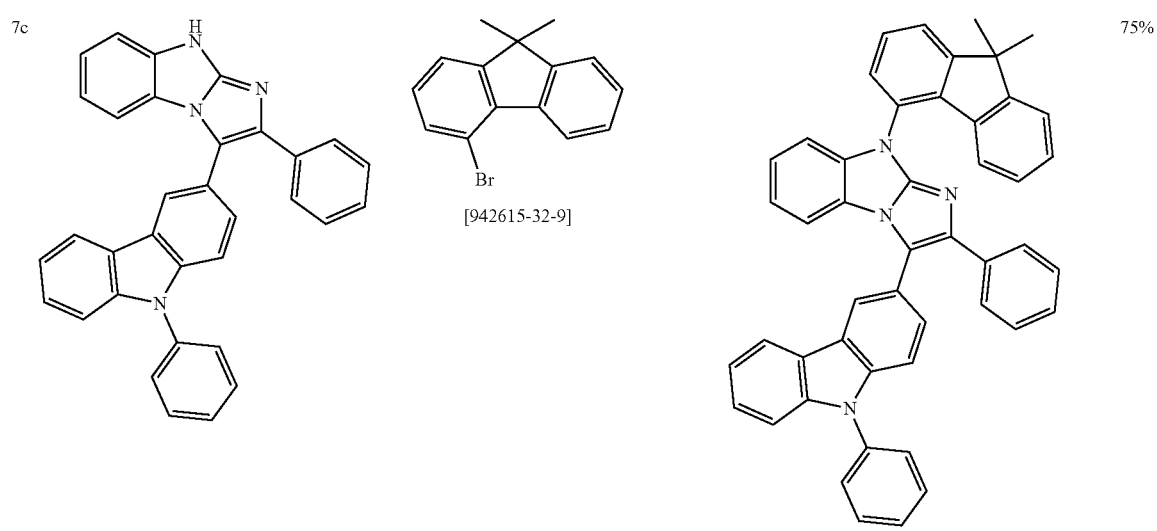 | | | 75% |

-continued
| Educt 1 | Educt 2 | Product | Yield |
|---|---|---|---|
| 8c 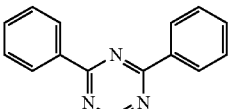 | 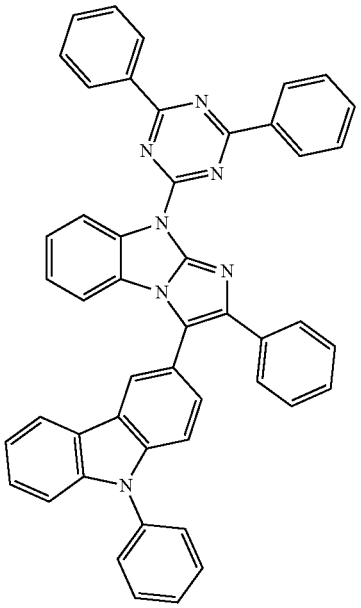 [SMILES: c1ccc(-c2nc(-c3ccccc3)nc(-n3c4ccccc4n4c(-c5ccc6c(c5)c5ccccc5n6-c5ccccc5)c(-c5ccccc5)nc34)n2)cc1] [3842-55-5] | 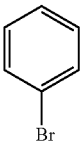 | 68% |
| 9c 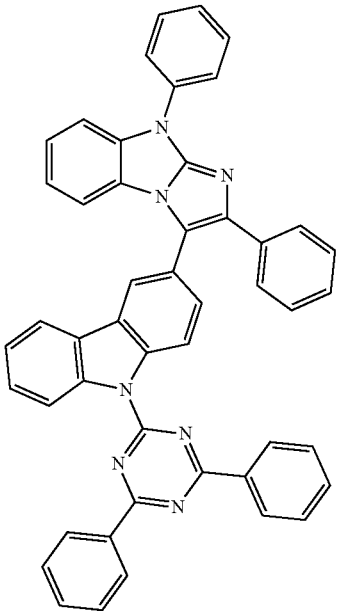 [SMILES: c1ccc(-c2nc(-c3ccccc3)nc(-n3c4ccccc4c4cc(-c5c(-c6ccccc6)nc6n(-c7ccccc7)c7ccccc7n56)ccc43)n2)cc1] | Br | | 62% |

-continued
| Educt 1 | Educt 2 | Product | Yield |
|---|---|---|---|
| 10c 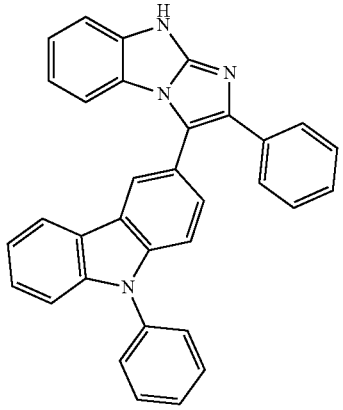 [SMILES: c1ccc(-c2nc3[nH]c4ccccc4n3c2-c2ccc3c(c2)c2ccccc2n3-c2ccccc2)cc1] | 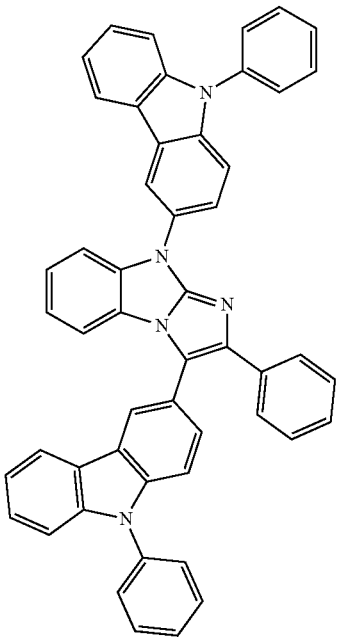 [SMILES: c1ccc(-c2nc3n(-c4ccc5c(c4)c4ccccc4n5-c4ccccc4)c4ccccc4n3c2-c2ccc3c(c2)c2ccccc2n3-c2ccccc2)cc1] | 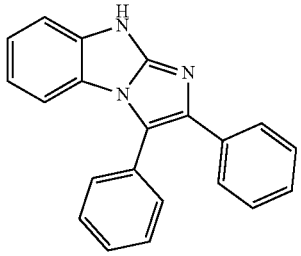 [SMILES: c1ccc(-c2nc3[nH]c4ccccc4n3c2-c2ccccc2)cc1] | 73% |
| 11c 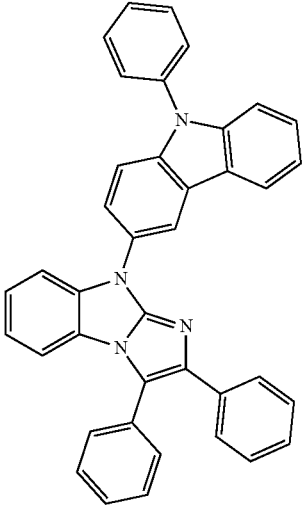 [SMILES: c1ccc(-c2nc3n(-c4ccc5c(c4)c4ccccc4n5-c4ccccc4)c4ccccc4n3c2-c2ccccc2)cc1] | 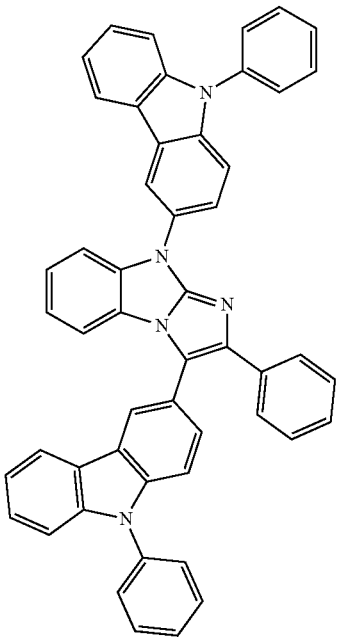 [SMILES: c1ccc(-c2nc3n(-c4ccc5c(c4)c4ccccc4n5-c4ccccc4)c4ccccc4n3c2-c2ccc3c(c2)c2ccccc2n3-c2ccccc2)cc1] | 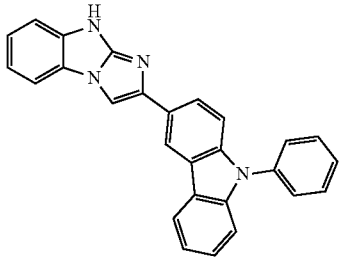 [SMILES: c1ccc(-n2c3ccccc3c3cc(-c4cn5c(n4)[nH]c4ccccc45)ccc32)cc1] | 76% |
| 12c 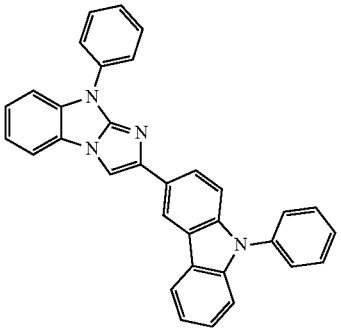 [SMILES: c1ccc(-n2c3ccccc3c3cc(-c4cn5c6ccccc6n(-c6ccccc6)c5n4)ccc32)cc1] | Br-Ph | (product) | 70% |

B) FABRICATION OF OLEDS

The following examples V1 to E8 (see Table 1 and 2) show data of various OLEDs.

Substrate Pre-Treatment of Examples V1-E8:

Glass plates with structured ITO (50 nm, indium tin oxide) form the substrates on which the OLEDs are processed. Before evaporation of the OLED materials, the substrates are cleaned in a wet process (using filtered deionized water and the detergent "Extran" of Merck KGaA). Subsequently the clean and dry substrates are exposed to a UV-Ozone plasma and then coated with a layer of 20 nm PEDOT:PSS (Poly(3,4-ethylendioxythiophen) poly(styrolsulfonate), by using an aqueous solution of CLEVIOS™ P VP AI 4083 purchased from Heraeus Precious Metals GmbH, Germany, for better processing. Before evaporating OLED materials onto the glass substrates, these are dried for 15 minutes at 170° C.

The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The exact layer structure is denoted in Table 1 (ITO, PEDOT:PSS and Aluminium layers are omitted for clarity). The materials used for the OLED fabrication are presented in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as IC1:M1:TEG1 (55%:35%:10%) here means that material IC1 is present in the layer in a proportion by volume of 55%, M1 is present in the layer in a proportion of 35% and TEG1 is present in the layer in a proportion of 10%. Analogously, the electron-transport layer may also consist of a mixture of two materials.

The OLEDs are characterised by standard methods. For this purpose, the electroluminescence spectra, the external quantum efficiency (EQE1000, measured in % at 1000 cd/m$^2$) and the voltage (U1000, measured at 1000 cd/m$^2$ in V) are determined from current/voltage/luminance characteristic lines (IUL characteristic lines) assuming a Lambertian emission profile. Lifetime LT is defined as the time in hours (h), after which the starting brightness is reduced to a certain level L1 in % of the starting brightness. Here L0; j0=4000 cd/m$^2$ and L1=70% in Table 2 means, that the starting brightness is reduced from 4000 cd/m$^2$ to 2800 cd/m$^2$ after the time in hours (h) of column "LT". Analogously, L0; j0=20 mA/cm$^2$, L1=80% means, that the starting brightness at a current density of 20 mA/cm$^2$ after the time "LT" in hours (h), is reduced to 80% of its starting value.

The device data of various OLEDs is summarized in Table 2. The examples V1-V4 are comparison examples according to the state-of-the-art. The examples E$^1$-E8 show data of OLEDs according to the invention.

In the following section, several examples are described in more detail to show the advantages of the inventive OLEDs.

Use of Inventive Compounds as Host Material in Phosphorescent OLEDs

The use of the inventive compounds in the emitting layer (EML) or in the electron-blocking layer (EBL) results in significantly improved OLED device data compared to state-of-the-art materials, especially with respect to lifetime.

The use of the inventive materials EgO1-Eg04 in combination with 105 and the green dopant TEG1 in phosphorescent green OLEDs results in an improved lifetime compared to devices with the materials SdT01-SdT02 (comparison of examples V1-V4 with E$^1$-E8).

The use of the inventive materials EgO1 to Eg04 in the electron blocking layer (EBL) of the OLED results in a significantly decreased voltage compared to devices with the materials SdT01 and SdT02 (comparison of examples V1-V4 with E$^1$-E8).

TABLE 1

OLED layer structure

| Ex. | HIL | IL | HTL | EBL | EML | HBL | ETL | EIL |
|---|---|---|---|---|---|---|---|---|
| V1 | SpA1 70 nm | HATCN 5 nm | SpMA1 70 nm | — | IC5:SdT01:TEG1 (47%:47%:6%) 30 nm | ST2 10 nm | ST2:LiQ (50%:50%) 30 nm | — |
| V2 | SpA1 70 nm | HATCN 5 nm | SpMA1 70 nm | — | IC5:SdT02:TEG1 (47%:47%:6%) 30 nm | ST2 10 nm | ST2:LiQ (50%:50%) 30 nm | — |
| V3 | SpA1 70 nm | HATCN 5 nm | SpMA1 70 nm | SdT01 20 nm | IC1:TEG1 (90%:10%) 30 nm | ST2 10 nm | ST2:LiQ (50%:50%) 30 nm | — |
| V4 | SpA1 70 nm | HATCN 5 nm | SpMA1 70 nm | SdT02 20 nm | IC1:TEG1 (90%:10%) 30 nm | ST2 10 nm | ST2:LiQ (50%:50%) 30 nm | — |
| E1 | SpAl 70 nm | HATCN 5 nm | SpMA1 70 nm | — | IC5:Eg01:TEG1 (47%:47%:6%) 30 nm | ST2 10 nm | ST2:LiQ (50%:50%) 30 nm | — |
| E2 | SpA1 70 nm | HATCN 5 nm | SpMA1 70 nm | — | IC5:Eg02:TEG1 (47%:47%:6%) 30 nm | ST2 10 nm | ST2:LiQ (50%:50%) 30 nm | — |
| E3 | SpA1 70 nm | HATCN 5 nm | SpMA1 70 nm | — | IC5:Eg03:TEG1 (47%:47%:6%) 30 nm | ST2 10 nm | ST2:LiQ (50%:50%) 30 nm | — |
| E4 | SpA1 70 nm | HATCN 5 nm | SpMA1 70 nm | — | IC5:Eg04:TEG1 (47%:47%:6%) 30 nm | ST2 10 nm | ST2:LiQ (50%:50%) 30 nm | — |
| E5 | SpA1 70 nm | HATCN 5 nm | SpMA1 70 nm | Eg01 20 nm | IC1:TEG1 (90%:10%) 30 nm | ST2 10 nm | ST2:LiQ (50%:50%) 30 nm | — |

TABLE 1-continued

| | | | | OLED layer structure | | | | |
|---|---|---|---|---|---|---|---|---|
| Ex. | HIL | IL | HTL | EBL | EML | HBL | ETL | EIL |
| E6 | SpA1 70 nm | HATCN 5 nm | SpMA1 70 nm | Eg02 20 nm | IC1:TEG1 (90%:10%) 30 nm | ST2 10 nm | ST2:LiQ (50%:50%) 30 nm | — |
| E7 | SpA1 70 nm | HATCN 5 nm | SpMA1 70 nm | Eg03 20 nm | IC1:TEG1 (90%:10%) 30 nm | ST2 10 nm | ST2:LiQ (50%:50%) 30 nm | — |
| E8 | SpA1 70 nm | HATCN 5 nm | SpMA1 70 nm | Eg04 20 nm | IC1:TEG1 (90%:10%) 30 nm | ST2 10 nm | ST2:LiQ (50%:50%) 30 nm | — |

TABLE 2

| | OLED device data | | | |
|---|---|---|---|---|
| Bsp. | U1000 (V) | $L_0$; $j_0$ | $L_1$ % | LD (h) |
| V1 | 3.0-3.3 | 20 mA/cm² | 80 | 30-50 |
| V2 | 3.0-3.3 | 20 mA/cm² | 80 | 40-60 |
| E1 | 3.0-3.3 | 20 mA/cm² | 80 | 80-100 |
| E2 | 3.0-3.3 | 20 mA/cm² | 80 | 100-120 |
| E3 | 3.0-3.3 | 20 mA/cm² | 80 | 100-120 |
| E4 | 3.0-3.3 | 20 mA/cm² | 80 | 80-100 |
| V3 | 4.1-4.6 | 20 mA/cm² | 80 | |
| V4 | 3.9-4.5 | 20 mA/cm² | 80 | |
| E5 | 3.4-3.7 | 20 mA/cm² | 80 | |
| E6 | 3.2-3.5 | 20 mA/cm² | 80 | |
| E7 | 3.2-3.5 | 20 mA/cm² | 80 | |
| E8 | 3.4-3.7 | 20 mA/cm² | 80 | |

TABLE 3

Chemical structures of the OLED materials

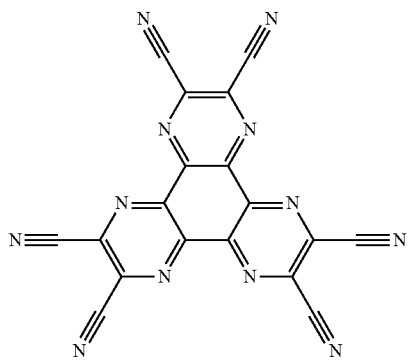

HATCN

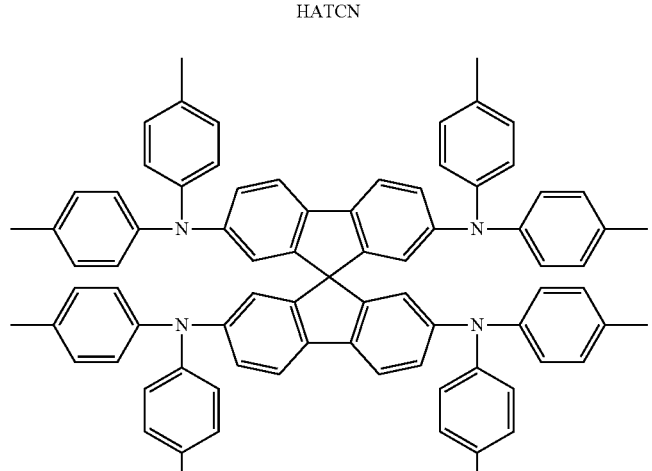

SpA1

TABLE 3-continued
Chemical structures of the OLED materials
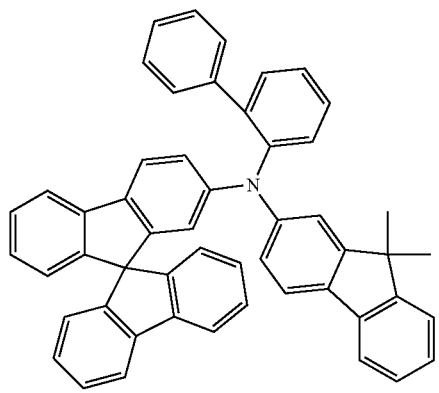
SpMA1
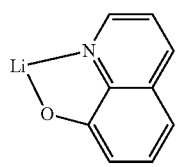
LiQ
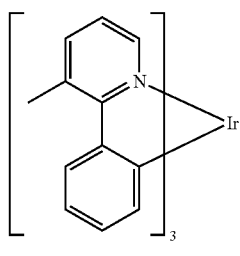
TEG1
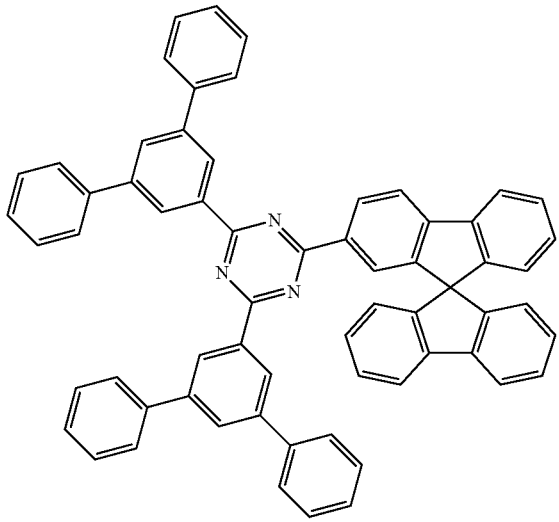
ST2

TABLE 3-continued
Chemical structures of the OLED materials
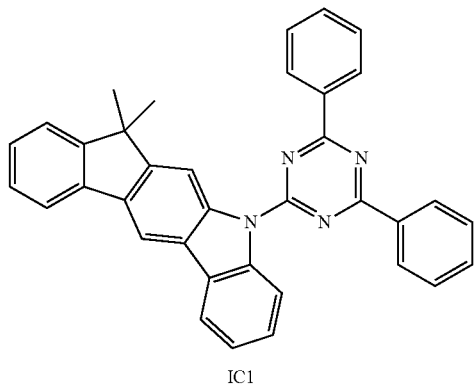
IC1
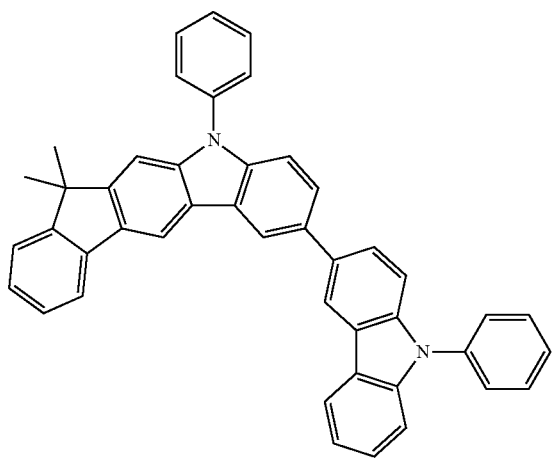
IC3
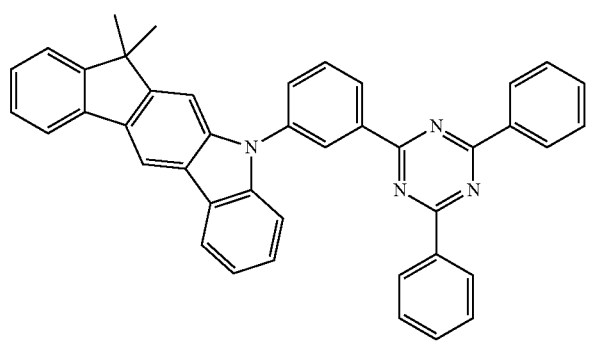
IC5

TABLE 3-continued
Chemical structures of the OLED materials
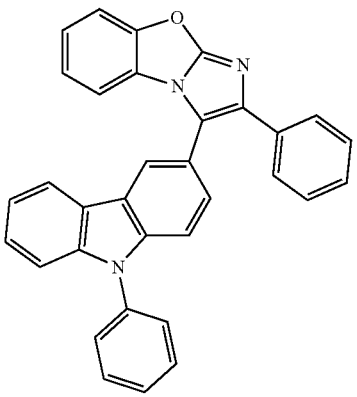
Eg01
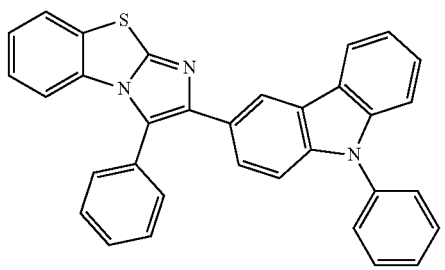
Eg02
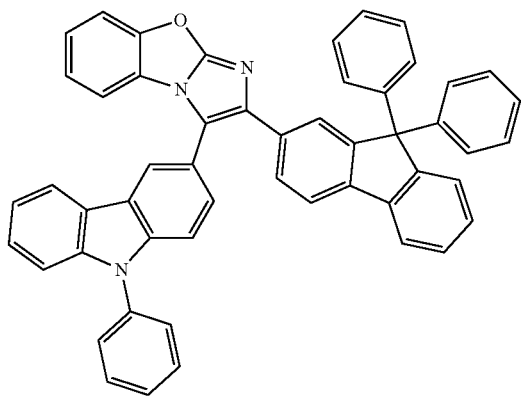
Eg03
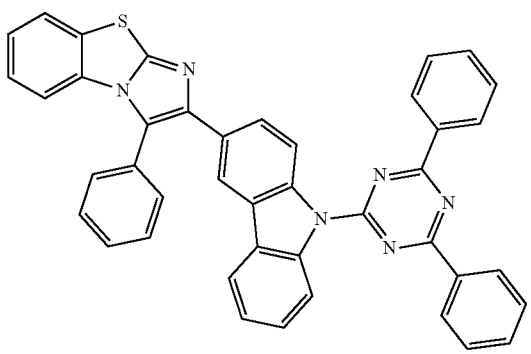
Eg04

TABLE 3-continued

Chemical structures of the OLED materials

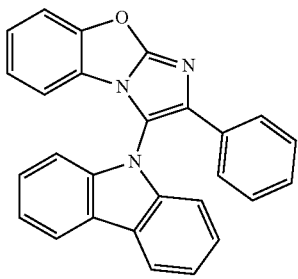

SdT01

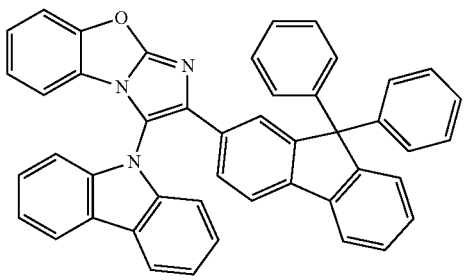

SdT02

The invention claimed is:

1. An organic electroluminescent device (OLED) comprising at least one compound of the formula (1) in an emitting layer or an electron-blocking layer,

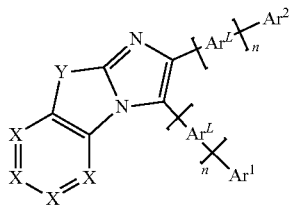

formula (1)

where the following applies to the symbols and indices used:

Y is S, O, or $NAr^N$;

X stands, on each occurrence, identically or differently, for N, $CR^1$, $C(Ar^L)_nAr^1$ or $C(Ar^L)_nAr^2$;

$Ar^L$, $Ar^N$ stand on each occurrence, identically or differently, for an aromatic or heteroaromatic ring system having 5 to 60 aromatic ring atoms, which may be substituted by one or more radicals $R^2$;

$Ar^1$, $Ar^2$ stand on each occurrence, identically or differently, for an aromatic or heteroaromatic ring system having 5 to 60 aromatic ring atoms, which may be substituted by one or more radicals $R^3$;

where the compound of formula (1) comprises at least one group $Ar^1$ or $Ar^2$, which stands for a heteroaromatic ring system of formula (Cbz-1):

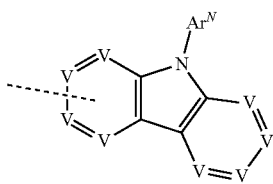

formula (Cbz-1)

where the dashed bond indicates the bonding of $A^1$ or $Ar^2$ to the structure of formula (1) or to $Ar^L$;

V stands, on each occurrence, identically or differently, for $CR^3$ or N; or V stands for C when it is bonded to the structure of formula (1) or to $Ar^L$ or two adjacent groups V stand for a group of formula (V-1) or (V-2),

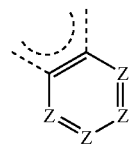

Formula (V-1)

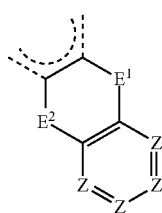

Formula (V-2)

where the dashed bonds in formulae (V-1) and (V-2) indicate the bonding to the group of formula (Cbz-1);

Z is on each occurrence, identically or differently, $CR^3$ or N;

$E^1$, $E^2$ are, on each occurrence, identically or differently, selected from a single bond, $B(R^0)$, $C(R^0)_2$, $Si(R^0)_2$, C=O, C=NR$^0$), C=C(R$^0$)$_2$, O, S, S=O, SO$_2$, N(R$^0$), P(R$^0$) and P(=O)R$^0$, where at least one of the two groups $E^1$ and $E^2$ present in the same ring, is not a single bond;

$R^0$ stands on each occurrence, identically or differently, for H, D, F, Cl, Br, I, CN, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^4$, where in each case one or more non-adjacent CH$_2$ groups may be replaced by $R^4C$=CR$^4$, C≡C, Si(R$^4$)$_2$, Ge(R$^4$)$_2$, Sn(R$^4$)$_2$, C=O, C=S, C=Se, P(=O)(R$^4$), SO, SO$_2$, O, S or CONR$^4$ and where one or more H atoms may be replaced by D, F, Cl, Br, I, CN or NO$^2$, an aromatic or heteroaromatic ring systems having 5 to 60 aromatic ring atoms, which may in each case be substituted by one or more radicals $R^4$, or an aryloxy groups having 5 to 60 aromatic ring atoms, which may be substituted by one or more radicals $R^4$, where two adjacent substituents $R^0$ may form an aliphatic or aromatic ring system together, which may be substituted by one or more radicals $R^4$;

$R^1$, $R^2$, $R^3$ stand on each occurrence, identically or differently, for H, D, F, Cl, Br, I, CHO, CN, C(=O)Ar, P(=O)(Ar)$_2$, S(=O)Ar, S(=O)$_2$Ar, N(R$^4$)$_2$, N(Ar)$_2$, NO$_2$, Si(R$^4$)$_3$, B(OR$^4$)$_2$, OSO$_2$R$^4$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^4$, where in each case one or more non-adjacent CH$_2$ groups may be replaced by $R^4C$=CR$^4$, C≡C, Si(R$^4$)$_2$, Ge(R$^4$)$_2$, Sn(R$^4$)$_2$, C=O, C=S, C=Se, P(=O)(R$^4$), SO, SO$_2$, O, S or CONR$^4$ and where one or more H atoms may be replaced by D, F, Cl, Br, I, CN or NO$_2$, an aromatic or heteroaromatic ring systems having 5 to 60 aromatic ring atoms, which may in each case be substituted by one or more radicals $R^4$, or an aryloxy groups having 5 to 60 aromatic ring atoms, which may be substituted by one or more radicals $R^4$; where two adjacent substituents $R^1$, two adjacent substituents $R^2$ and/or two adjacent substituents $R^3$ may form an aliphatic or aromatic ring system together, which may be substituted by one or more radicals $R^4$;

$R^4$ stands on each occurrence, identically or differently, for H, D, F, Cl, Br, I, CHO, CN, C(=O)Ar, P(=O)(Ar)$_2$, S(=O)Ar, S(=O)$_2$Ar, N(R$^5$)$_2$, N(Ar)$_2$, NO$_2$, Si(R$^5$)$_3$, B(OR$^5$)$_2$, OSO$_2$R$^5$, a straight-chain alkyl, alkoxy or thioalkyl groups having 1 to 40 C atoms or branched or a cyclic alkyl, alkoxy or thioalkyl groups having 3 to 40 C atoms, each of which may be substituted by one or more radicals $R^5$, where in each case one or more non-adjacent CH$_2$ groups may be replaced by $R^5C$=CR$^5$, C≡C, Si(R$^5$)$_2$, Ge(R$^5$)$_2$, Sn(R$^5$)$_2$, C=O, C=S, C=Se, P(=O)(R$^5$), SO, SO$_2$, O, S or CONR$^5$ and where one or more H atoms may be replaced by D, F, Cl, Br, I, CN or NO$_2$, an aromatic or heteroaromatic ring systems having 5 to 60 aromatic ring atoms, which may in each case be substituted by one or more radicals $R^5$, or an aryloxy groups having 5 to 60 aromatic ring atoms, which may be substituted by one or more radicals $R^5$; where two adjacent substituents $R^4$ may form an aliphatic or aromatic ring system together, which may be substituted by one or more radicals $R^5$;

Ar is, on each occurrence, identically or differently, an aromatic or heteroaromatic ring system having 5 to 60 aromatic ring atoms, which may in each case also be substituted by one or more radicals $R^5$;

$R^5$ stands on each occurrence, identically or differently, for H, D, F, Cl, Br, I, CN, a straight-chain alkyl, alkoxy or thioalkyl groups having 1 to 20 C atoms or branched or cyclic alkyl, alkoxy or thioalkyl groups having 3 to 20 C atoms, where in each case one or more non-adjacent CH$_2$ groups may be replaced by SO, SO$_2$, O, S and where one or more H atoms may be replaced by D, F, Cl, Br or I, or an aromatic or heteroaromatic ring system having 5 to 24 aromatic ring atoms;

n is an integer equal to 0, 1, 2 or 3.

2. The OLED according to claim 1, characterized in that the group Y is selected from O or S.

3. The OLED according to claim 1, characterized in that V stands, on each occurrence, identically or differently, for $CR^3$ or N.

4. The OLED according to claim 1, wherein the compound is selected from the compounds of formulae (2-1) to (2-6) as listed below, formula (2-1)

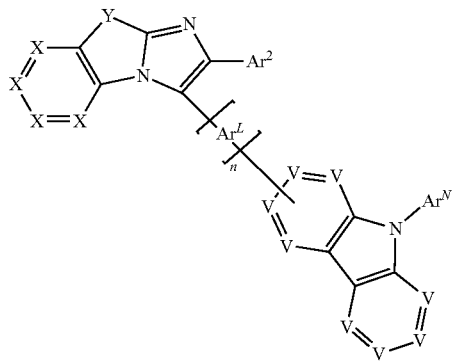

formula (2-2)

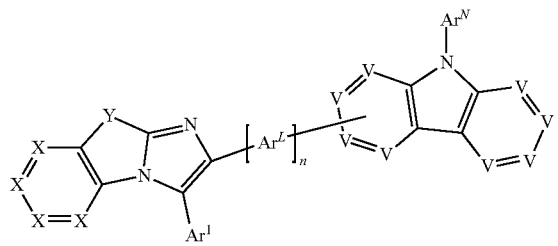

-continued formula (2-3)

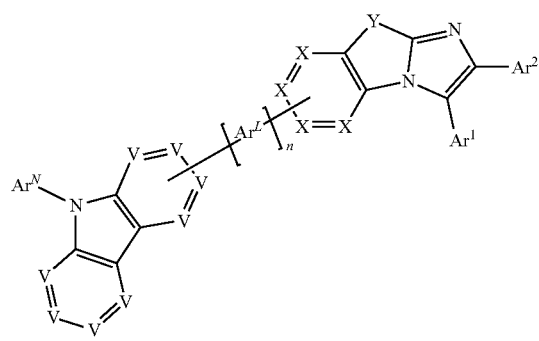

formula (2-4)

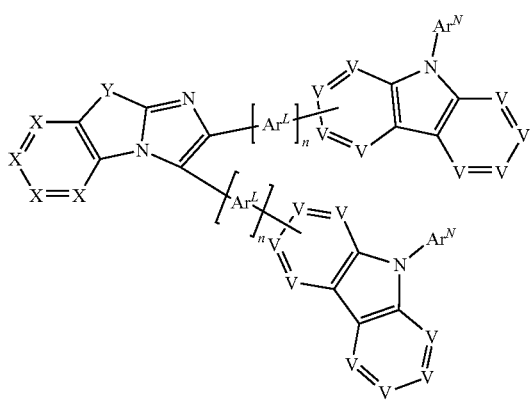

formula (2-5)

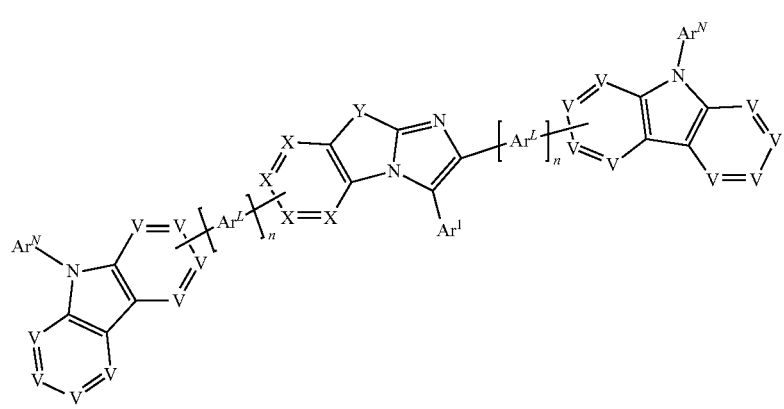

formula (2-6)

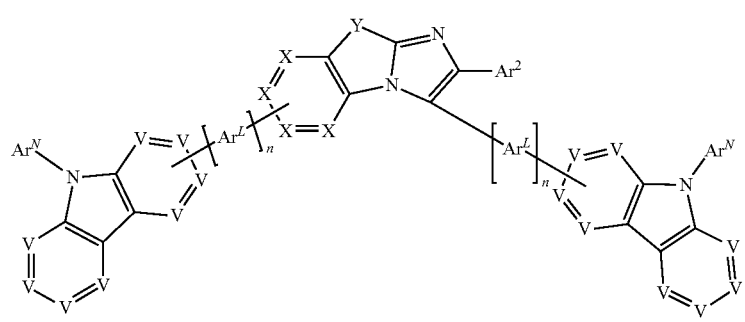

where the symbols V, Y, $Ar^1$, $Al^2$, $Ar^L$ and $Ar^N$ the index n have the same meaning as in claim 1, the symbol X also has the same meaning as in claim 1, with the proviso that X stands for C in formulae (2-5) and (2-6) if it is bonded to the adjacent carbazole unit or the group $Ar^L$.

5. The OLED according to claim 1, wherein n is on each occurrence, identically or differently, 0 or 1, wherein when n is 1, then the group $Ar^L$ is present and stands for a group of formula (Cbz-2):

formula (Cbz-2)

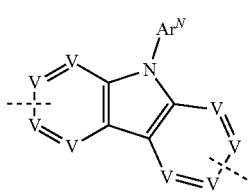

where the dashed bonds indicate the bonding to the group $A^1$ or $Ar^2$ and to the structure of formula (1), and where the symbols V and have the same meaning as in claim 1.

6. The OLED according to claim 1, wherein the compound is selected from the compounds of formulae (3-1) to (3-6) as listed below, formula (3-1)

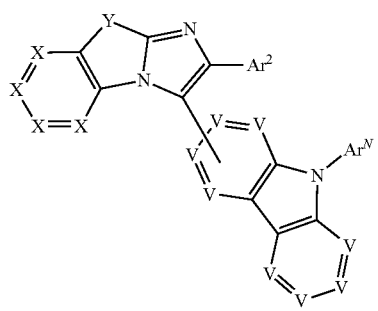

formula (3-2)

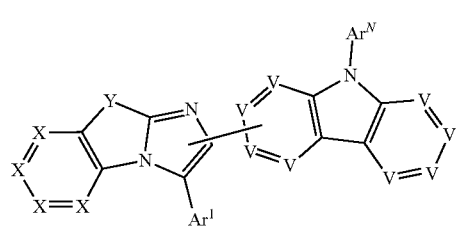

formula (3-3)

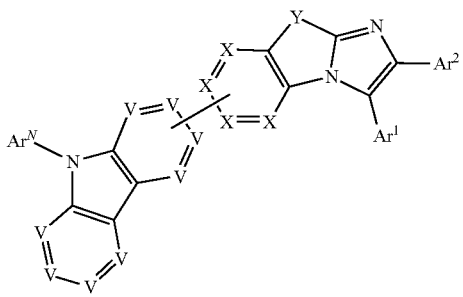

formula (3-4)

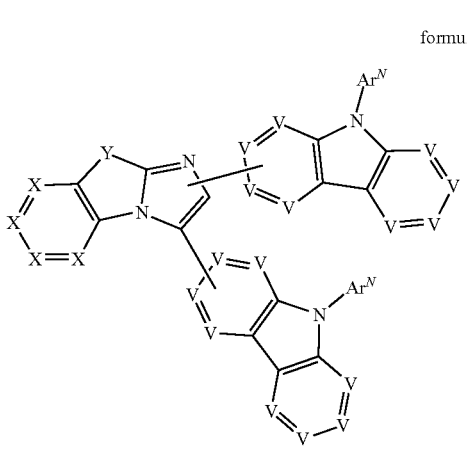

formula (3-5)

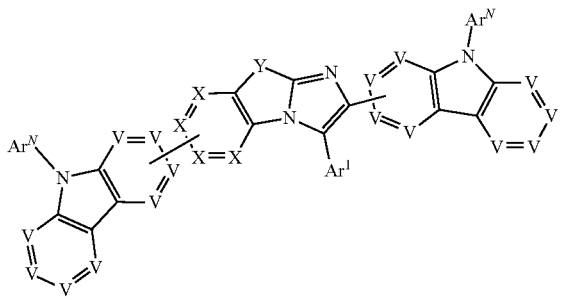

(formula (3-6))

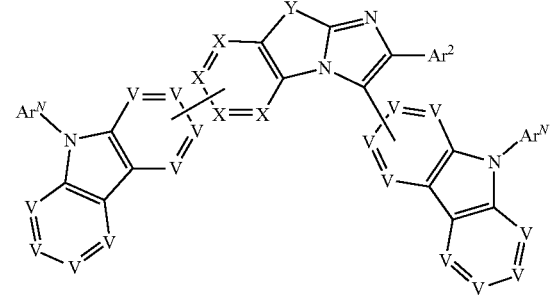

where the symbols V, Y, $Ar^1$, $Ar^2$ and have the same meaning as in claim 1, the symbol X has the same meaning as in claim 1 in formulae (3-1) to (3-4), the symbol X also has the same meaning as in claim 1, with the proviso that X stands for C in formulae (3-5) and (3-6) if it is bonded to the adjacent carbazole unit.

7. The OLED according to claim 1, wherein the compound comprises at least one group $A^1$ or $Ar^2$, which stands for a group of formula (Cbz-1a), formula (Cbz-1a)

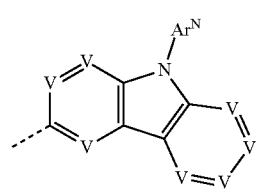

where the dashed bond indicates the bonding to the structure of formula (1) or to ArL.

8. The OLED according to claim 1, wherein the compound is selected from the compounds of formulae (4-1) to (4-6) as listed below,

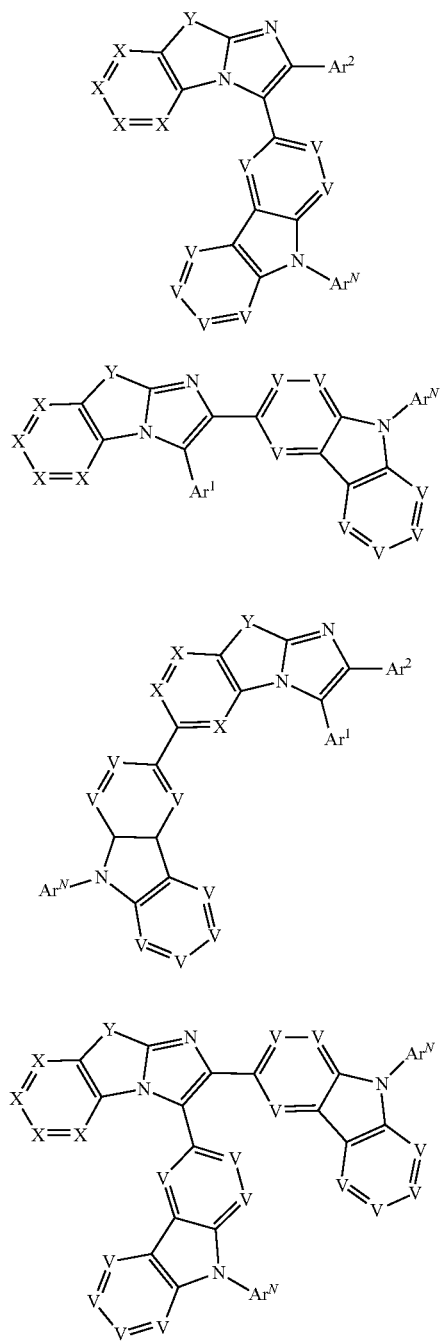

formula (4-1)

formula (4-2)

formula (4-3)

(formula (4-4)

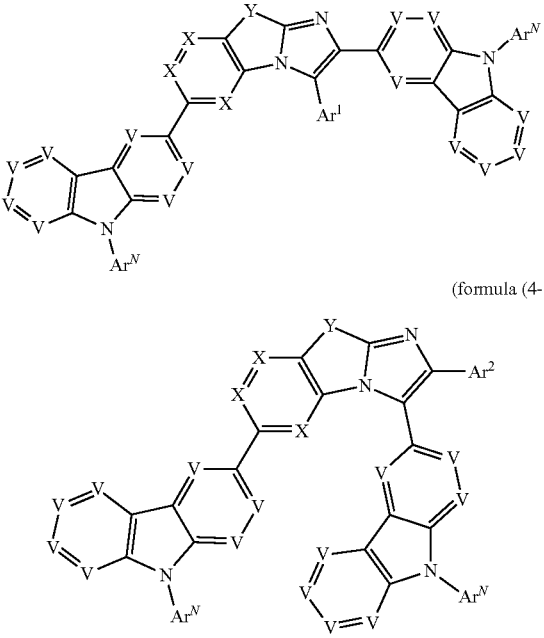

formula (4-5)

(formula (4-6)

where the symbols X, V, Y, Ar$^1$, Ar$^2$ and Ar$^N$ have the same meaning as in claim 1.

9. The OLED according to claim 1, wherein Ar$^N$ is, on each occurrence, identically or differently, selected from the group consisting of phenyl, biphenyl, terphenyl, quaterphenyl, fluorene, spirobifluorene, naphthalene, anthracene, phenanthrene, triphenylene, fluoranthene, indole, benzofuran, benzothiophen, dibenzofuran, dibenzothiophene, carbazole, indenocarbazole, indolocarbazole, pyridine, pyrimidine, pyrazine, pyridazine, triazine, quinolone, benzopyridine, benzopyridazine, benzopyrimidine, quinazoline, benzimidazole, or a combination of two or three of these groups, each of which may be substituted by one or more radicals R$^2$.

10. The OLED according to claim 1, wherein the compound is employed as a matrix material for emitters, a hole-transport-material or an electron-transport material.

11. The OLED according to claim 1, wherein the compound is employed as a matrix material in an emitting layer comprising said at least one compound and at least one emitter.

12. The OLED according to claim 11, wherein the emitter is a phosphorescent material.

13. The OLED according to claim 11, wherein Y is O or NAr$^N$.

* * * * *